United States Patent
Schiemann et al.

(10) Patent No.: US 7,893,082 B2
(45) Date of Patent: Feb. 22, 2011

(54) SUBSTITUTED TETRAHYDROQUINOLINES

(75) Inventors: Kai Schiemann, Seeheim-Jugenheim (DE); Ulrich Emde, Darmstadt (DE); Dirk Finsinger, Darmstadt (DE); Christiane Amendt, Darmstadt (DE); Nina Heiss, Heidelberg (DE); Frank Zenke, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 294 days.

(21) Appl. No.: 11/916,952

(22) PCT Filed: May 17, 2006

(86) PCT No.: PCT/EP2006/004656
§ 371 (c)(1),
(2), (4) Date: Dec. 7, 2007

(87) PCT Pub. No.: WO2007/054138
PCT Pub. Date: May 18, 2007

(65) Prior Publication Data
US 2008/0194615 A1    Aug. 14, 2008

(30) Foreign Application Priority Data
Jun. 13, 2005 (DE) .................. 10 2005 027 170

(51) Int. Cl.
*A61K 31/4375* (2006.01)
*A61K 31/436* (2006.01)
*C07D 491/052* (2006.01)
*C07D 471/04* (2006.01)

(52) U.S. Cl. .................. 514/291; 514/292; 546/81; 546/89

(58) Field of Classification Search ............. 546/81, 546/89; 514/291, 292
See application file for complete search history.

(56) References Cited

U.S. PATENT DOCUMENTS

| 6,423,715 B1 * | 7/2002 | Hardy et al. ................. 514/250 |
| 2003/0149069 A1 | 8/2003 | Li et al. |
| 2007/0203167 A1 * | 8/2007 | Schiemann ................. 514/291 |
| 2009/0176820 A1 * | 7/2009 | Schiemann et al. .......... 514/291 |

FOREIGN PATENT DOCUMENTS

| WO | 9827093 | * | 6/1998 |
| WO | 2005/016255 | | 2/2005 |
| WO | 2005/063735 | | 7/2005 |
| WO | 2005063735 | * | 7/2005 |
| WO | 2005105802 | * | 11/2005 |

OTHER PUBLICATIONS

Kobayashi et al., Journal of the American Chemical Society (1996), 118(37), 8977-8978.*
Katritzky et al., Journal of Organic Chemistry (1995), 60(13), 3993-4001.*
Ravindranath et al., A facile and convenient three component coupling protocol for the synthesis of pyrano and furoquinolines, Chemistry Letters, vol. 32, No. 3, pp. 222-223, 2003.
Yun Ma et al., Lanthanide chloride catalyzed imino Diels Alder reaction. One-pot synthesis of pyrano and furoquinolines, Journal of Organic Chemistry, vol. 64, pp. 6462-6467, 1999.
Yadav J. S. et al., Lithium perchlorate/diethylether catalyzed aza-Diels-Alder reaction: an expeditious synthesis of pyrano, indeno quinolines and phenanthridines, Synlett, No. 2, pp. 240-242, 2001.
Xia Y et al. Antitumor agents. 181. Synthesis and biological evaluation of 6,7,2' ,3' ,4'-substituted-1,2,3,4-tetrahydro-2-phenyl-4-quinolones as a new class of antimitotic antitumor agents, Journal of Medicinal Chemistry, vol. 41, pp. 1155-1162, 1998.

* cited by examiner

*Primary Examiner*—D. Margaret Seaman
*Assistant Examiner*—Niloofar Rahmani
(74) *Attorney, Agent, or Firm*—Perkins Coie LLP

(57) ABSTRACT

Disclosed are compounds of formula (I), wherein W, R, $R^1$, $R^2$, $R^3$, $R^4$, $R^5$, $R^6$, and $R^7$ have the meanings indicated in claim 1. Said compounds can be used for the treatment of tumors, among other things.

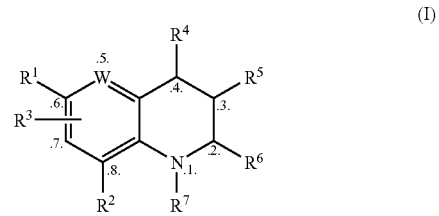

(I)

14 Claims, No Drawings

SUBSTITUTED TETRAHYDROQUINOLINES

BACKGROUND OF THE INVENTION

The invention had the object of finding novel compounds having valuable properties, in particular those which can be used for the preparation of medicaments.

The present invention relates to compounds of the formula I and to the use thereof for the treatment and prophylaxis of diseases in which the inhibition, regulation and/or modulation of mitotic motor proteins, in particular the mitotic motor protein Eg5, plays a role, furthermore to pharmaceutical compositions which comprise these compounds.

In detail, the present invention relates to compounds of the formula I which preferably inhibit, regulate and/or modulate one or more mitotic motor proteins, to compositions which comprise these compounds, and to methods for the use thereof for the treatment of diseases and complaints such as angiogenesis, cancer, tumour formation, growth and propagation, arteriosclerosis, ocular diseases, choroidal neovascularisation and diabetic retinopathy, inflammatory diseases, arthritis, neurodegeneration, restenosis, wound healing or transplant rejection. In particular, the compounds according to the invention are suitable for the therapy or prophylaxis of cancer diseases.

During mitosis, various kinesins regulate the formation and dynamics of the spindle apparatus, which is responsible for correct and coordinated alignment and separation of the chromosomes. It has been observed that specific inhibition of a mitotic motor protein—Eg5—results in collapse of the spindle fibres. The result of this is that the chromosomes can no longer be distributed correctly over the daughter cells. This results in mitotic arrest and can consequently cause cell death. Upregulation of the motor protein Eg5 has been described, for example, in tissue from breast lung and colon tumours. Since Eg5 takes on a mitosis-specific function, it is principally rapidly dividing cells and not fully differentiated cells that are affected by Eg5 inhibition. In addition, Eg5 regulates exclusively the movement of mitotic microtubuli (spindle apparatus) and not that of the cytoskeleton. This is crucial for the side-effect profile of the compounds according to the invention since, for example, neuropathies, as observed in the case of Taxol, do not occur or only do so to a weakened extent. The inhibition of Eg5 by the compounds according to the invention is therefore a relevant therapy concept for the treatment of malignant tumours.

In general, all solid and non-solid tumours can be treated with the compounds of the formula I, such as, for example, monocytic leukaemia, brain, urogenital, lymphatic system, stomach, laryngeal and lung carcinoma, including lung adenocarcinoma and small-cell lung carcinoma. Further examples include prostate, pancreatic and breast carcinoma.

Surprisingly, it has been found that the compounds according to the invention effect specific inhibition of mitotic motor proteins, in particular Eg5. The compounds according to the invention preferably exhibit an advantageous biological activity which can easily be detected in the assays described herein, for example. In such assays, the compounds according to the invention preferably exhibit and cause an inhibiting effect, which can usually be documented by $IC_{50}$ values in a suitable range, preferably in the micromolar range and more preferably in the nanomolar range.

As discussed herein, effects of the compound according to the invention are relevant to various diseases. Accordingly, the compounds according to the invention are useful in the prophylaxis and/or treatment of diseases which are influenced by inhibition of one or more mitotic motor proteins, in particular Eg5.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases, and also to a method for the treatment of the said diseases comprising the administration of one or more compounds according to the invention to a patient in need of such an administration.

It can be shown that the compounds according to the invention have an advantageous effect in a xenotransplant tumour model.

The host or patient can belong to any mammal species, for example a primate species, particularly humans; rodents, including mice, rats and hamsters; rabbits; horses, cattle, dogs, cats, etc. Animal models are of interest for experimental investigations, providing a model for the treatment of a human disease.

The susceptibility of a certain cell to treatment with the compounds according to the invention can be determined by testing in vitro. Typically, a culture of the cell is combined with a compound according to the invention at various concentrations for a periodine which is sufficient to enable the active ingredients to inhibit cell proliferation or induce cell death, usually between approximately one hour and one week. For testing in vitro, cultivated cells from a biopsy sample or established cell lines can be used. The viable cells remaining after the treatment are then counted.

The dose varies depending on the specific compound used, the specific disease, the patient status, etc. Typically, a therapeutic dose is sufficient considerably to reduce the undesired cell population in the target tissue, while the viability of the patient is maintained. The treatment is generally continued until a considerable reduction has occurred, for example at least about a 50% reduction in the cell burden, and can be continued until essentially no undesired cells are detected in the body.

SUMMARY OF THE INVENTION

The invention relates to compounds of the formula I

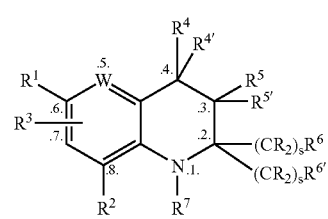

in which
W denotes CH or N,
R$^1$, R$^2$, R$^3$, independently of one another, denote H, A, aryl, heteroaryl, Hal, —(CY$_2$)$_n$—SA, —(CY$_2$)$_n$—SCF$_3$, —(CY$_2$)$_n$—SCN, —(CY$_2$)$_n$—CF$_3$, —(CY$_2$)$_n$—OCF$_3$, R, NR—NR$_2$, X(CY$_2$)$_n$XR, X(CY$_2$)$_n$Y, (CY$_2$)$_n$-cycloalkyl, (CY$_2$)$_n$CH=CH$_2$, cycloalkyl, —SCH$_3$, —SCN, —CF$_3$, —OCF$_3$, —OA, —(CY$_2$)$_n$—OH, —(CY$_2$)$_n$—CO$_2$R, —(CY$_2$)$_n$—CN, —(CY$_2$)$_n$-Hal, —(CY$_2$)$_n$—Y, (CY$_2$)$_n$R$^a$, —(CY$_2$)$_n$—NR$_2$, (CY$_2$)$_n$—OA, (CY$_2$)$_n$—OCOA, —SCF₃, —(CY₂)ₙ—CONR₂, —(CY₂)ₙ—NHCOA, —(CY₂)ₙ—NHSO₂A, SF₅, Si(CH₃)₃, CO—(CY₂)ₙ—CH₃, —(CY₂)ₙ—N-pyrolidone, (CH₂)ₙNRCOOR, NRCOOR, NCO, (CH₂)ₙCOOR, NCOOR, (CH₂)ₙOH, NR(CH₂)ₙNR₂, C(OH)R₂, NR(CH₂)ₙOR, NCOR, (CH₂)ₙ-aryl, (CH₂)ₙ-heteroaryl, (CH₂)ₙR¹, (CH₂)ₙX (CH₂)ₙ-aryl, (CH₂)ₙX(CH₂)ₙ-heteroaryl, (CH₂)ₙCONR₂, XCONR(CH₂)ₙNR₂, N[(CH₂)ₙXCOOR]CO(CH₂)ₙ-aryl, N[(CH₂)ₙXR]CO(CH₂)ₙ-aryl, N[(CH₂)ₙXR]CO(CH₂)ₙX-aryl, N[(CH₂)ₙXR]SO₂(CH₂)ₙ-aryl, N[(CH₂)ₙNRCOOR] CO(CH₂)ₙ-aryl, N[(CH₂)ₙNR₂]CO(CH₂)ₙ-aryl, N[(CH₂)ₙ NR₂]CO(CH₂)ₙNR-aryl, N[(CH₂)ₙNR₂]SO₂(CH₂)ₙ-aryl, N[(CH₂)ₙXR]CO(CH₂)ₙ-heteroaryl, N[(CH₂)ₙXR]CO (CH₂)ₙX-heteroaryl, CO-aryl, SO₂-aryl, N [(CH₂)ₙXR] SO₂(CH₂)ₙ-heteroaryl, N[(CH₂)ₙNRCOOR]-CO(CH₂)ₙ-heteroaryl, N[(CH₂)ₙNR₂]CO(CH₂)ₙ-heteroaryl, N[(CH₂)ₙ NR₂]CO(CH₂)ₙNR-heteroaryl, R¹ and R³ together also denote —N—C(CF₃)=N—, —N—CR=N—, —N—N=N— and where non-adjacent CY₂ groups may also be replaced by X Y denotes H, A, Hal, OR, E-R¹, E denotes —NR¹SO₂—, —SO₂NR¹—, —CONR¹—, —NR¹CO—, —COO—, OOC—, CO, —SO₂—, —X—, NR¹CONR¹—, —OCONR¹—, —NR¹COO—, —CSNR¹—, —NR¹CS—, —NR¹CSNR¹—, —SCONR¹—, —NR¹COS—, —OCSNR¹—, NR¹CSO—, SCSNR¹—, —NR¹CSS or a single bond A denotes alkyl or cycloalkyl, in which one or more H atoms may be replaced by Hal, Hal denotes F, Cl, Br or I R denotes H or A, in the case of geminal radicals R together also —(CH₂)₅—, —(CH₂)₄— or —(CH₂)ₙ—X—(CH₂)ₙ, or —(CH₂)ₙ-Z-(CH₂)ₙ,

R⁴, R⁴',

R⁵, R⁵', independently of one another, denote H or unsubstituted or mono- or poly-OR—, —NO₂—, -Hal-, —CF₃—, —OCF₃—, —CN—, —NR₂— or —SR—, -aryl- or -heteroaryl-substituted N-pyrolidone, Q, —(CY₂)ₙ-E-CR₂R¹, —(CY₂)ₙ-E-CR₂XR¹, —(CY₂)ₙ-E-(CY₂)ₙ—XR¹ or —(CY₂)ₙ-E-(CY₂)ₙ—XRᵃ, —X—(CH₂)₂OR, —X—CO (CH₂)ₙCH₃, —X—(CH₂)₂NR₂, R¹, S-aryl, O-aryl, CH₂Si (CH₃)₃, or together denote —X(CR₂)₂—, —X—(CR₂)₃—, —XCHQCY₂—, —X—CH(CH₂OR) (CY₂)₂—, —X—CH(CH₂NR₂)(CY₂)₂—, —X—CH=CQ-CH₂—, X-CQ=CH—CH₂—, —X(CH₂)₂ NR₂, —(CR₂)₃—, —(CR₂)₄—, —CR=CR—CR=CR—, —XCHQ(CY₂)₂—, —XCHQCR₂—, R—N—(C=X)—N—R, —XC[(CH₂)ₙOR]₂—CH₂CH₂—, —X—CY₂CH(CH₂OR)CY₂—, —X—CY₂CH(C H₂NR₂)CY₂—, —X—CY₂CHQ-CY₂—, —XCHQCY₂—, —XCY₂CHQ-, —XCHQ (CY₂)₃—, —XCHQ(CY₂)₄—, —XCY₂CHQ(CY₂)₂—, —XCY₂CHQ(CY₂)₃—, X denotes O, S or NR¹, Q denotes (CH₂)ₚ-E-(CH₂)ₚR¹, (CH₂)ₚ-E-(CH₂)ₚRᵃ, (CH₂)ₚ Hal, CHO, (CH₂)ₚSR¹, CORᵃ, (CH₂)ₚRᵃ, (CH₂)ₚOCORᵃ, (CH₂)ₚNCOR¹, (CH₂)ₚN(R¹)₂, (CH₂)ₚOR¹, (CH₂)ₚO-CON(R¹)₂, (CH₂)ₚOCOOR¹, (CH₂)ₚNHCON(R¹)₂, (CH₂)ₚNHCOOR¹, (CH₂)ₚCN, (CH₂)ₚCOOR¹

Rᵃ denotes

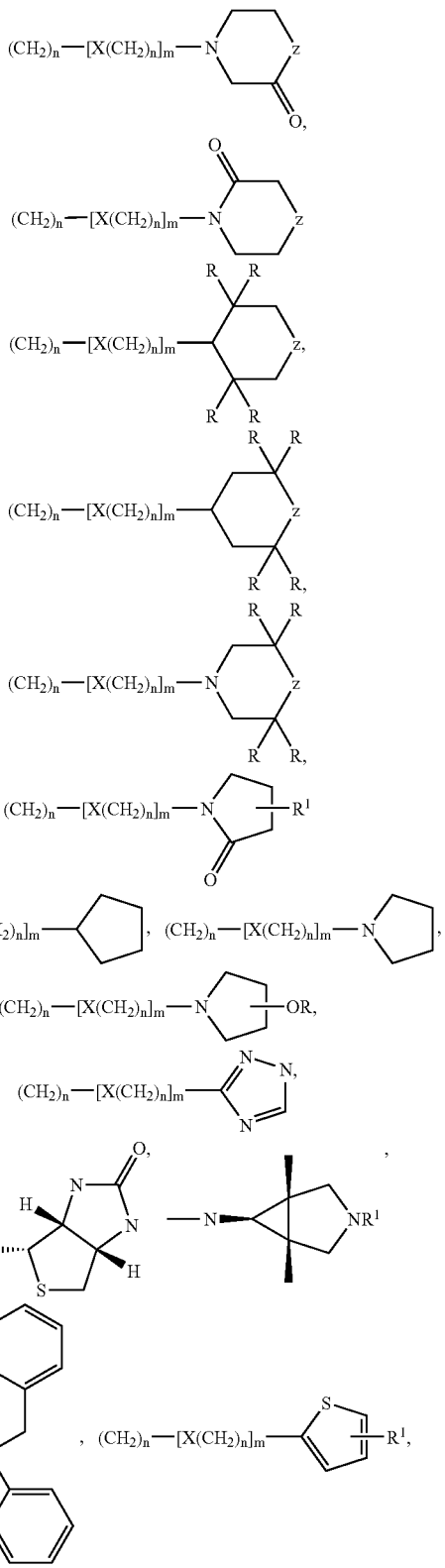

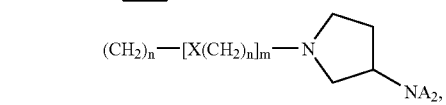

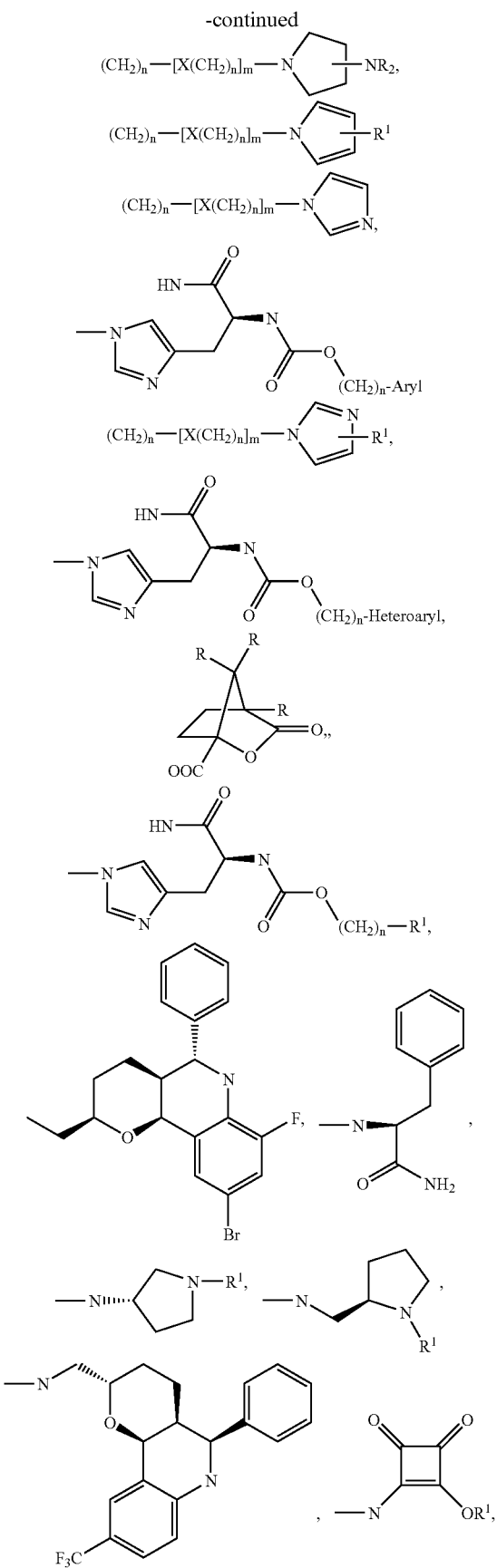

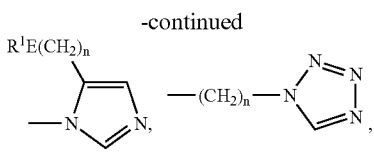

OR, NHR, $NR_2$, $NR(CH_2)_n$-aryl, $NR(CH_2)_n$OR, COOR, N-pyrrolidone radical, OCOR, $NR(CH_2)_nNR_2$, $(CY_2)_n$-aryl, $(CY_2)_2$-heteroaryl, $N[(CH_2)_nNR_2]CO(CH_2)_n$-aryl, $N[(CH_2)_n-NHCOOR]CO$-aryl, $R^1$, $N[CH_2(CH_2)_nOR]_2$, $NR(CH_2)_nNCOOR$, $X(CH_2)_nX(CH_2)_nXR$, $NR(CH_2)_nX(CH_2)_nOH$, $NR(CH_2)_n-O-(CH_2)_n-OH$, $(CH_2)_nCOOR$, $O(CO)NR(CH_2)_nOR$, $O(CO)(CH_2)_nNR_2$, $NR(CH_2)_nNR_2$, $N[(CH_2)_nNR_2]CO(CH_2)_n$-aryl, $N[(CH_2)_nXR]-CO(CH_2)_n$-aryl, $N[(CH_2)_nXR]CO(CH_2)_n$-heteroaryl, $N[(CH_2)_nNR_2]CO(CH_2)_n$-heteroaryl, $N[(CH_2)_nNR_2]CO(CH_2)_nR^1$, $N(R)(CH_2)_nN(R)COOR$, $XCOO(CH_2)_nNR_2$, $OSO_2A$, $OSO_2CF_3$, $OSO_2Ar$, $OCONR_2$, $OCH_2(CH_2)_nNR_2$, $CONR^1$, $COR^1$, Z denotes $CH_2$, X, $CHCONH_2$, $CH(CH_2)_nNR^1COOR^1$, $CHNR^1COOR^1$, NCHO, $CHCON(R^1)_2$, $CH(CH_2)_nCOOR^1$, $NCOOR^1$, $CH(CH_2)_nOH$, $N(CH_2)_nOH$, $CHNH_2$, $CH(CH_2)_nNR^1_2$, $CH(CH_2)_nNR^1_2$, $C(OH)R^1$, $CHNCOR^1$, $NCOR^1$, $N(CH_2)_n$-aryl, $N(CH_2)_n$-heteroaryl, $CHR^1$, $NR^1$, $CH(CH_2)_n$-aryl, $CH(CH_2)_n$-heteroaryl, $CH(CH_2)_nR^1$, $N(CH_2)_nCOOR^1$, $CH(CH_2)_nX(CH_2)_n$-aryl, $CH(CH_2)_nX(CH_2)_n$-heteroaryl, $NSO_2R$, $N(CH_2)_nCON(R^1)_2$, $NSO_2R^1$, $CHSO_2N(R^1)_2$, $XCONR(CH_2)_nN(R^1)_2$, $NCO(CH_2)_n$-aryl, $NCO(CH_2)_nX$-aryl, $NSO_2(CH_2)_n$-aryl, $NCO(CH_2)_n$-aryl, $NCO(CH_2)_nNR^1$-aryl, $NCO(CH_2)_n$-heteroaryl, $NCO(CH_2)_nX$-heteroaryl, $NSO_2(CH_2)_n$-heteroaryl, $NCO(CH_2)_n NR^1$-heteroaryl, $N(CH_2)_nNR_2CH$, $CHO(CH_2)_nN(R^1)_2$, $CHX(CH_2)_nN(R^1)_2$, $NCO(CH_2)_n NR_2$, $CHR^a$, $NR^a$, $C(OH)CY_3$, $C(OH)$-aryl, $C(NR_2)$-aryl, $R^6$ denotes aryl or heteroaryl, each of which is unsubstituted or mono- or polysubstituted by aryl or heteroaryl (which may be substituted by Hal, $NO_2$, CN, A, OR, OCOR, COR, $NR_2$, $CF_3$, $OCF_3$, $OCH(CF_3)_2$), or by Hal, $NO_2$, CN, OR, A, $-(CY_2)_n-OR$, $-OCOR$, $-(CY_2)_n-CO_2R$, $-(CY_2)_n-CN$, $-NCOR$, $-COR$ or $-(CY_2)_n-NR_2$, $R^{6'}$ denotes H or $R^6$ $R^7$ denotes (C=O)—R, (C=O)—$NR_2$, (C=O)—OR, H or A m denotes 0, 1 or 2 and n denotes 0, 1, 2, 3, 4, 5, 6 or 7 p denotes 0, 1, 2, 3, 4, or 5, preferably 1 or 2

S denotes 0, 1, 2, 3 or 4, in particular 0 and pharmaceutically usable derivatives, solvates, tautomers, salts and stereoisomers thereof, including mixtures thereof in all ratios.

The invention also relates to the optically active forms, the enantiomers, the racemates, the diastereomers and the hydrates and solvates of these compounds. The term solvates of the compounds is taken to mean adductions of inert solvent molecules onto the compounds of the formula I which form owing to their mutual attractive force. solvates are, for example, mono- or dihydrates or alkoxides.

Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

Similar compounds are described, for example, in Tetrahedron Lett. 1988, 29, 5855-5858, Tetrahedron Lett. 2003, 44, 217-219, J. Org. Chem. 1997, 62, 4880-4882, J. Org. Chem. 1999, 64, 6462-6467, Chem. Lett. 1995, 423-424, J. Org. Chem. 2000, 65, 5009-5013, Chem. Lett. 2003, 32, 222-223, US2003149069A1, but are not mentioned in connection with cancer treatments and/or do not contain the features essential to the invention.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which causes at least one of the following effects in a human or another mammal (compared with a subject who has not received this amount): improvement in the healing treatment, healing, prevention or elimination of a disease, syndrome, condition, complaint, disorder or side-effects or also the reduction in the progress of a disease, condition or disorder.

The term "therapeutically effective amount" also encompasses the amounts which are effective for increasing or enhancing normal physiological function.

The invention also relates to the use of mixtures of the compounds according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to the patent claims and pharmaceutically usable derivatives, salts, solvates and stereoisomers thereof, characterised in that a compound of the formula II

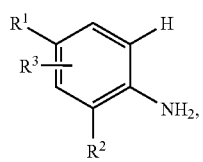

II in which $R^1$, $R^2$ and $R^3$ have the meanings indicated above, is reacted with a compound of the formula III

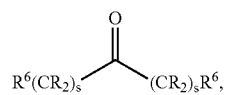

III in which $R^6$ and s have the meanings indicated above, and with a compound of the formula IV, the double-bond isomer (E isomer) thereof or mixtures thereof

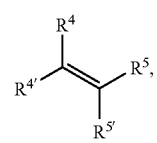

IV in which $R^4$, $R^{4'}$, $R^{5'}$ and $R^{5'}$ have the meanings indicated above, preferably in the presence of a protonic acid or Lewis acid, such as, for example, trifluoroacetic acid, hexafluoroisopropanol, bismuth(III) chloride, ytterbium(III) triflate, scandium(III) triflate or cerium(IV) ammonium nitrate, and a radical other than H is optionally introduced by conventional methods for $R^7$.

The mixtures of diastereomers and enantiomers of the compounds of the formula I which may be obtained by the process described above are preferably separated by chromatography or crystallisation.

If desired, the bases and acids of the formula I obtained by the process described above are converted into their salts.

In particular, the compounds according to the invention can be prepared analogously to the following schemes, where, in particular, the radical Q takes place by modification of an existing radical by known methods:

Scheme 1

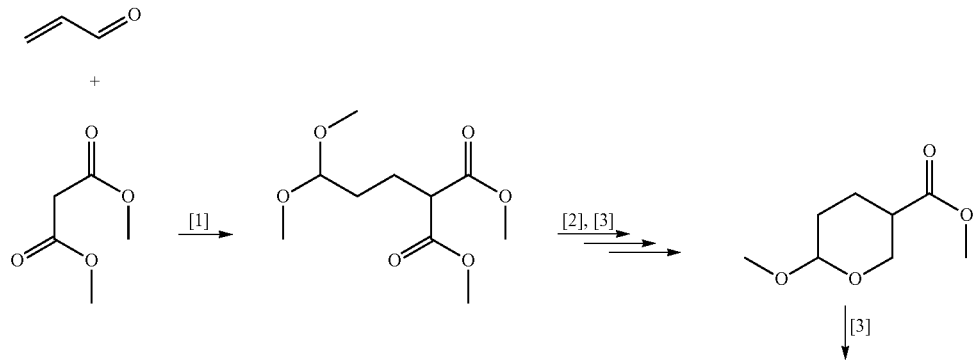

-continued
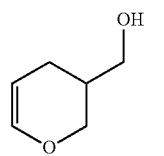 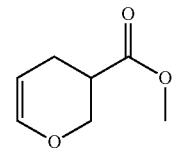
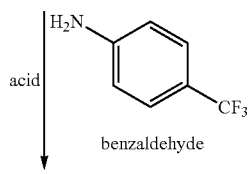 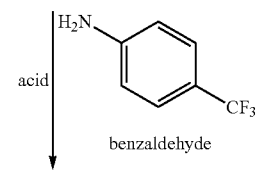
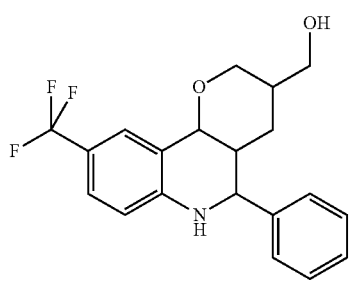 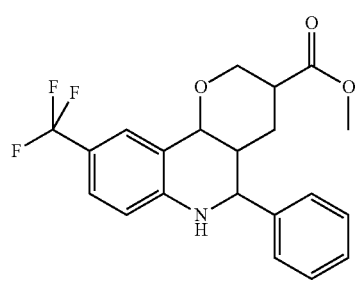
1. Mesylation
2. N(R¹)₂
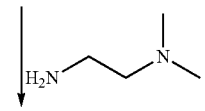
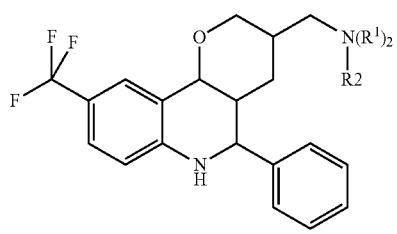 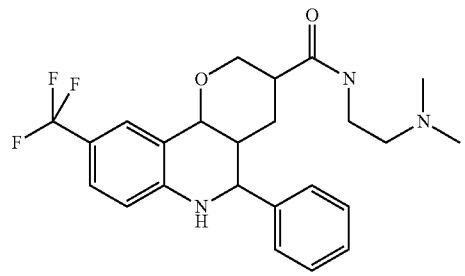
[1] H. K. Hall, L. J. Carr, R. Kellman, F. de Blauwe, J. Am. Chem. Soc. 1974, 96, 7265-7269.
[2] M. Okada, H. Sumitomo, M. Atsumi, H. K. Hall, R. B. Ortega, Macromolecules 1986, 19, 503-509.
[3] M. Okada, H. Sumitomo, T. Sassa, M. Takai, H. K. Hall, M. Bruck, Macromolecules 1990, 23, 2427-.

Scheme 2
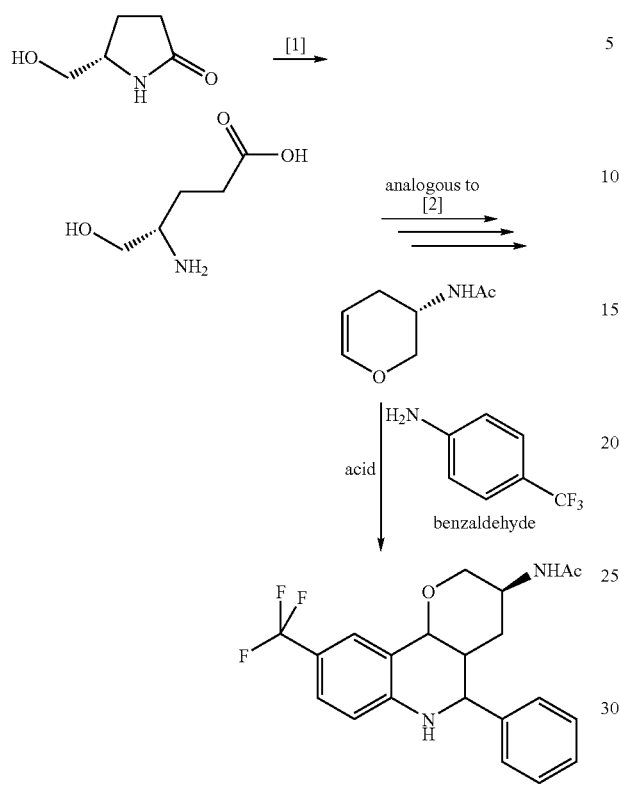
[1] Bruckner et al., Acta Chim. Acad. Sci. Hung. 1959, 21, 105, 116.
[2] Y. Suhara, F. Sasaki, G. Koyama, K. Maeda, H. Umezawa, M. Ohno, J. Am. Chem. Soc. 1972, 94, 6501-6507
Scheme 3
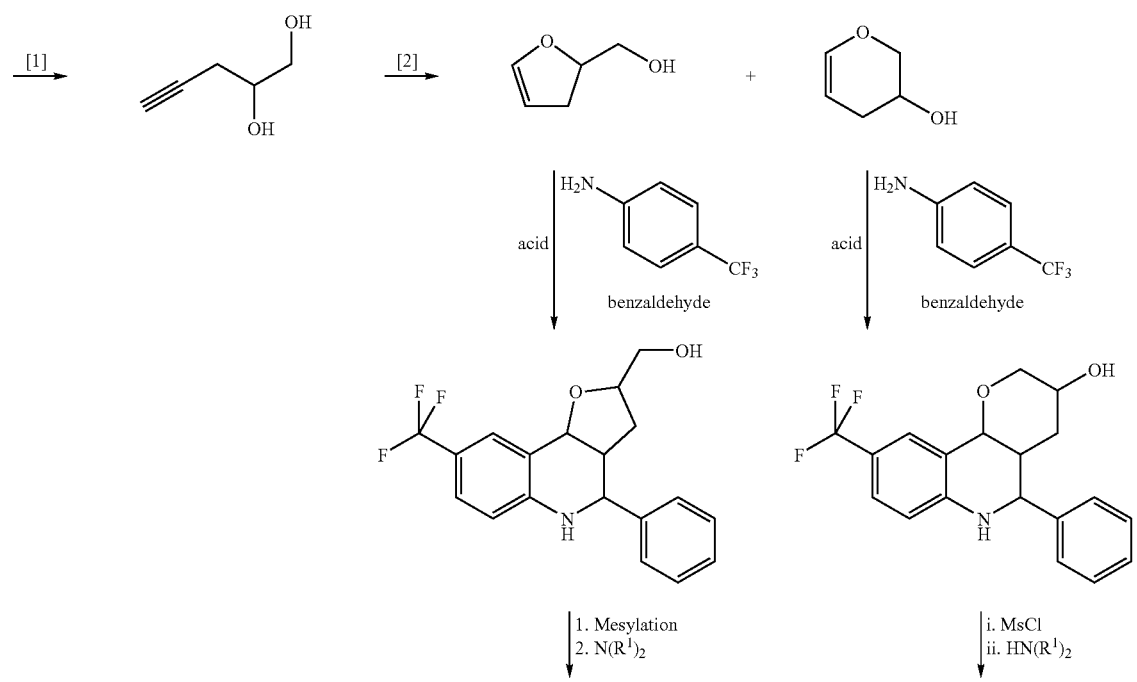

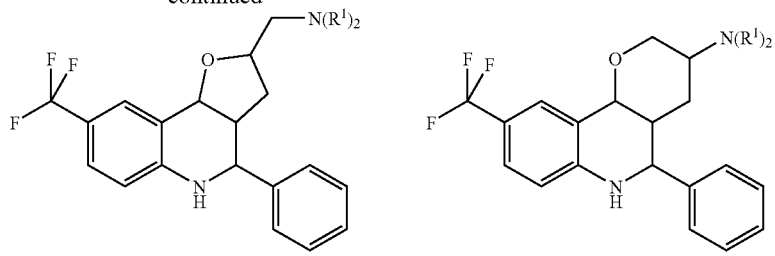
[1] e.g. Synthesis described in E.R.H. Jones, J.S. Stehpenson, W.B. Turner, M.C. Whiting, J. Chem. Soc. 1963, 2048-2055.
[2] F.E. McDonald, C.B. Connolly, M.M. Gleason, T.B. Towne, K.D. Treiber, J. Org. Chem. 1993, 58, 6952-6953.
Scheme 4
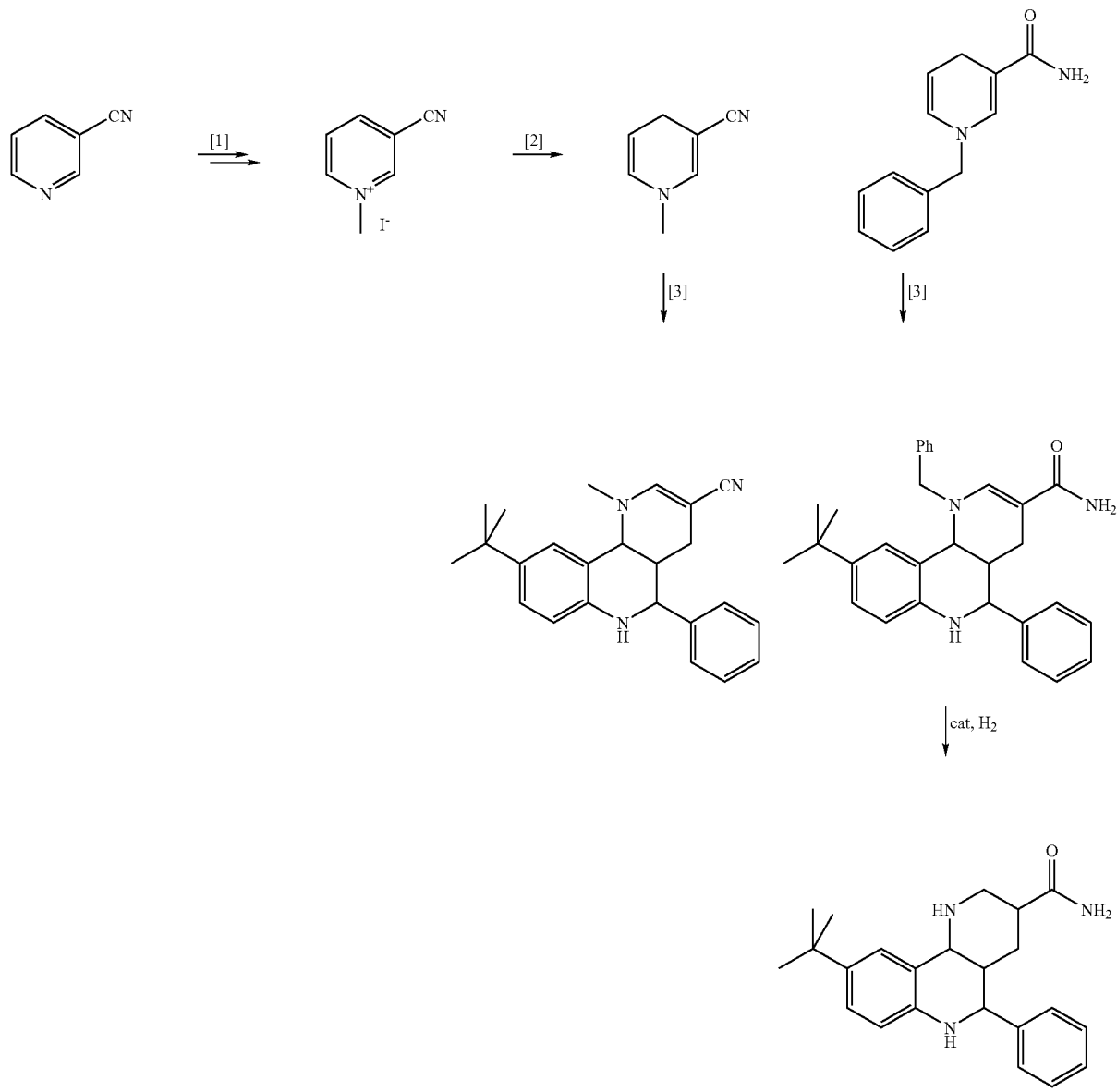
[1] M.R. Lamborg, R.M. Burton, N.O. Kaplan, J. Am. Chem. Soc. 1957, 79, 6173-6177.
[2] P. Karrer, F. Blumer, Helv. Chim. Acta 1947, 30, 1157.
[3] I. Carranco, J.L. Diaz, O. Jimenez, M. Vendrell, F. Albericio, M. Royo, R. Lavilla, J. Comb. Chem. 2005, 7, 33-41.

Scheme 5
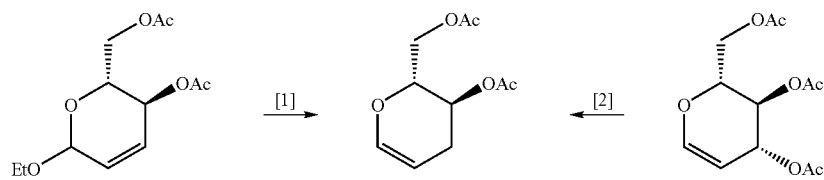
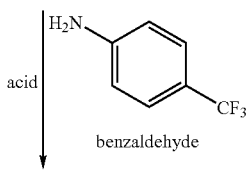
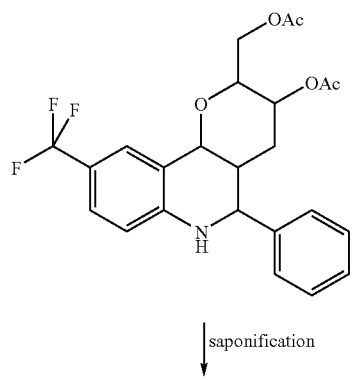
saponification
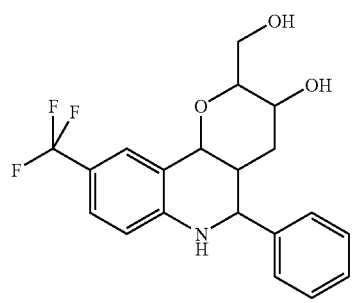
[1] B. Fraser-reid, B. Radatus, J. Am. Chem. Soc. 1970, 92, 6661-6663.
[2] N. Greenspoon, E. Keinan, J. Org. Chem. 1988, 53, 3723-3731.

Scheme 6

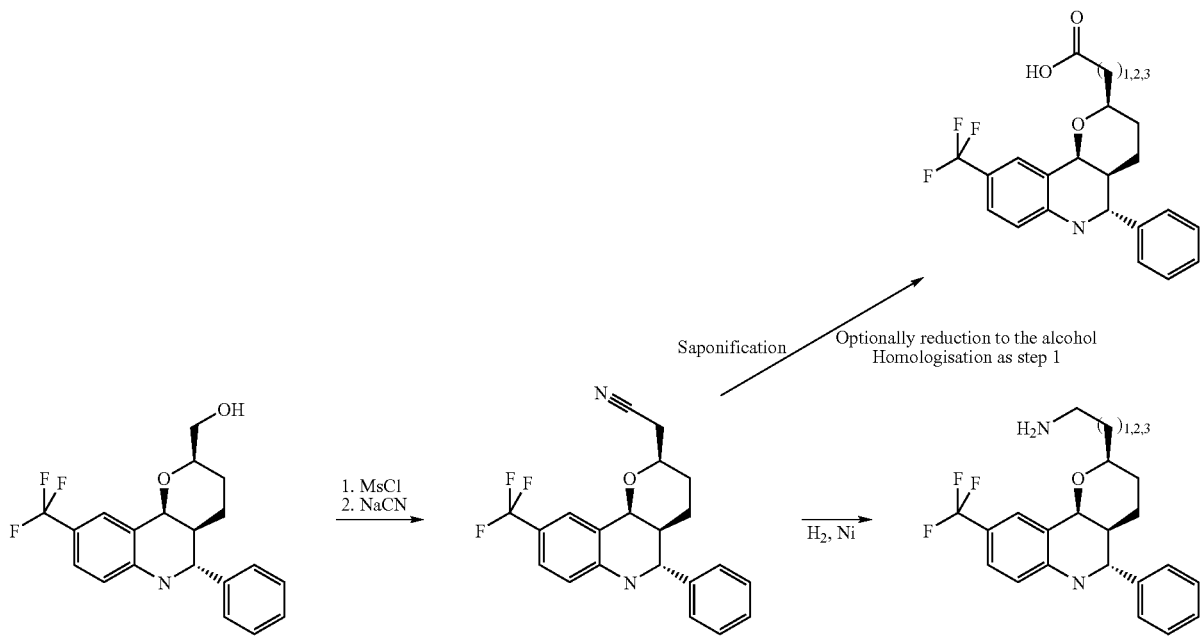

Above and below, the radicals R, R¹, R², R³, R⁴, R⁴', R⁵, R⁵', R⁶, R⁶', R⁷, X, Y, E, Q, R^a, Z, W, m, n, p and S have the meanings indicated for the formula I, unless expressly indicated otherwise. If individual radicals occur a number of times within a compound, the radicals adopt the meanings indicated, independently of one another.

If individual indices occur more than once within a compound or radical, the indices preferably, independently of one another, adopt the meanings indicated, unless expressly indicated otherwise. Thus, for example, the indices p in the radicals Q in which they occur more than once are preferably in each case selected, independently of one another, from the meanings indicated above and/or below, unless expressly indicated otherwise.

A denotes alkyl, is preferably unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A also denotes cycloalkyl.

Cycloalkyl preferably denotes cyclopropyl, cyclobutyl, cyclopentyl, cyclohexyl or cycloheptyl, but in particular cyclopentyl.

E is preferably —NR¹SO₂—, —SO₂NR¹—, —CONR¹—, —NR¹CO—, —NR¹—CO—NR¹— or —OCONR¹—. E is particularly preferably —NR¹CONR¹—.

R¹ preferably denotes A, CF₃, OCF₃, SA, SCN, CH₂CN, —OCOA, Hal, SCF₃, preferably also t-butyl, —CH(CH₃) CH₂CH₃, isopropyl, ethyl or methyl. In particular, R¹ denotes t-butyl, isopropyl, ethyl, CF₃, methyl, Br, Cl, SCF₃, CH(CH₃) CH₂CH₃, n-propyl, OCH₃, SCH₃, n-butyl, —SCN, CH₂CN. R¹ particularly preferably denotes t-butyl or CF₃.

R² preferably denotes Hal, A or OA, in particular Br, cyclopropyl, OCH₃.

Particular preference is furthermore given to H or F.

R³ preferably denotes H or A, in particular H. R³ is preferably in the 5-position. In particular, R³ denotes H or F.

In particularly preferred compounds of the formula I, R² and R³ simultaneously have the meaning H. In further preferred compounds of the formula I, one of the radicals R² and R³ has the meaning H and the other radical has the meaning F.

R⁴ preferably denotes one of the following groups if R⁵ denotes H:

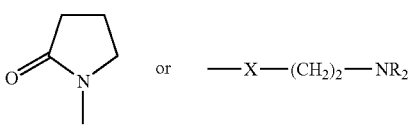

R⁵ preferably denotes H or, together with R⁴, adopts one of the following meanings:

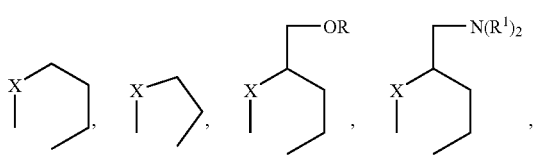

-continued

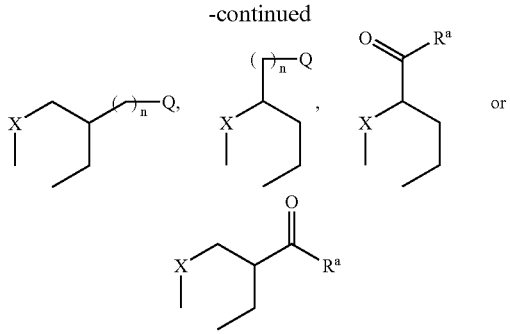

in which n, X, R and $R^a$ have the meaning indicated above.

$R^4$ together with $R^5$ particularly adopts one of the following meanings:

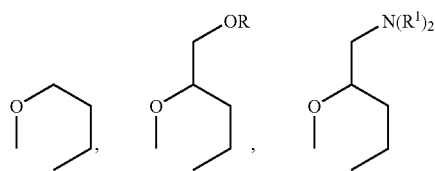

in which R has the meaning indicated above and $N(R^1)_2$ preferably denotes NHR, in particular $NHCH_3$, $NH(CH_2)_3OR^1$, $NR(CH_2)_3OR^1$, $NHSO_2R^1$, $NRSO_2R^1$, $NHSO_2(CH_2)_3NHR$ or $NRSO_2(CH_2)_3NHR$, where $NR(CH_2)_3OR^1$ preferably stands for $NA(CH_2)_3OR^1$, $NRSO_2R^1$ preferably stands for $NASO_2R^1$, and $NRSO_2(CH_2)_3NHR$ preferably stands for $NASO_2(CH_2)_3NHR$. In $NA(CH_2)_3OR^1$, $NASO_2R^1$ and $NASO_2(CH_2)_3NHR$, A preferably stands for H or alkyl, particularly preferably for alkyl and in particular for methyl or ethyl. In $NASO_2R^1$, $R^1$ preferably stands for alkyl, particularly preferably for $CH_2Hal$, $(CH_2)_2Hal$ or $(CH_2)_3Hal$ and in particular for $CH_2Cl$, $(CH_2)_2Cl$ or $(CH_2)_3Cl$.

$R^4$ together with $R^5$ very particularly preferably adopts one of the following meanings:

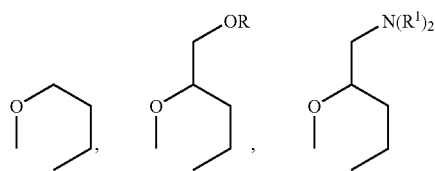

in which R has the meaning indicated above, and $N(R^1)_2$ preferably denotes NHR, in particular $NHCH_3$, $NH(CH_2)_3OR^1$ or $NHSO_2(CH_2)_3NHR$.

$R^{4'}$, $R^{5'}$ and $R^{6'}$ preferably denote A or H. Particularly preferably, only one of the radicals denotes A, while the others denote H. In particular, the radicals also simultaneously denote H.

5- and 6-membered ring systems are preferred. 6-membered ring systems are particularly preferred.

$R^a$ preferably denotes 1-piperazinyl, N-morpholinyl, NHR or $NR_2$.

$R^6$ preferably denotes phenyl, 2-, 3- or 4-pyridyl, pyrimidyl, furyl or thienyl, each of which is unsubstituted or mono- or polysubstituted by Hal, CN, $NO_2$, OH, $CF_3$, $OCH(CF_3)_2$, $OCOCH_3$ or A. $R^6$ is preferably not a heteroaromatic radical. In particular, $R^6$ denotes one of the following groups:

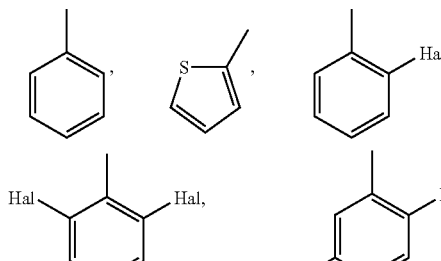

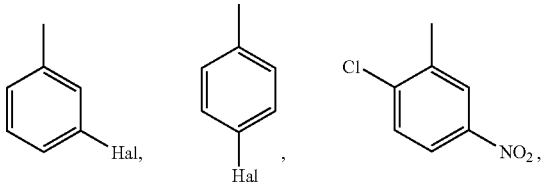

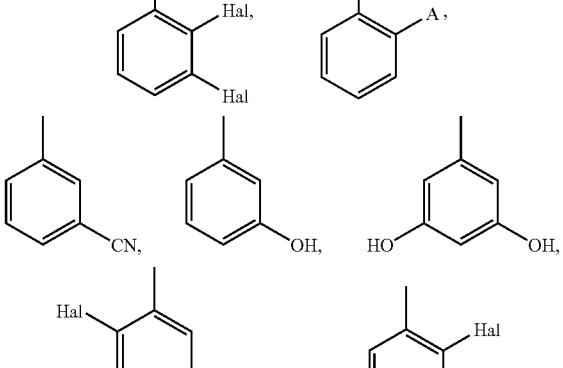

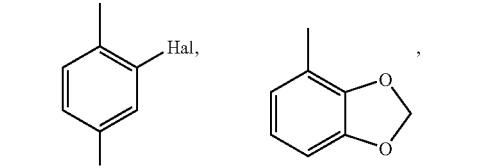

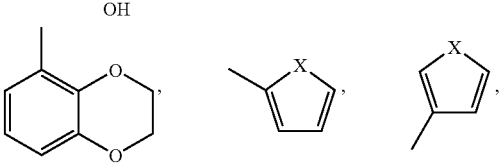

or

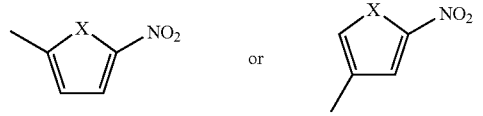

in which

X denotes O, S or NR and in particular O or S, A has the meaning indicated above, but preferably denotes methyl, and Hal preferably denotes F or Cl.

Particular preference is furthermore given to compounds of the formula I in which $R^6$ has one of the following meanings:

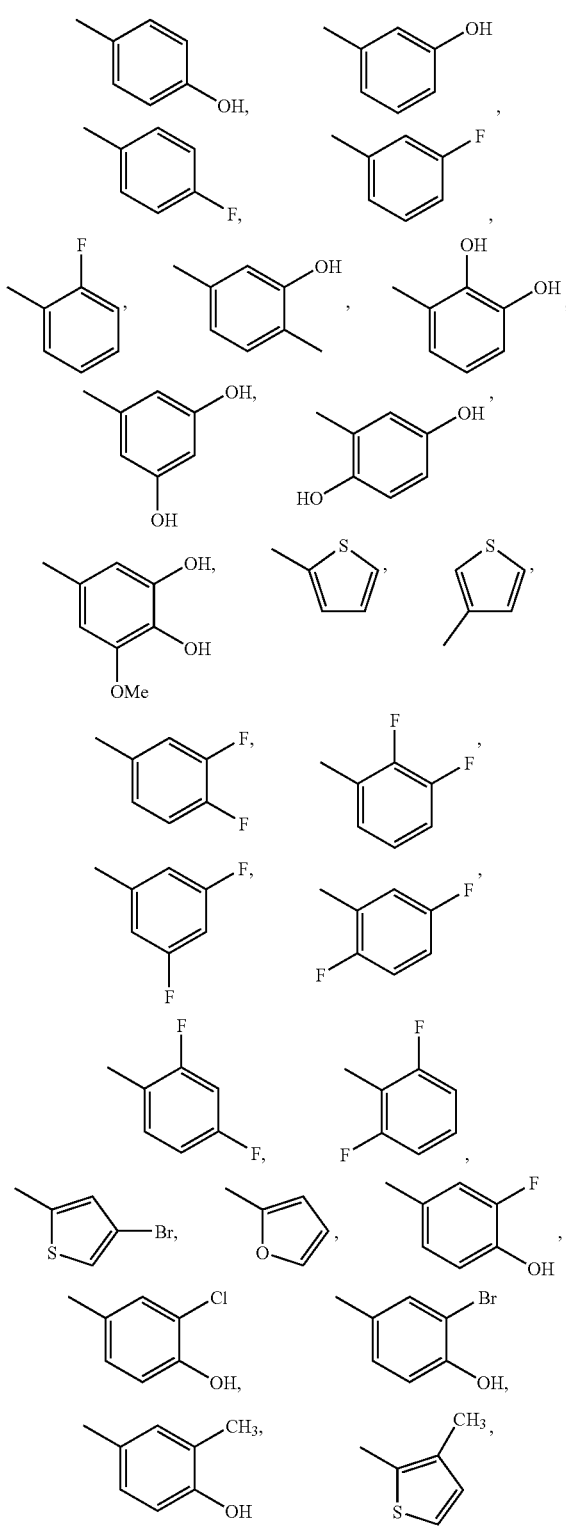

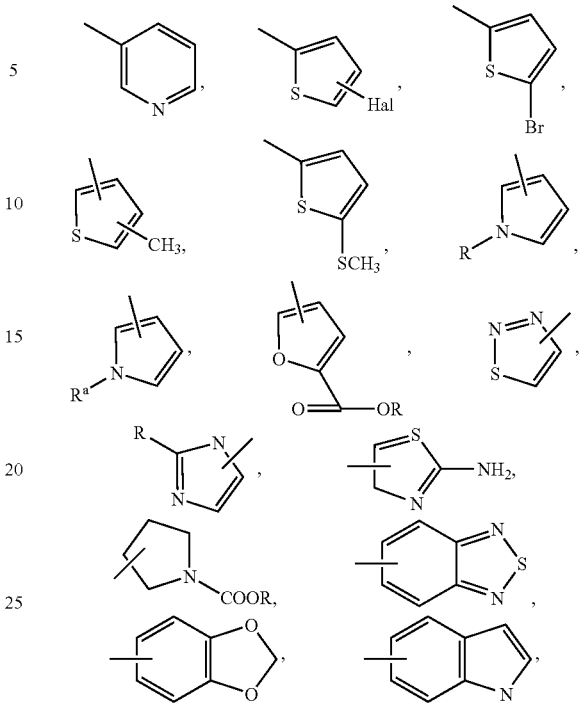

$R^7$ preferably denotes H or A, in particular H.

Aryl preferably denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH.

Aryl preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p- chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Heteroaryl preferably denotes a mono- or bicyclic aromatic heterocycle having one or more N, O and/or S atoms which is unsubstituted or mono-, di- or trisubstituted by Hal, A, NO$_2$, NHA, NA$_2$, OA, COOA or CN.

Heteroaryl particularly preferably denotes a monocyclic saturated or aromatic heterocycle having one N, S or O atom, which may be unsubstituted or mono-, di- or trisubstituted by Hal, A, NHA, NA$_2$, NO$_2$, COOA or benzyl.

Irrespective of further substitutions, unsubstituted heteroaryl denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

Hal preferably denotes F, Cl or Br, but also 1, particularly preferably F or Cl.

Throughout the invention, all radicals which occur more than once may be identical or different, i.e. are independent of one another.

The compounds of the formula I can have one or more chiral centres and therefore exist in various stereoisomeric forms. The formula I encompasses all these forms.

Particularly preferred compounds of the formula I are those of the sub-formulae IA to ID:

IA

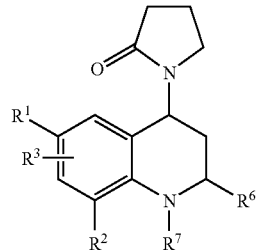

IB

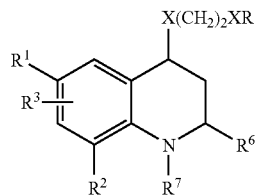

IC

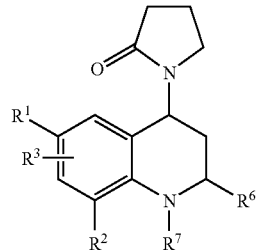

ID

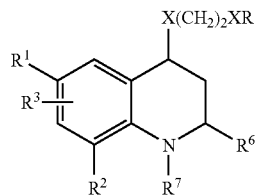

in which

R, R$^1$, R$^2$, R$^6$, R$^7$ and X have the meanings indicated above and

R$^8$ preferably denotes Q and in particular H, CH$_2$OR, CH$_2$NR$_2$, CH$_2$R$^a$, COR$^a$, (CH$_2$)$_p$-E-(CH$_2$)$_2$R$^1$, (CH$_2$)$_n$-E-(CH$_2$)$_p$—R$^a$.

Particularly preferred compounds of the formula IA are those of the sub-formulae IA0 to IA5:

IA0

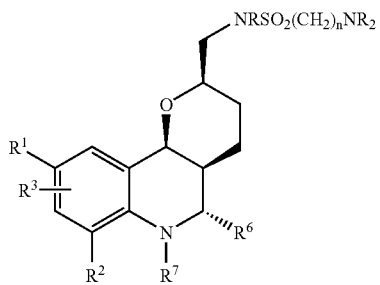

IA1

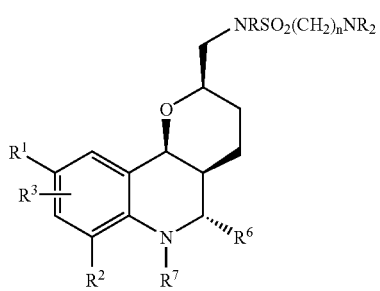

-continued

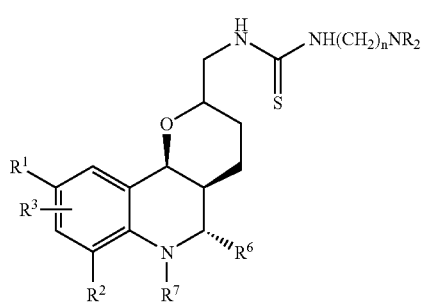
IA2

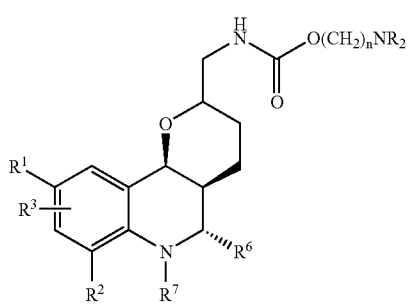
IA3

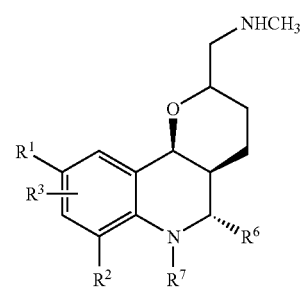
IA4

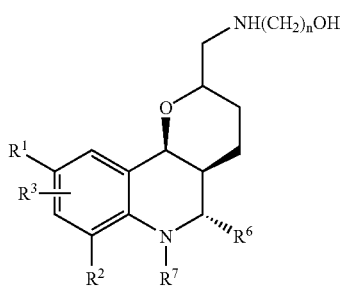
IA5 in which R, $R^a$, $R^1$, $R^2$, $R^3$, $R^6$ and $R^7$ have the meanings indicated above.

In particularly preferred compounds of the formula IB, $R^8$ has the meaning H.

The radicals $R^4$ and $R^5$ are particularly preferably in the cis-position to one another. The radical $R^6$ is furthermore preferably in the trans-position to the radical $R^5$.

Preference is given here to a compound of the formula A or B having the following structure:

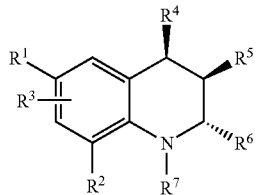
A

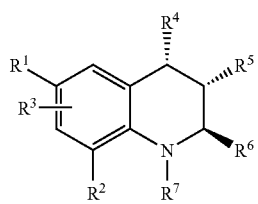
B and the racemate thereof or other mixtures of the enantiomers.

Accordingly, the invention relates, in particular, to the compounds of the formula I in which at least one of the said radicals has one of the preferred meanings indicated above. Some preferred groups of compounds may be expressed by the following sub-formulae I1 to I505:

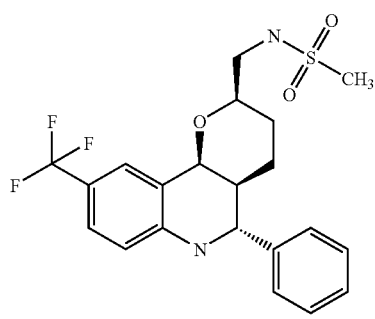
I1

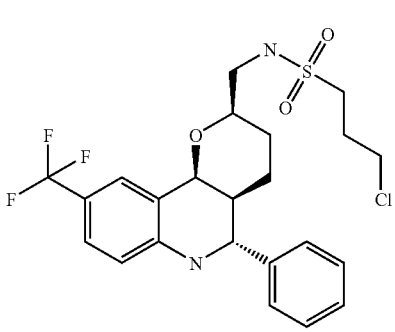
I2

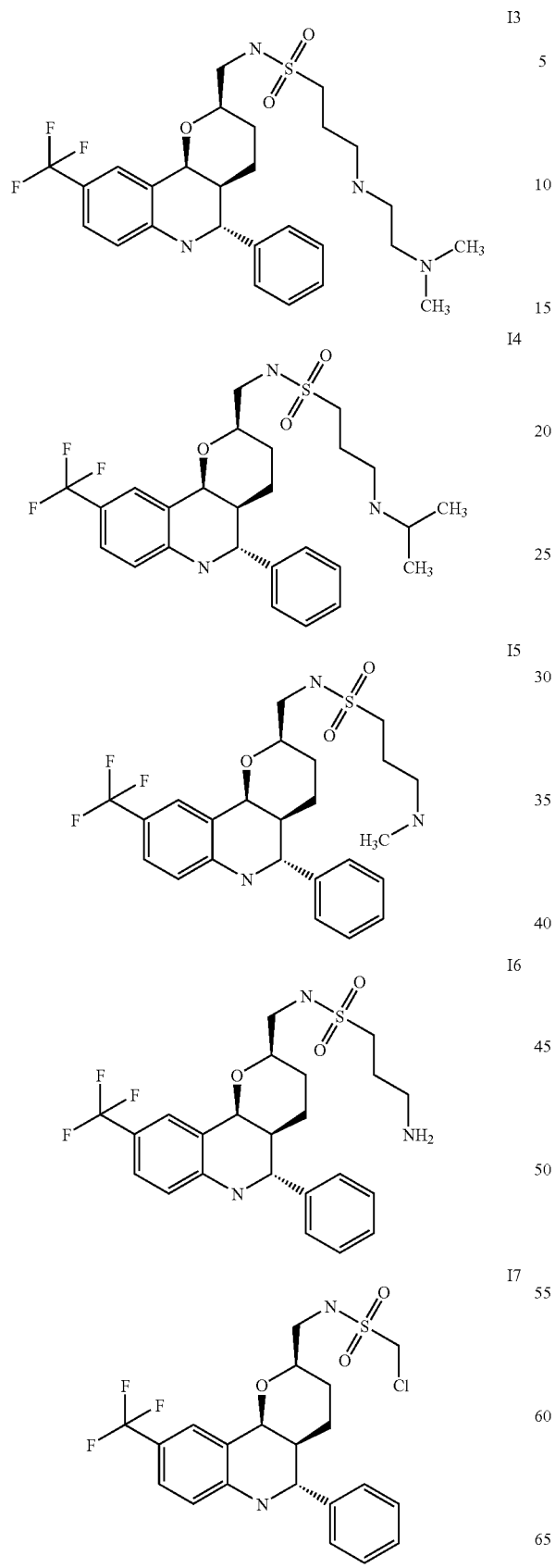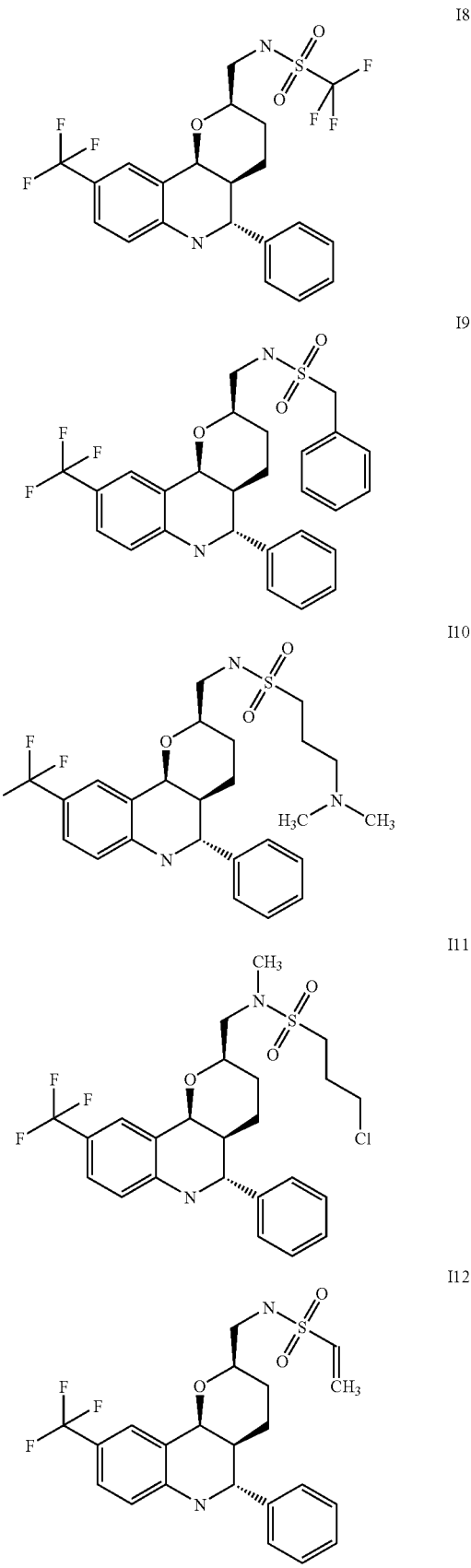

I13
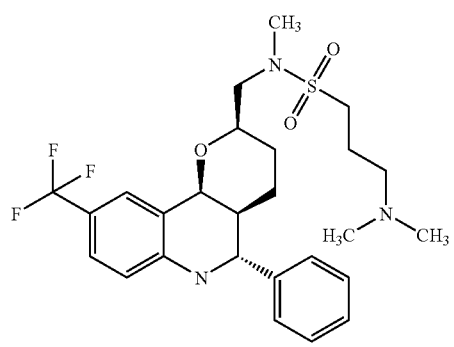
I14
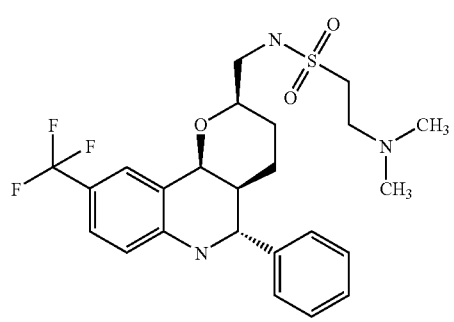
I15
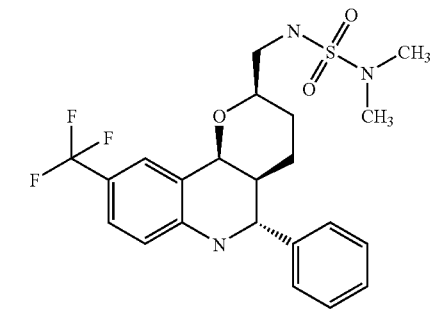
I16
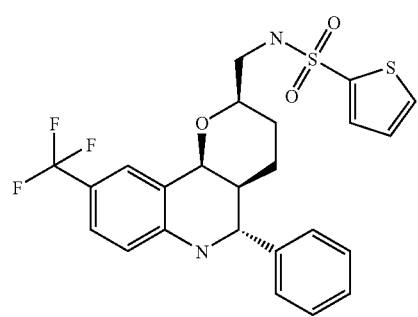
I17
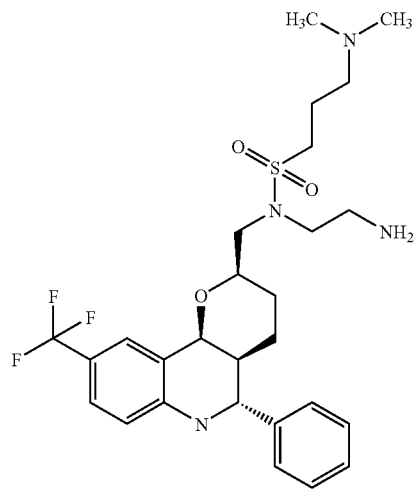
I18
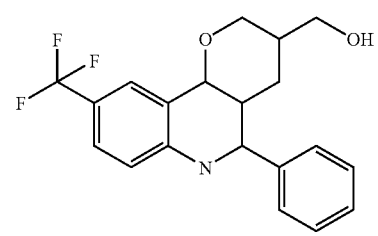
I19
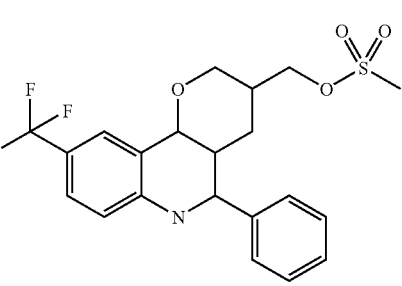
I20
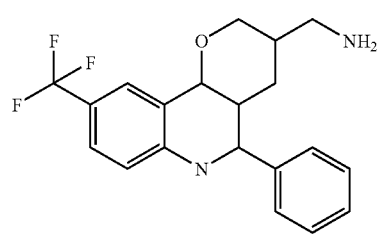
I21
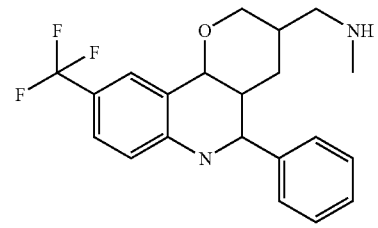

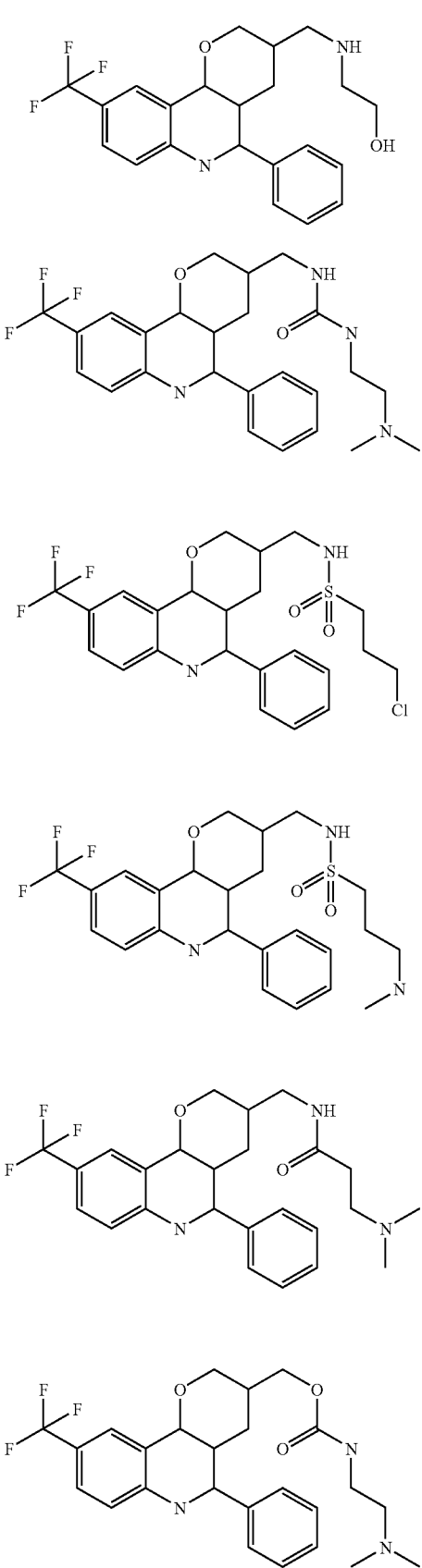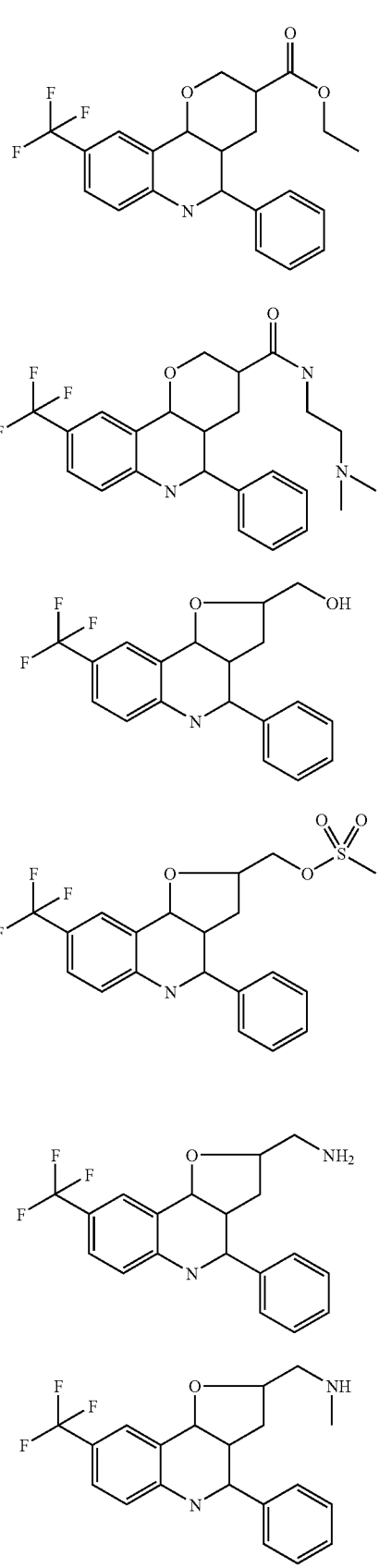

-continued
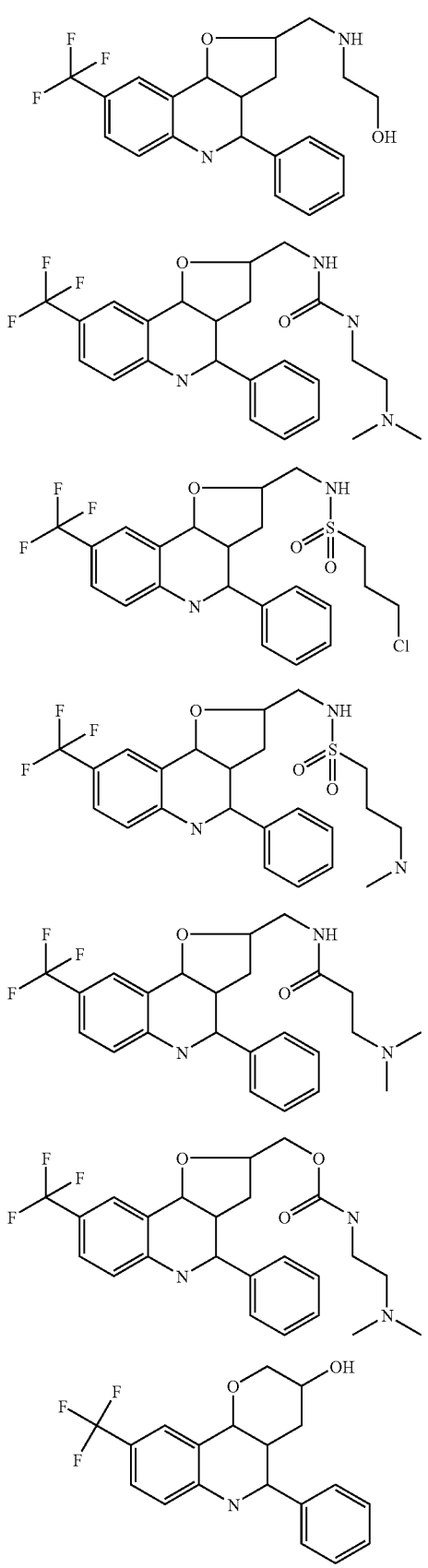
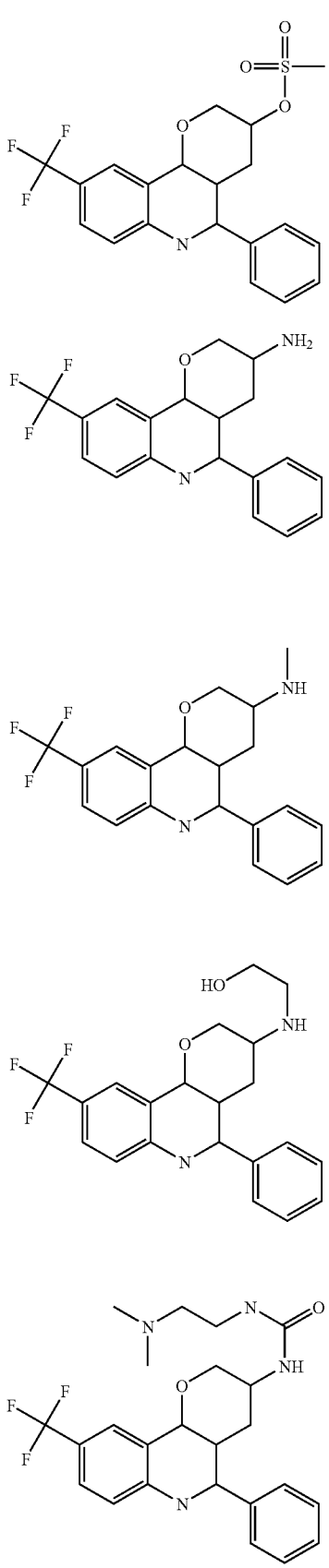

-continued
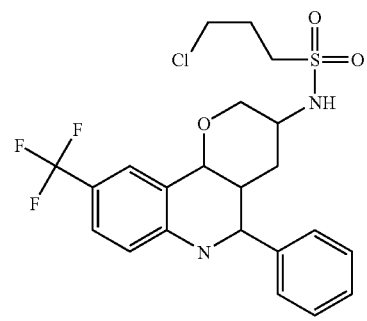 I46
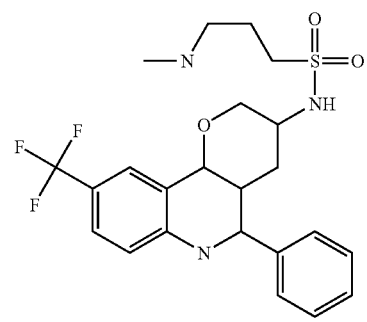 I47
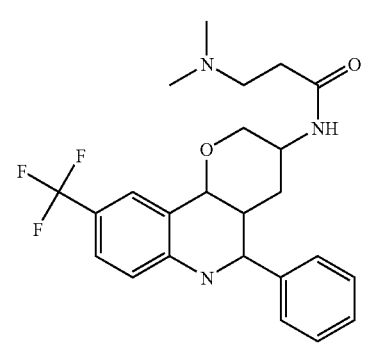 I48
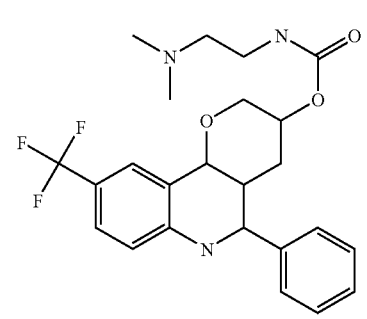 I49
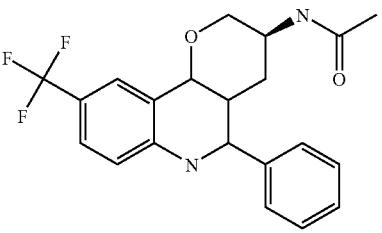 I50
-continued
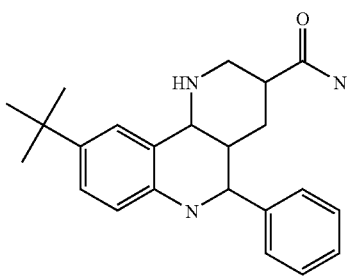 I51
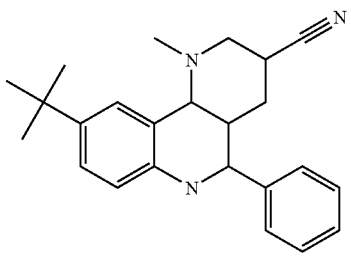 I52
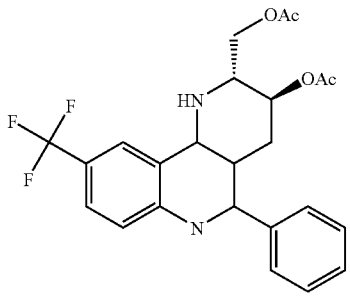 I53
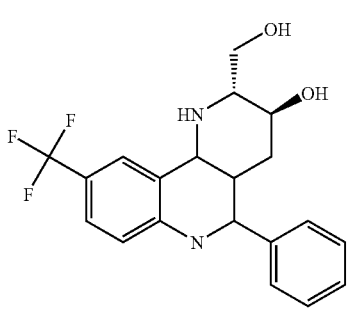 I54
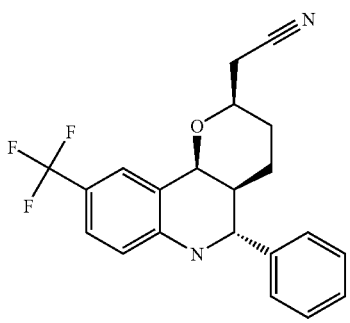 I55

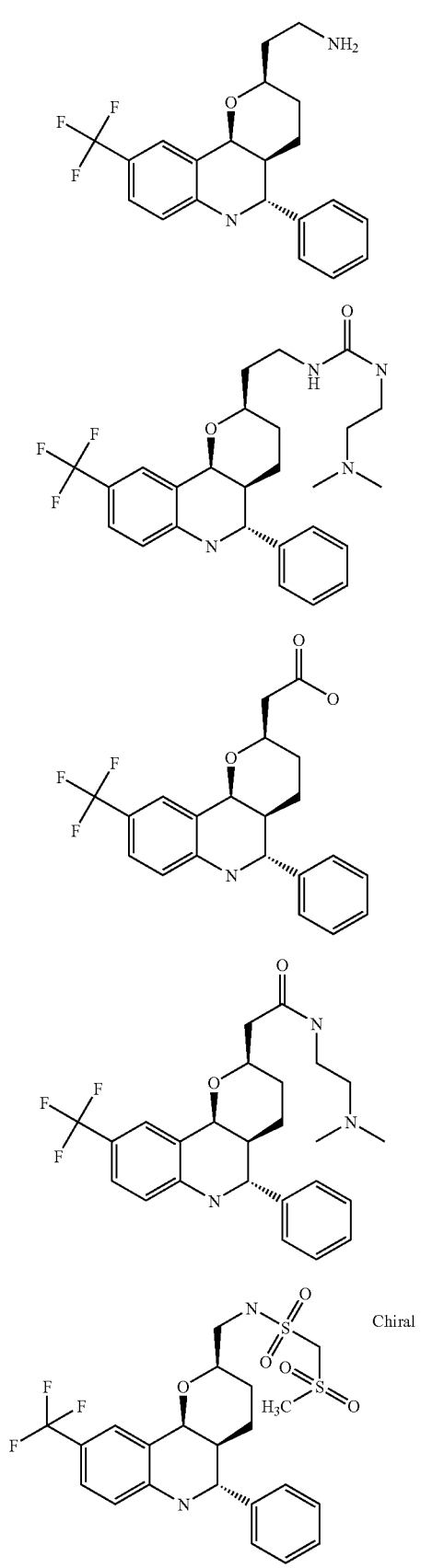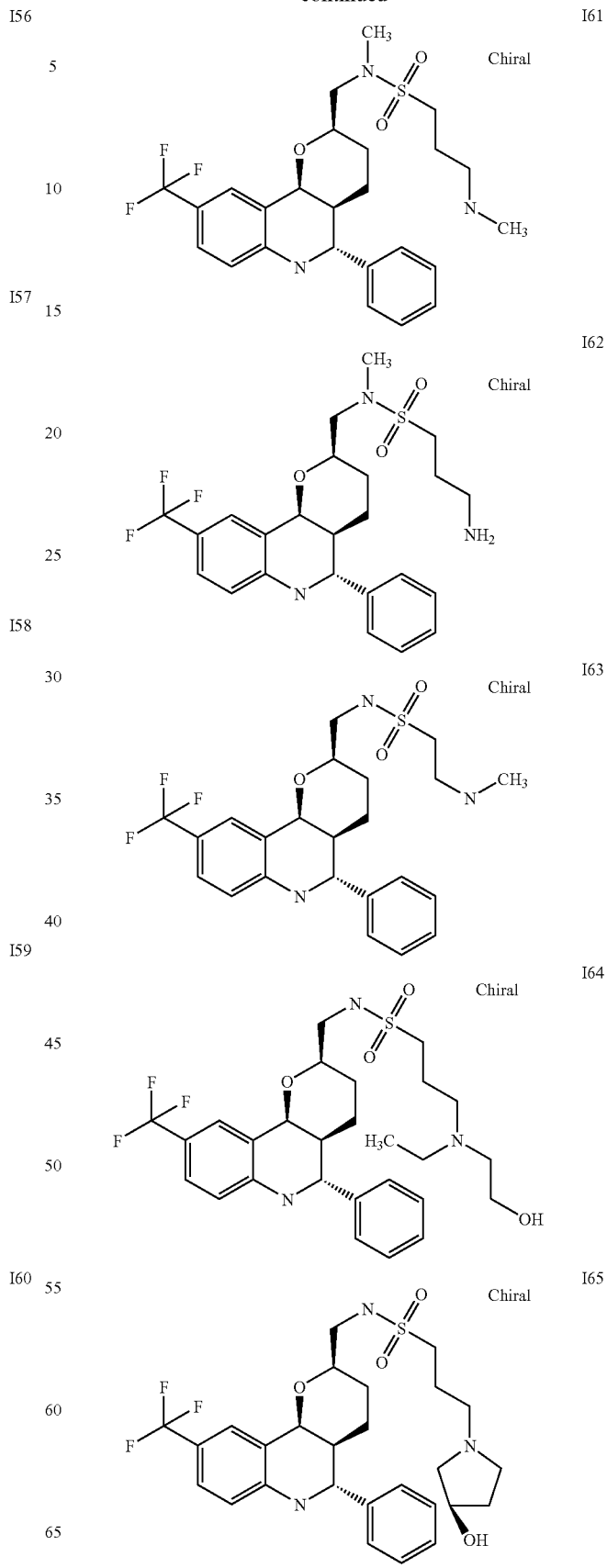

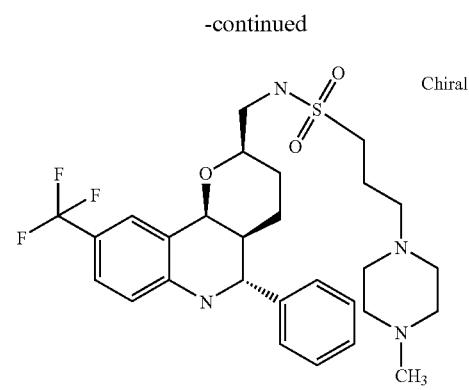
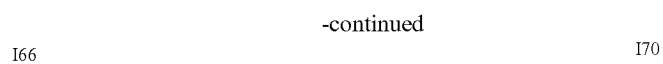
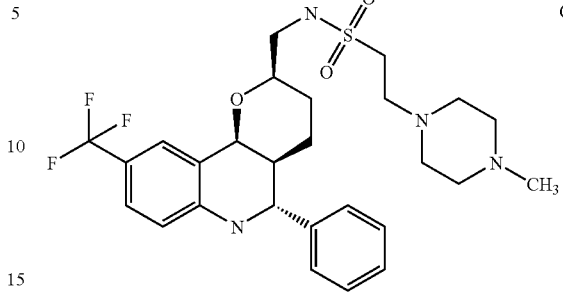
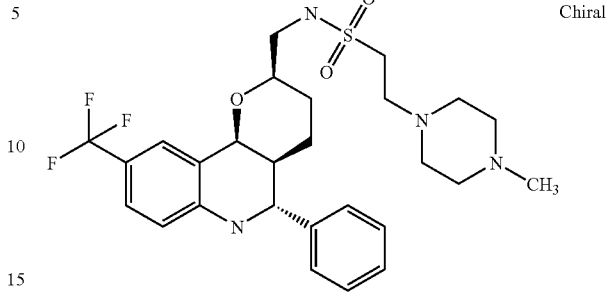
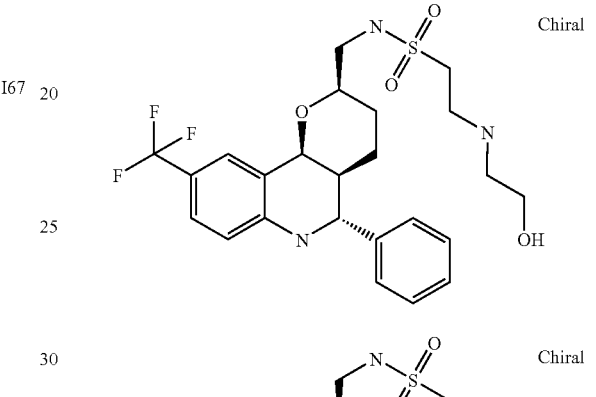
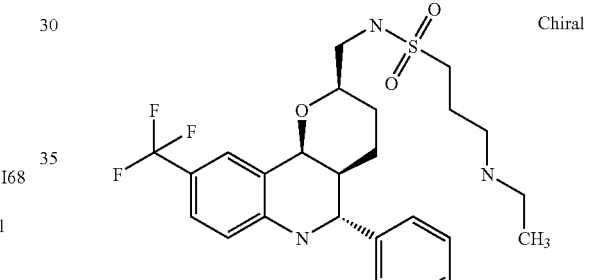
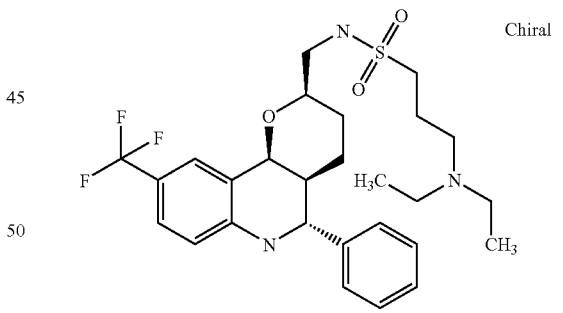
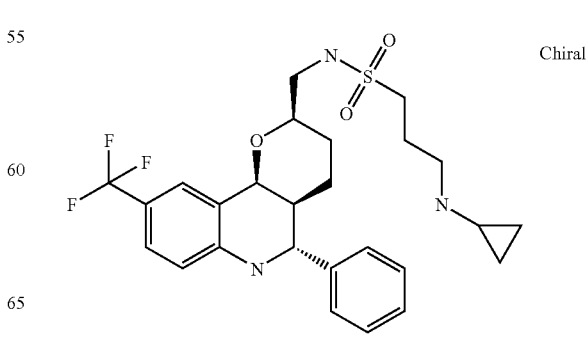

I75
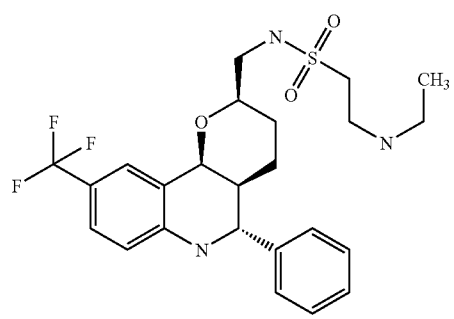
I76
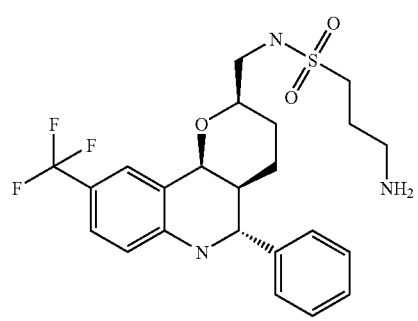
I77
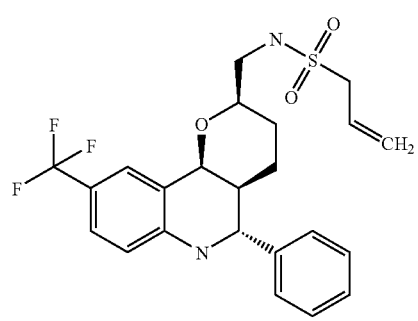
I78
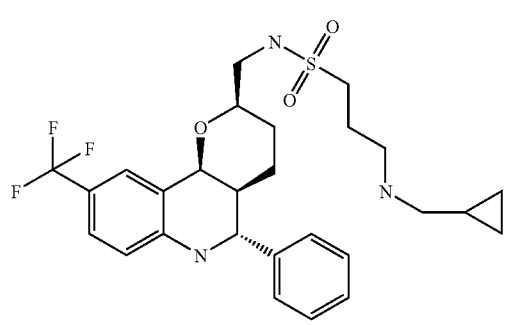
I79
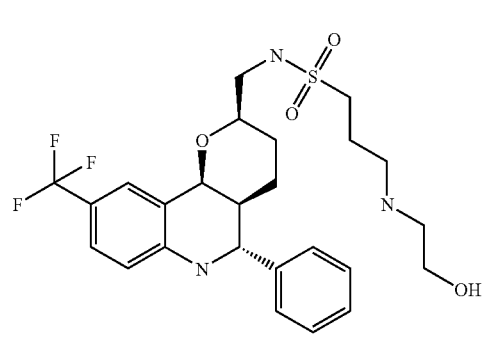
I80
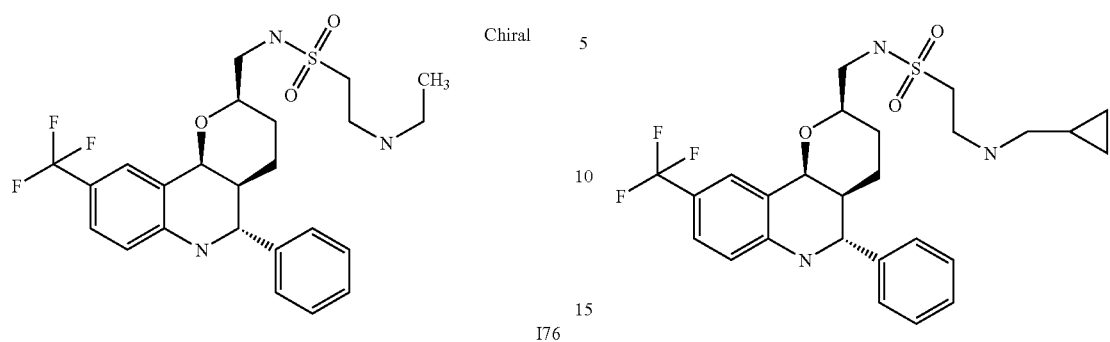
I81
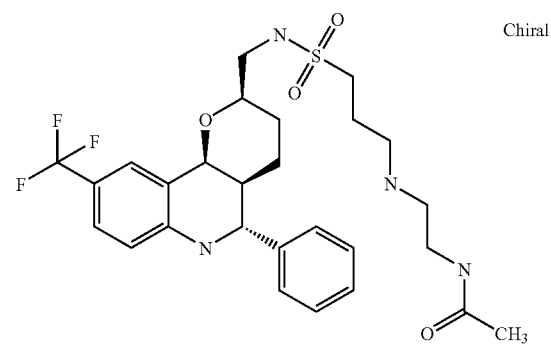
I82
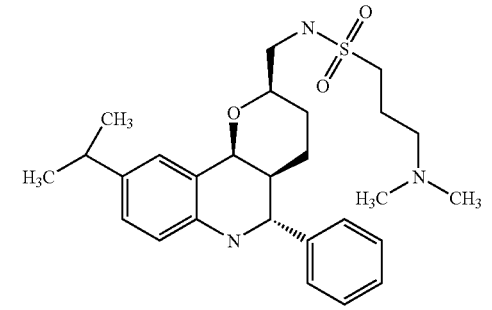
I83
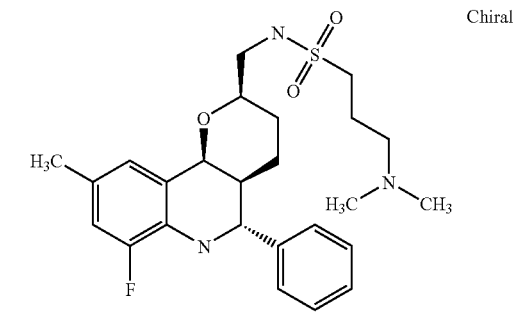

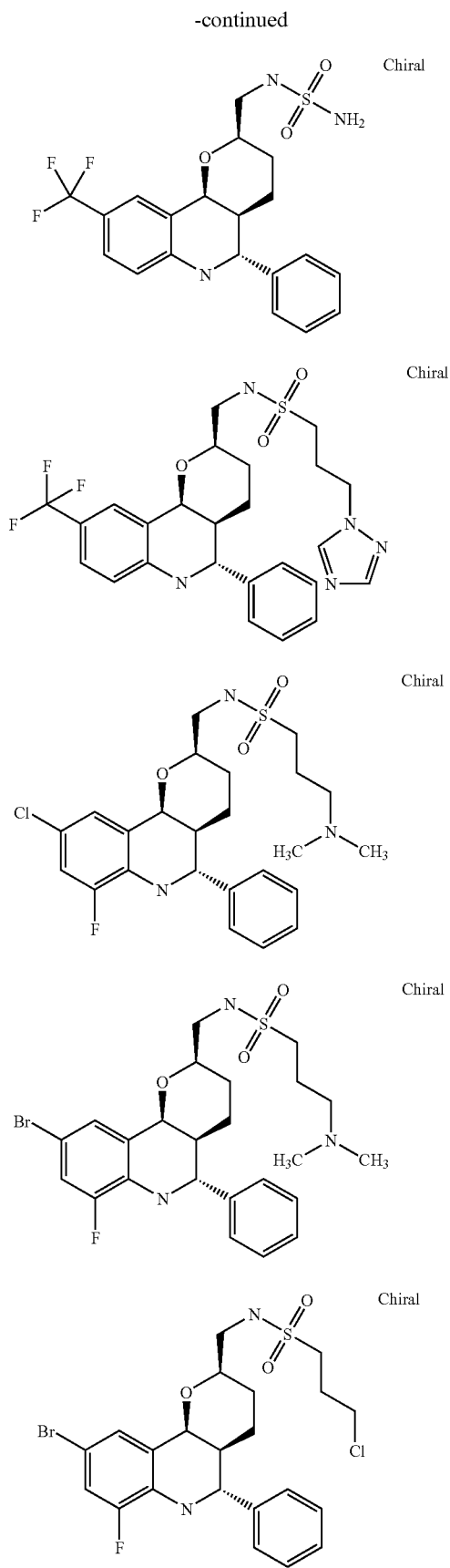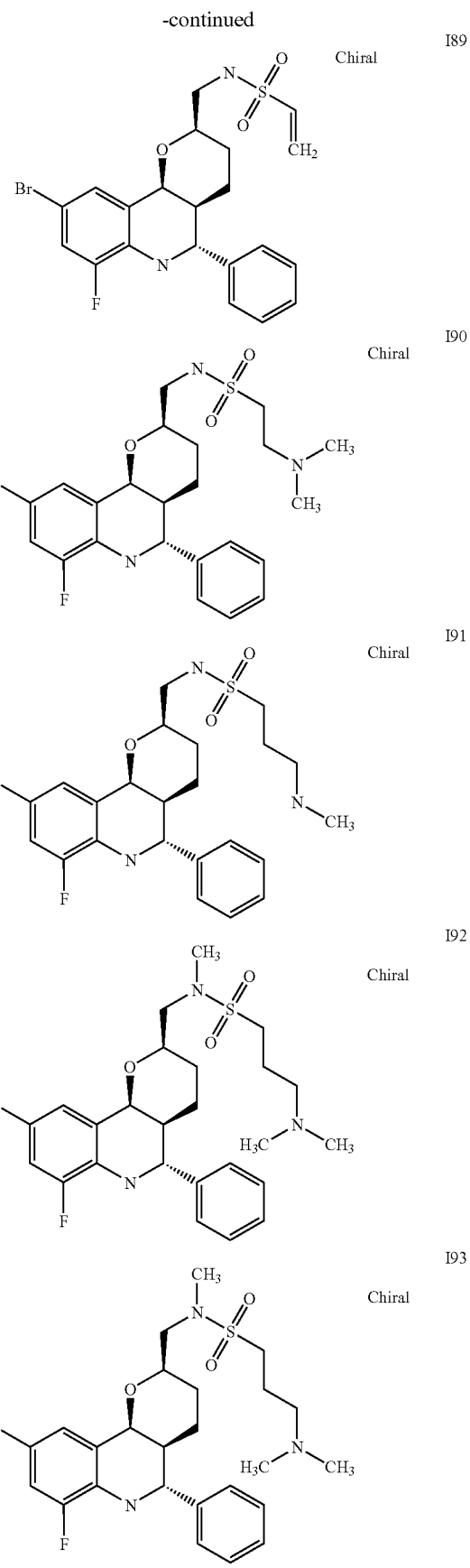

-continued
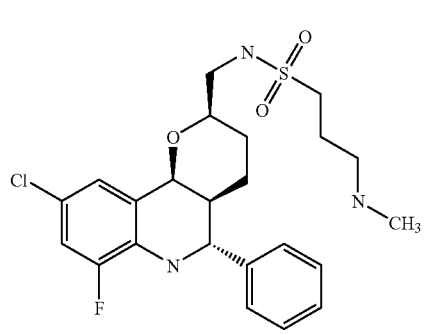 I94 Chiral
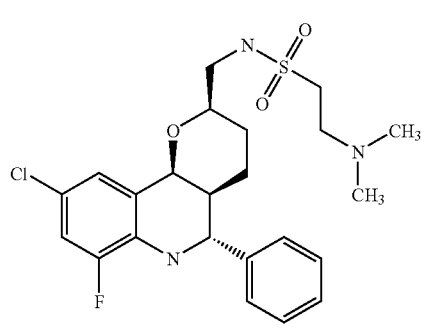 I95 Chiral
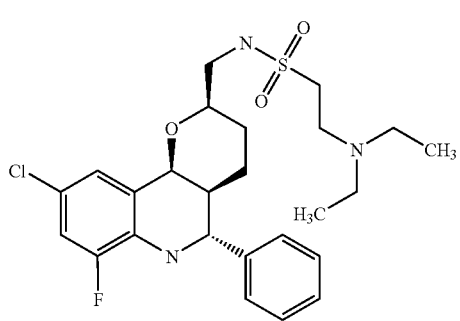 I96 Chiral
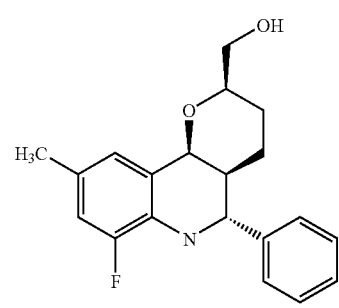 I97
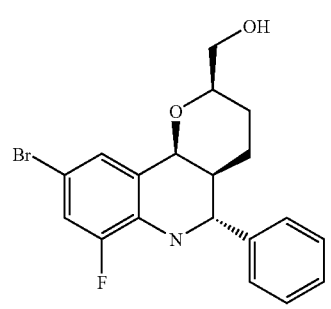 I98
-continued
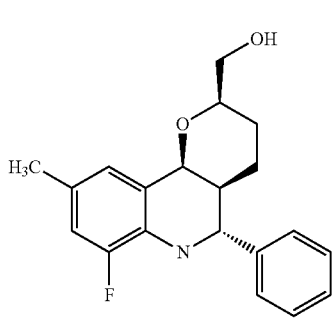 I99 Chiral
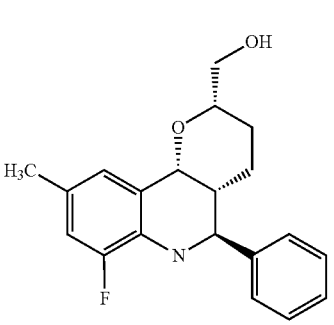 I100 Chiral
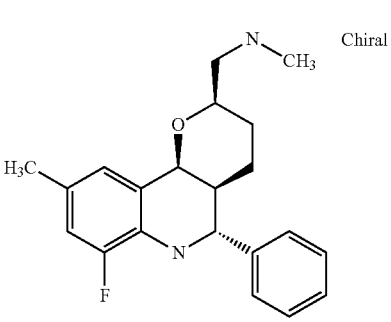 I101 Chiral
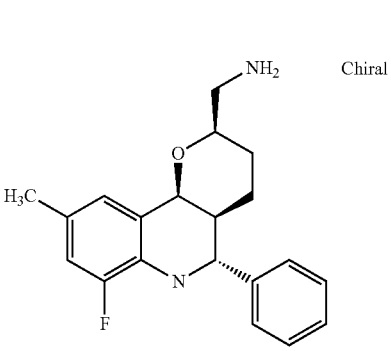 I102 Chiral
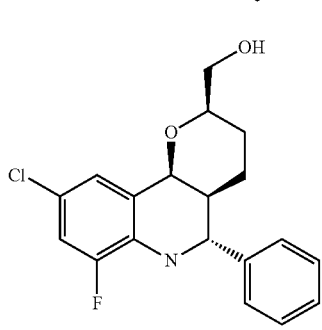 I103

-continued
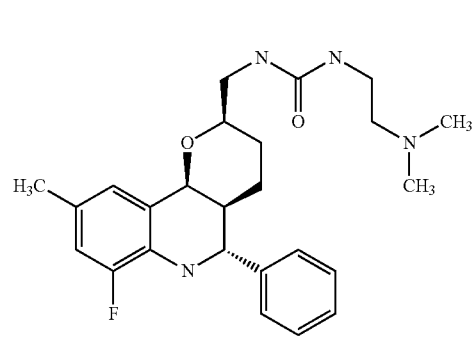
I104 Chiral
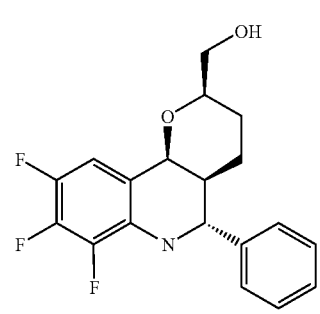
I105
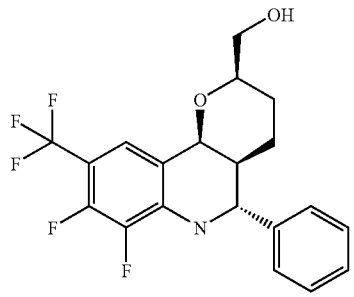
I106
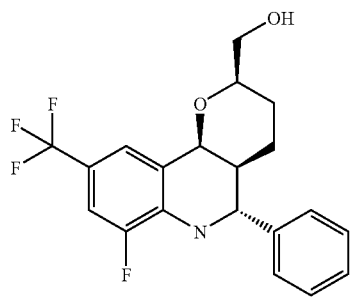
I107
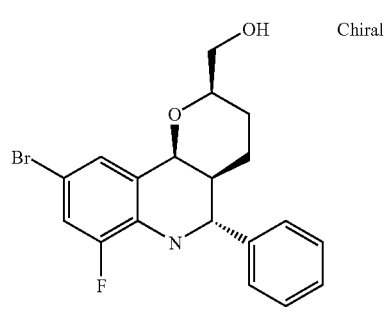
I108 Chiral
-continued
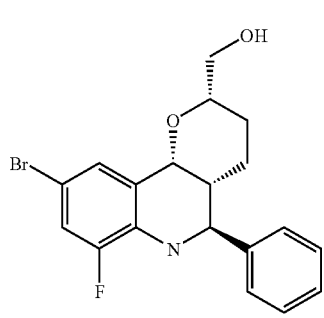
I109 Chiral
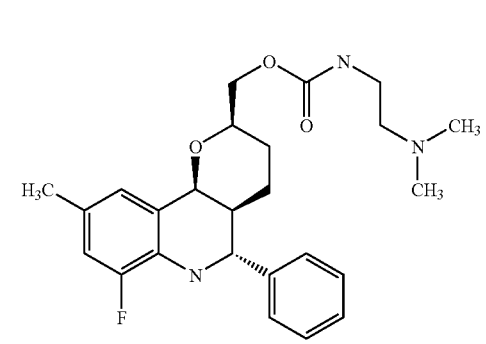
I110 Chiral
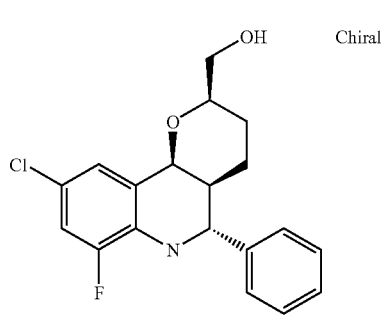
I111 Chiral
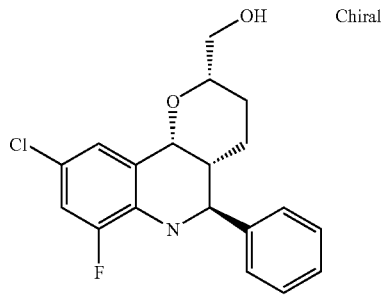
I112 Chiral
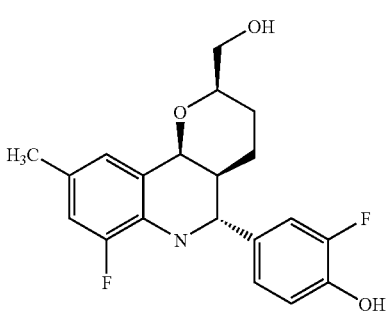
I113

-continued
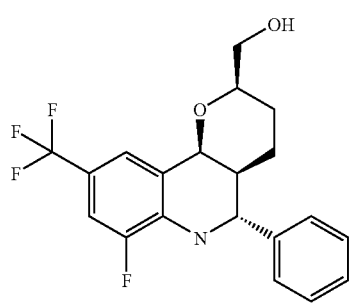 I114 Chiral
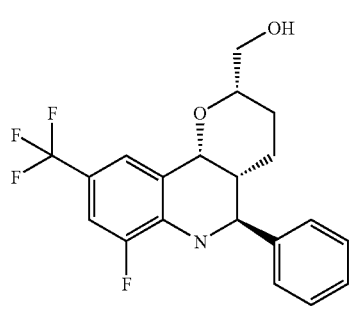 I115 Chiral
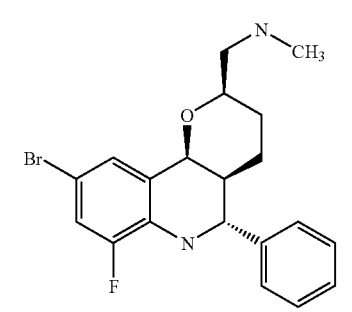 I116 Chiral
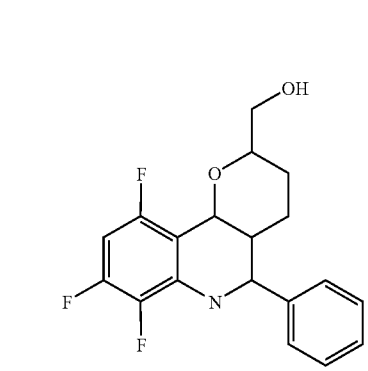 I117
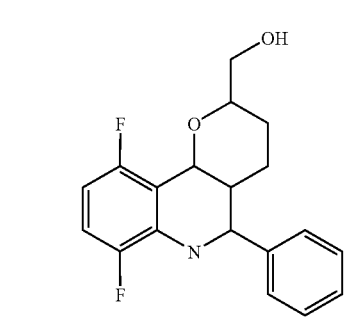 I118
-continued
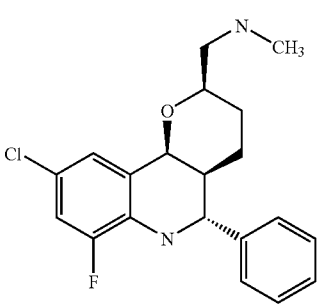 I119 Chiral
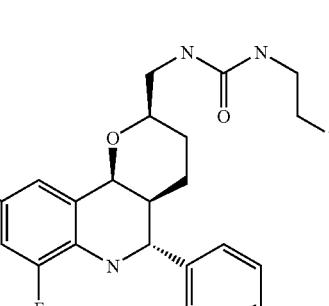 I120 Chiral
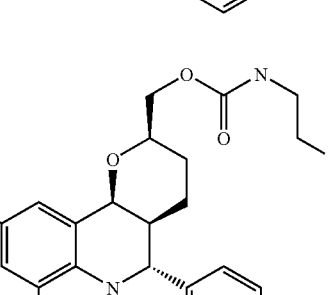 I121 Chiral
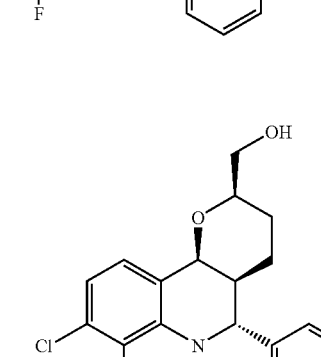 I122
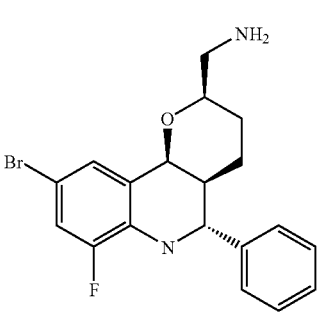 I123 Chiral -continued
I124
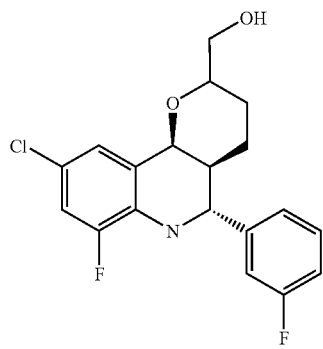
I125
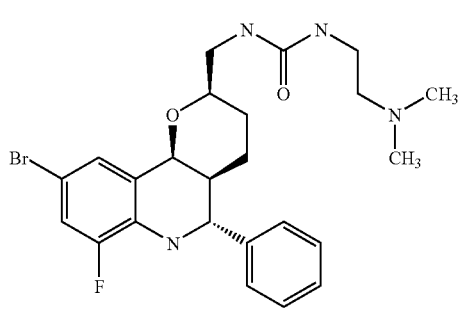
Chiral
I126
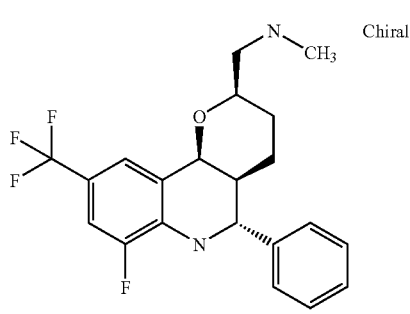
Chiral
I127
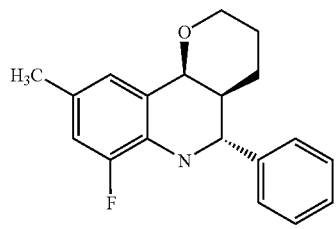
I128
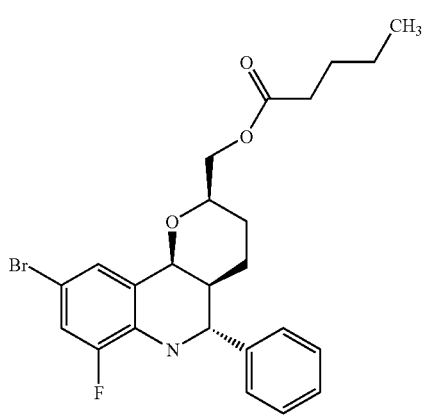
-continued
I129
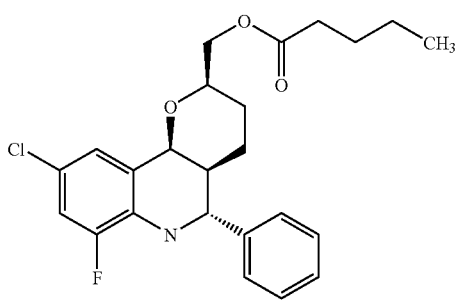
I130
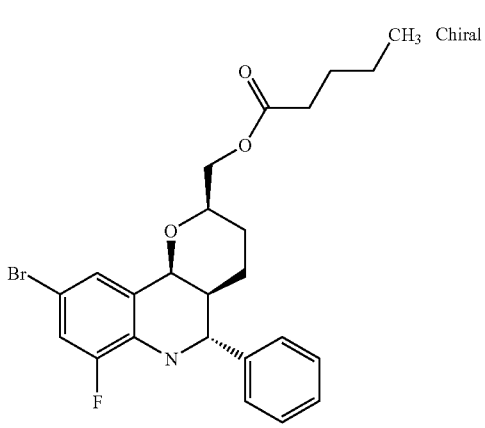
Chiral
I131
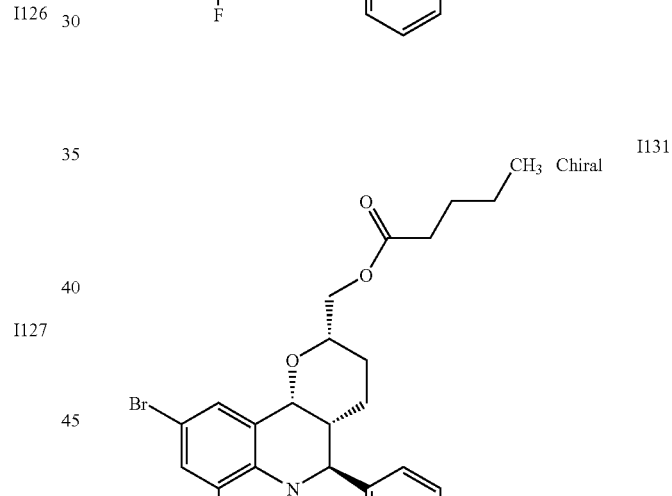
Chiral
I132
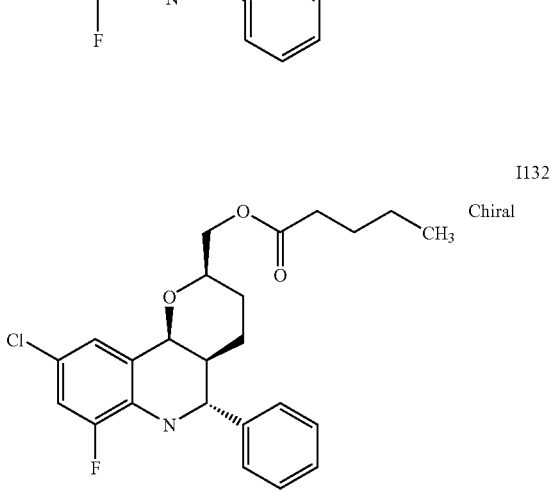
Chiral I133 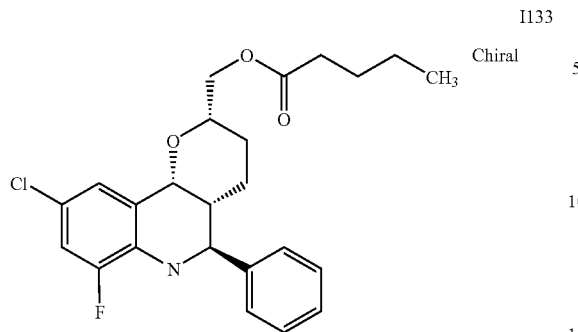
I134 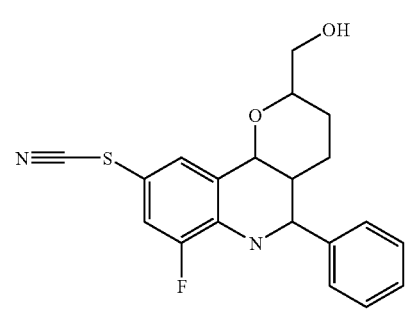
I135 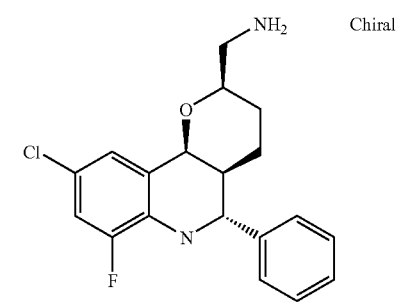
I136 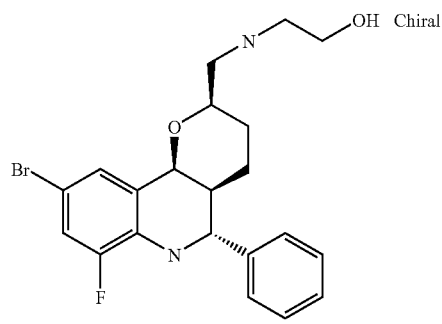
I137 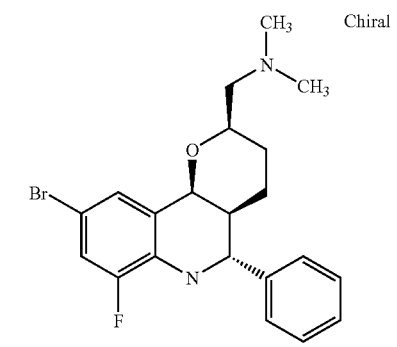
I138 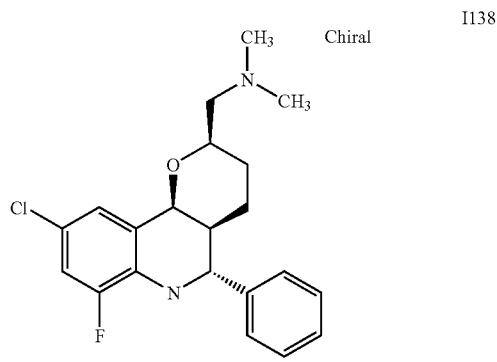
I139 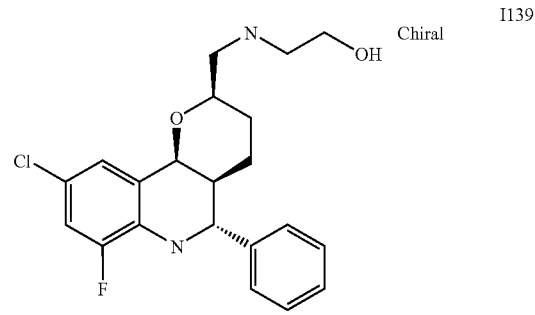
I140 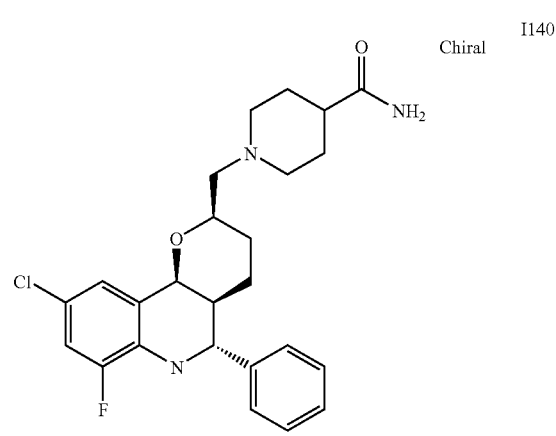
I141 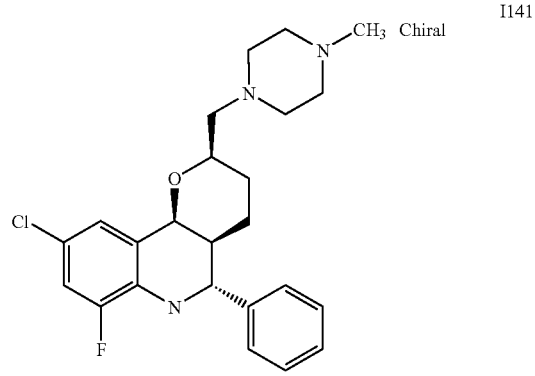

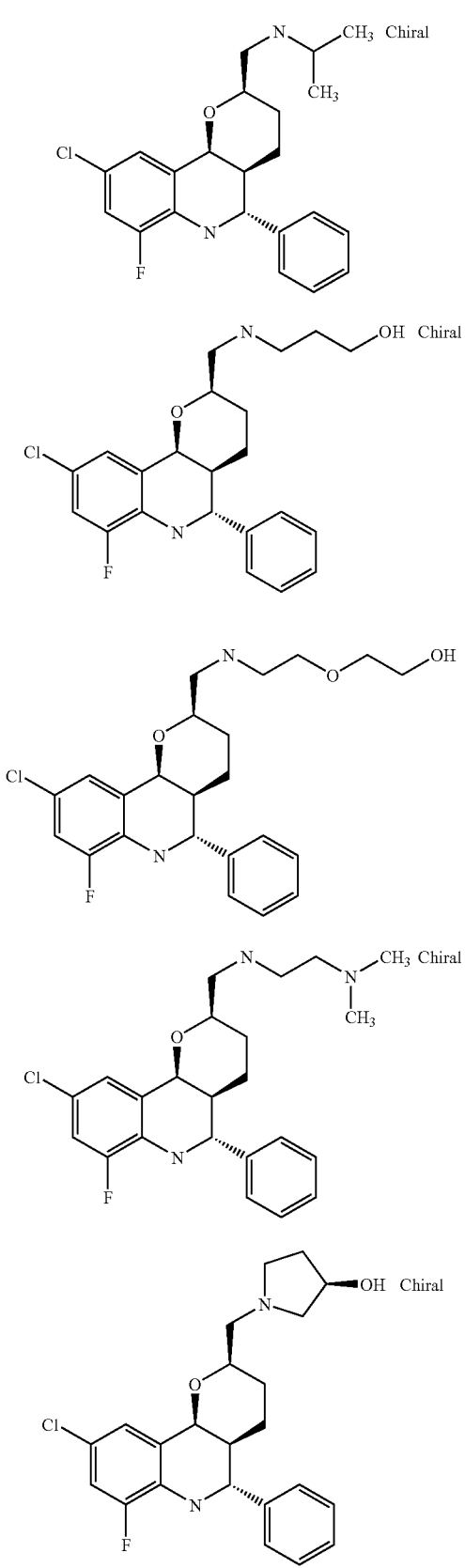
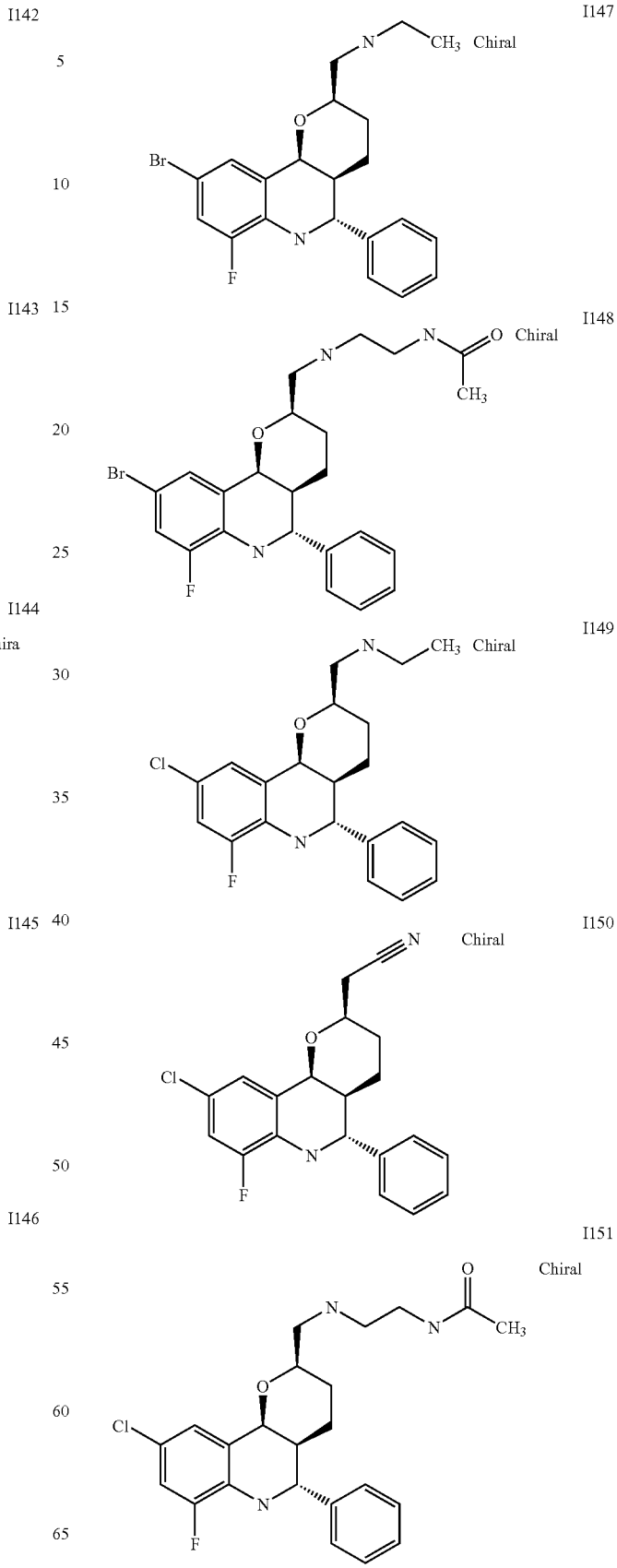

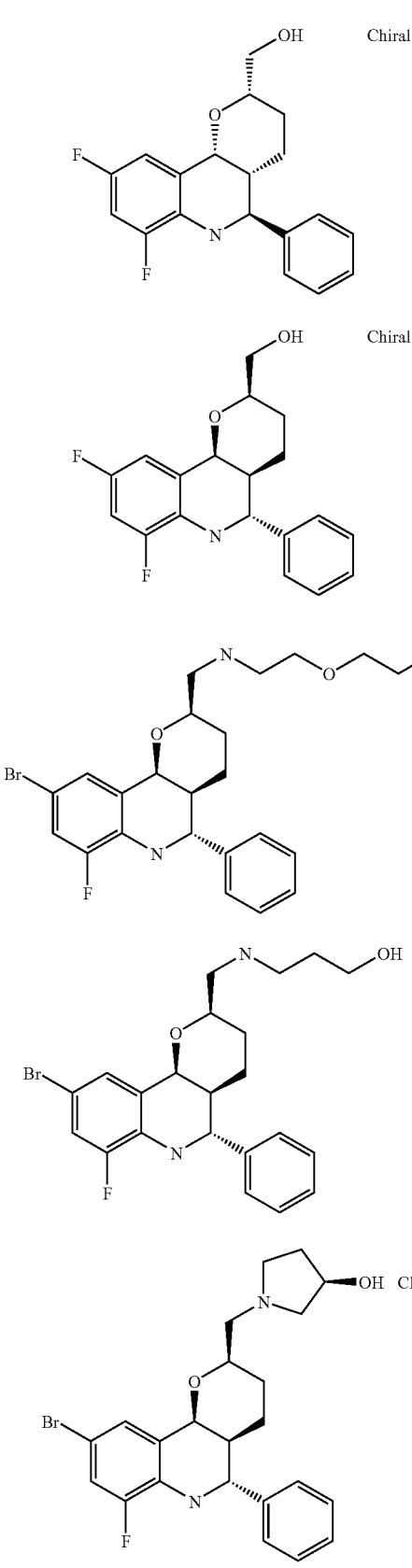
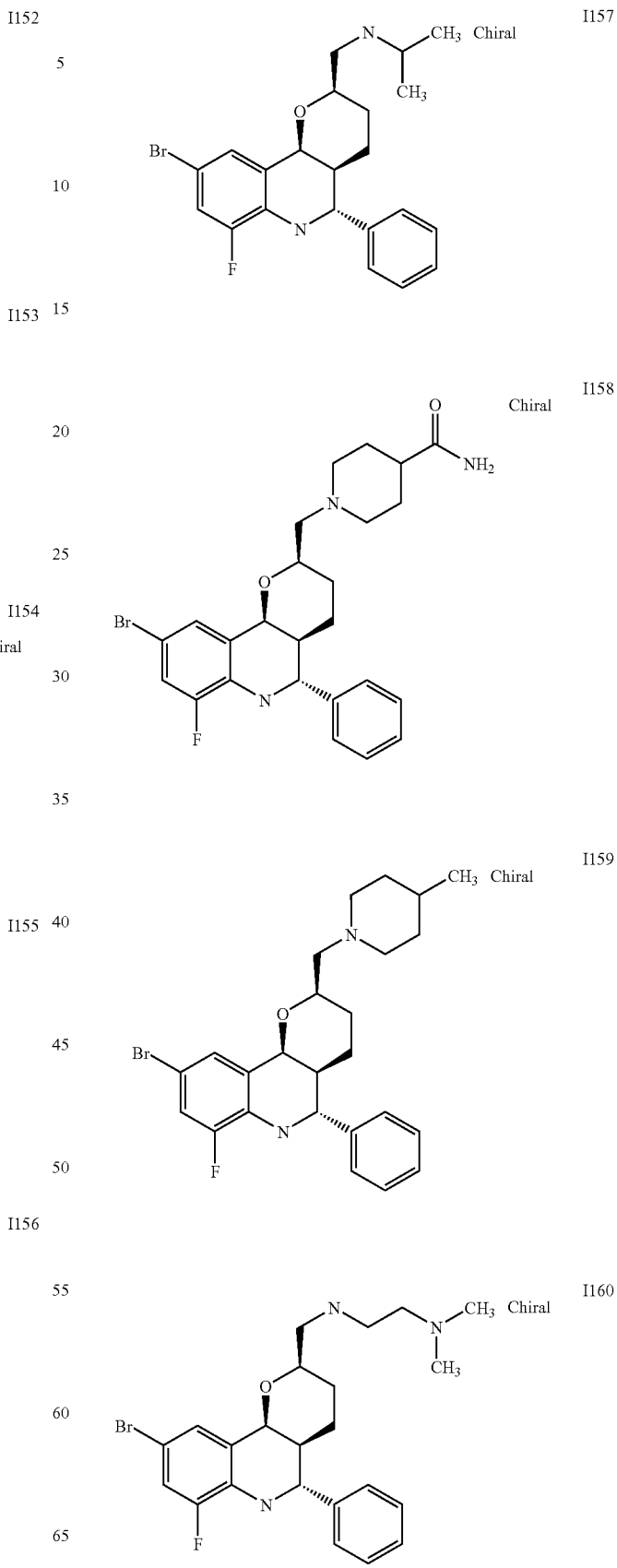

-continued
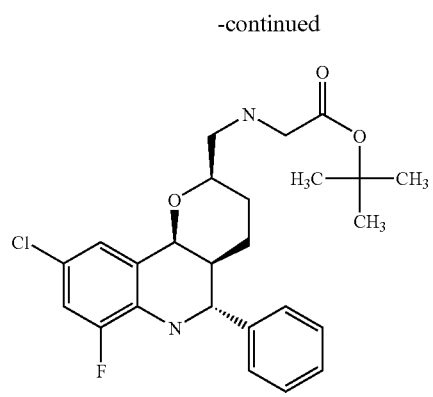
I169 Chiral
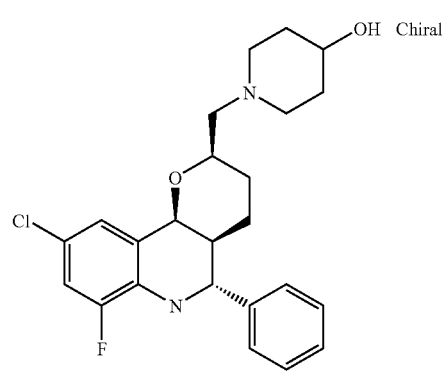
I170 Chiral
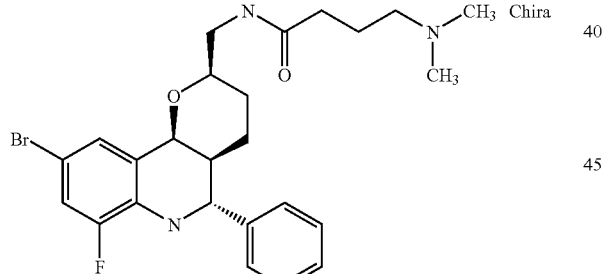
I171 Chiral
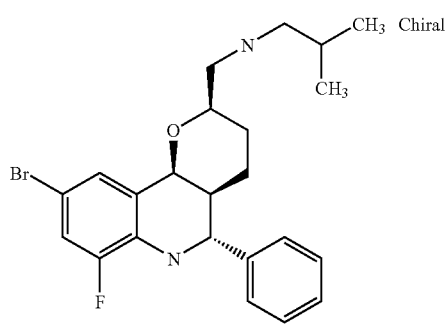
I172 Chiral
-continued
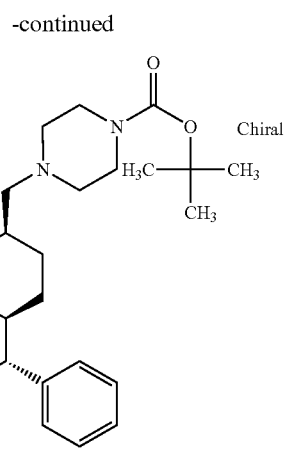
I173 Chiral
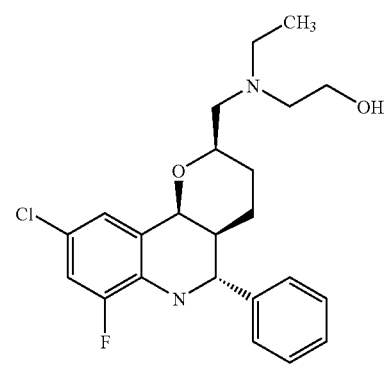
I174 Chiral
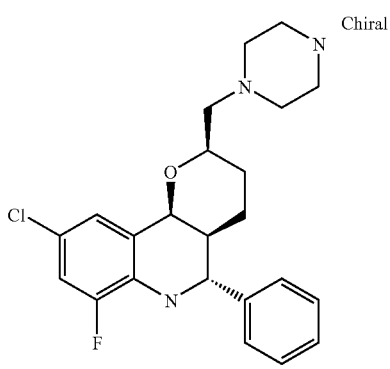
I175 Chiral
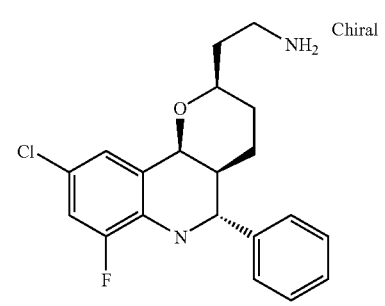
I176 Chiral -continued
I177 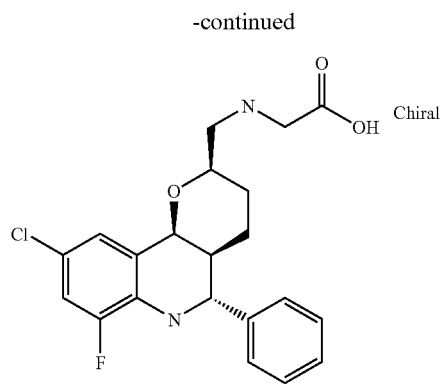
I178 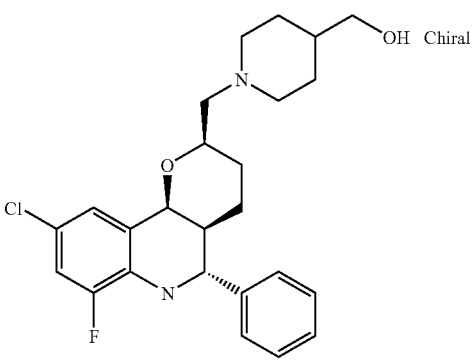
I179 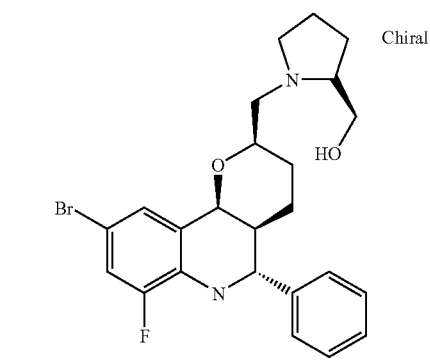
I180 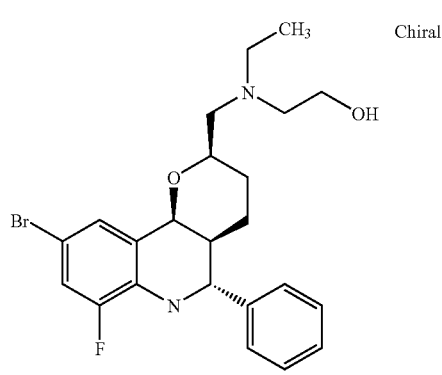
-continued
I181 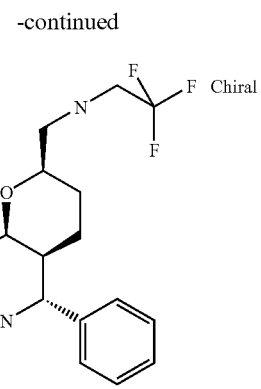
I182 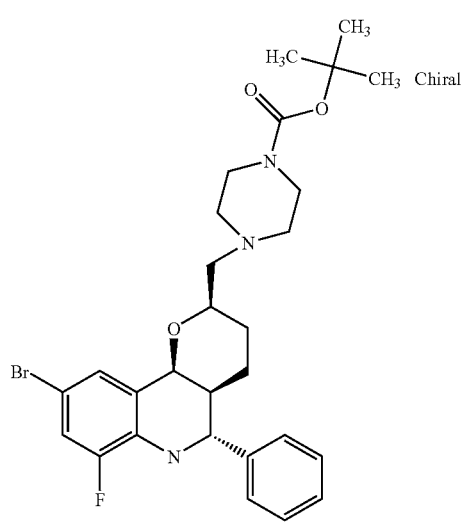
I183 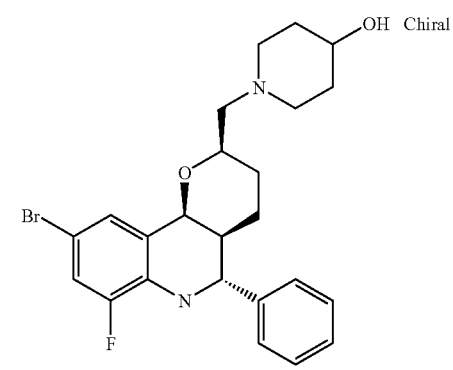
I184 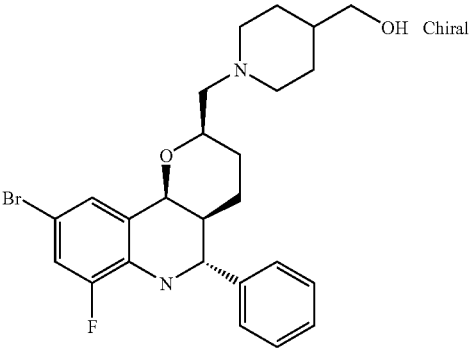

-continued
I185
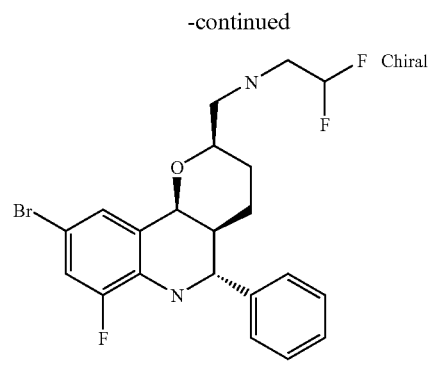
I186
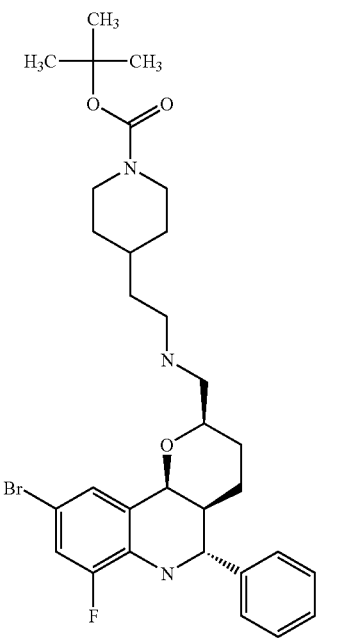
I187
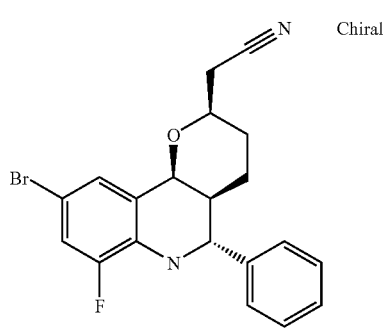
I188
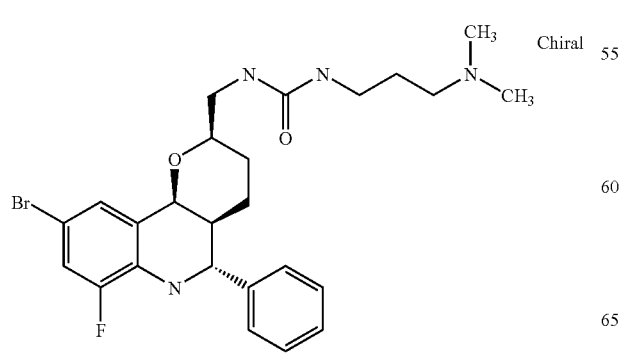
-continued
I189
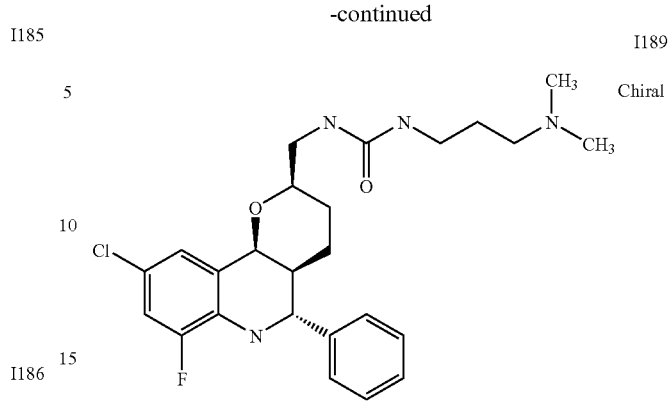
I190
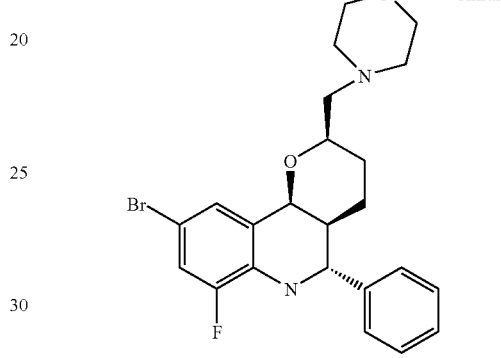
I191
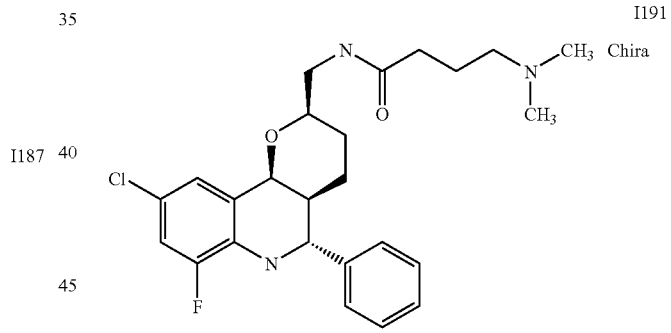
I192
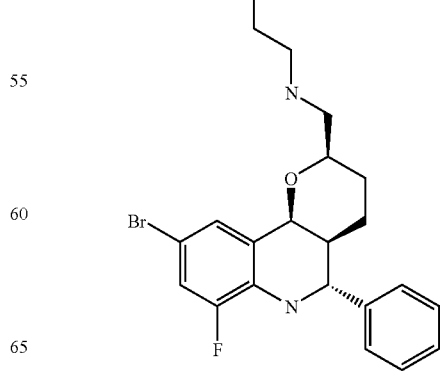

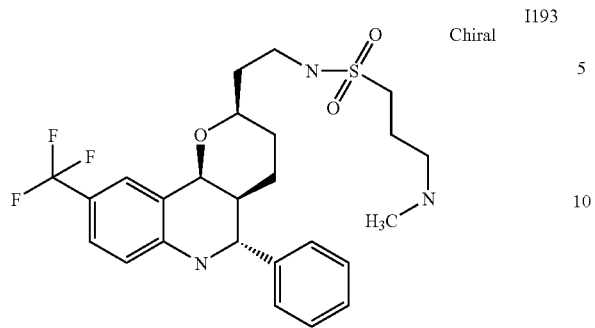
I193 Chiral
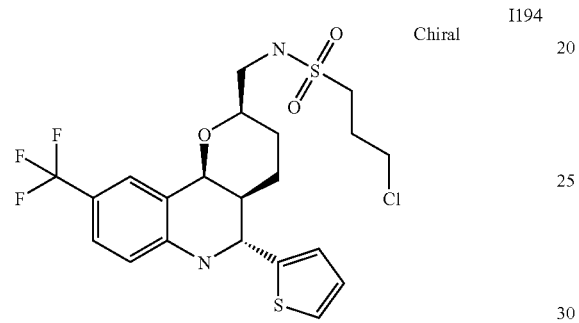
I194 Chiral
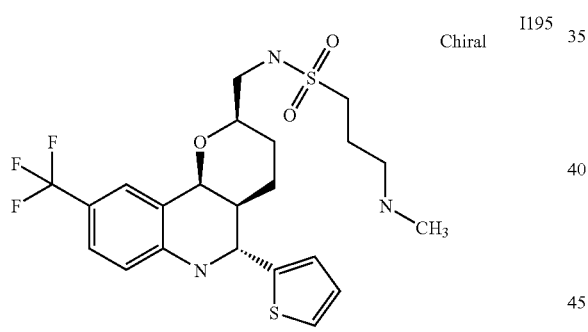
I195 Chiral
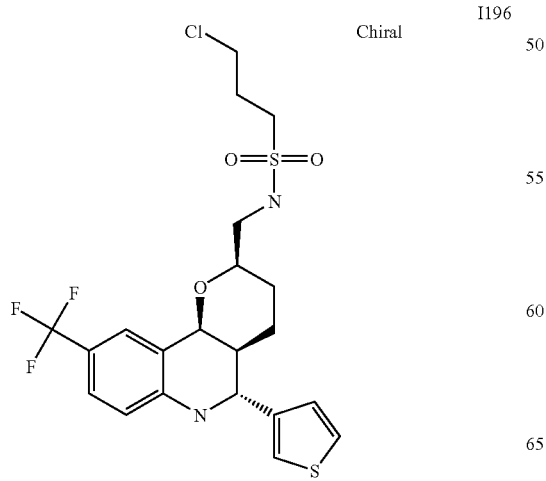
I196 Chiral
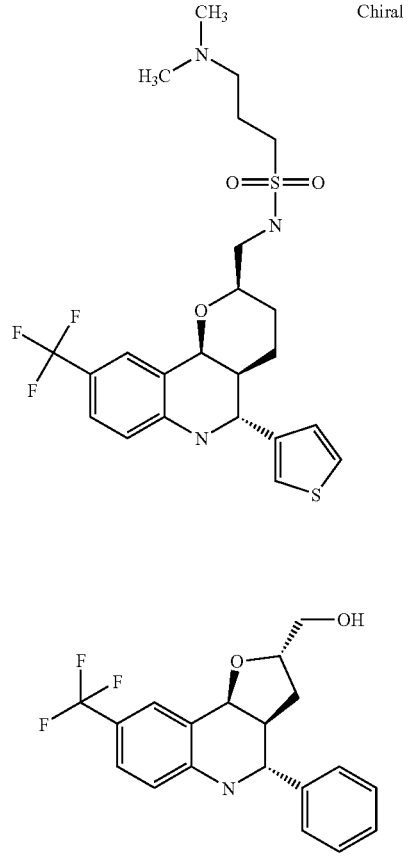
I197 Chiral
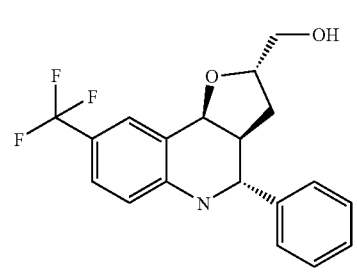
I198
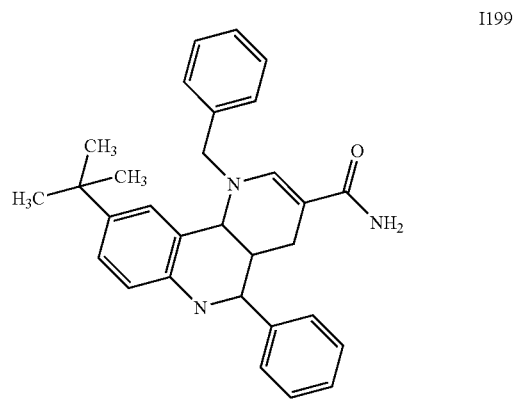
I199
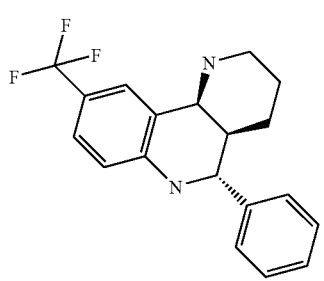
I200

-continued
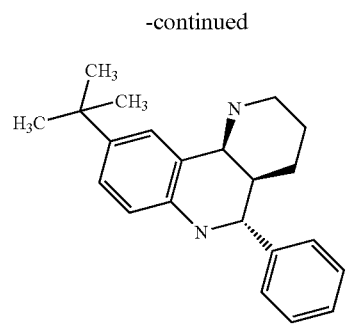
I201
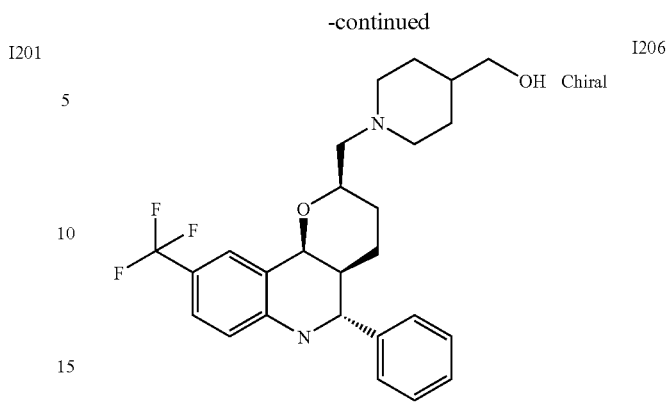
I206
I207
I208
I209
-continued
I202
I203
I204
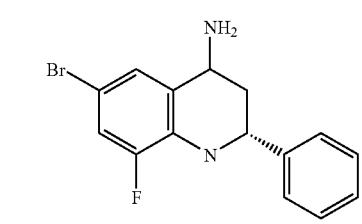
I205
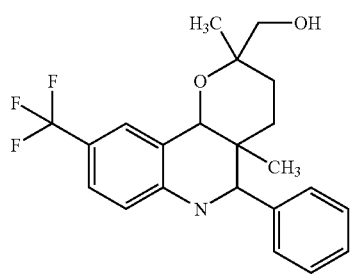

-continued
I210 Chiral
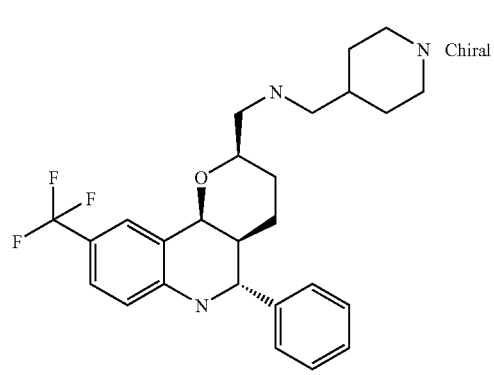
I211 Chiral
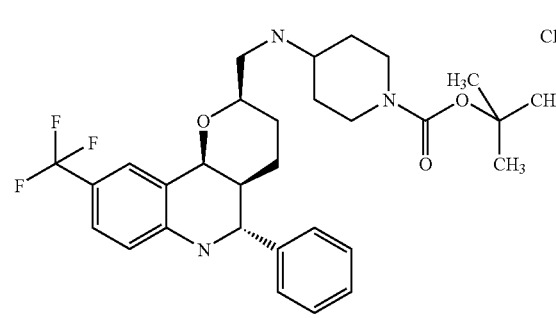
I212 Chiral
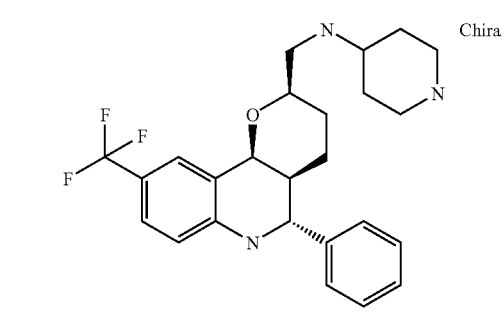
I213 Chiral
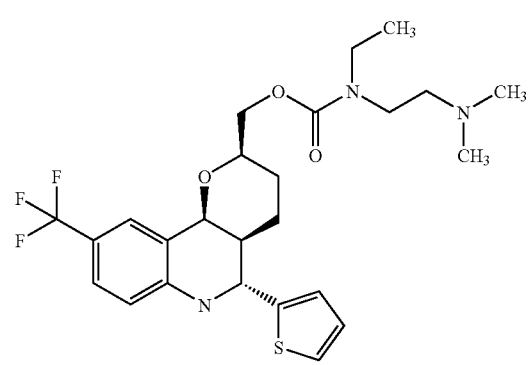
-continued
I214 Chiral
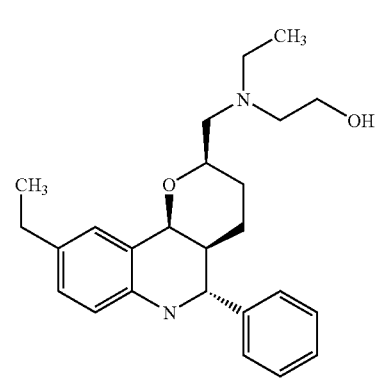
I215 Chiral
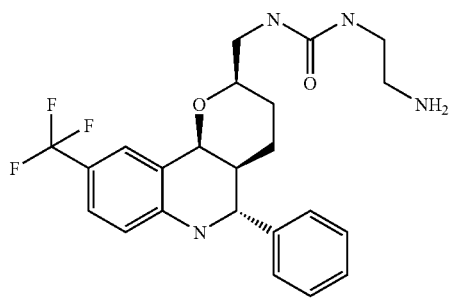
I216 Chiral
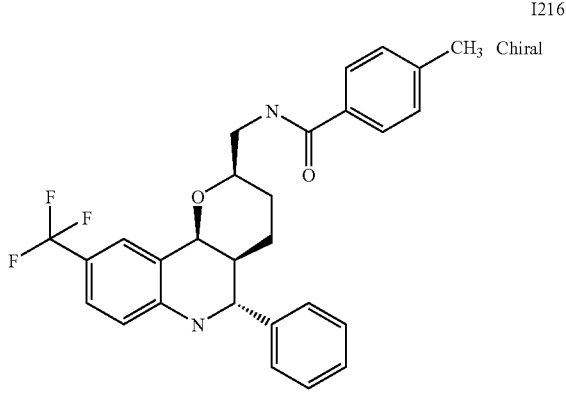
I217 Chiral
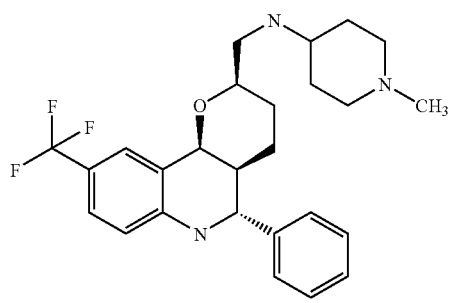

-continued
I218 Chiral
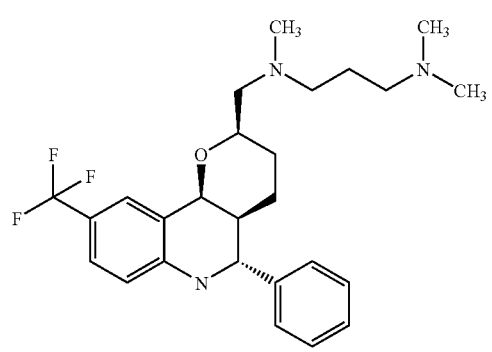
I219 Chiral
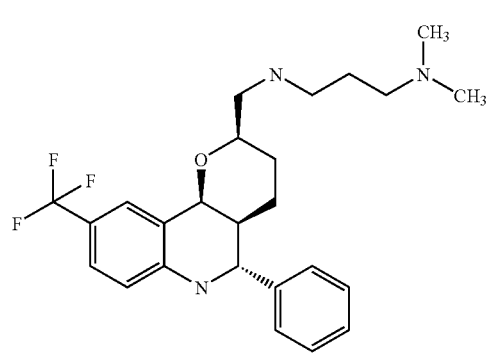
I220 Chiral
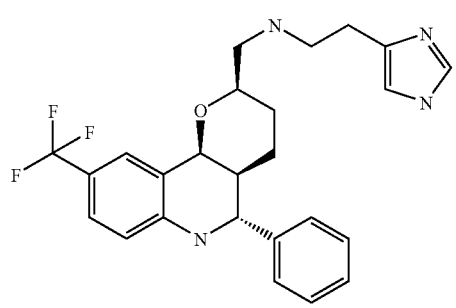
I221
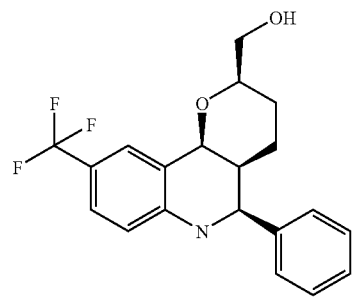
-continued
I222 Chiral
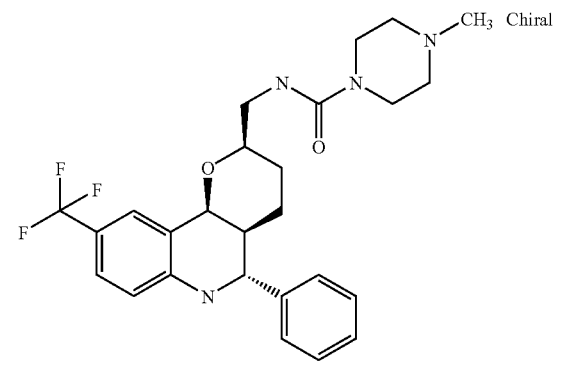
I223 Chiral
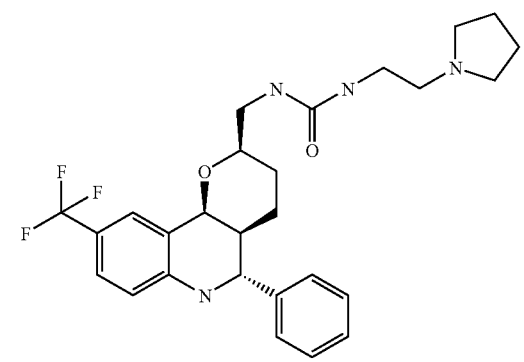
I224 Chiral
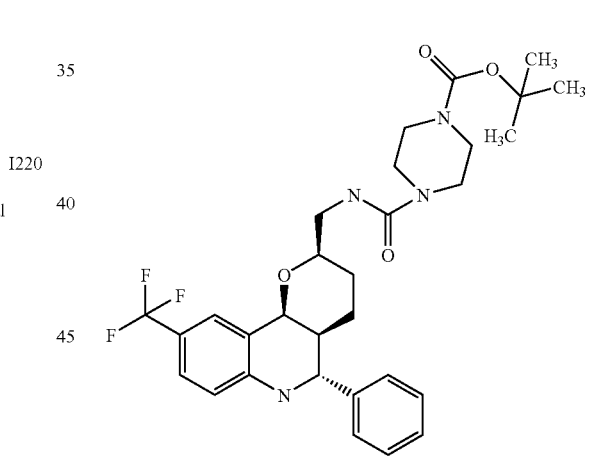
I225 Chiral
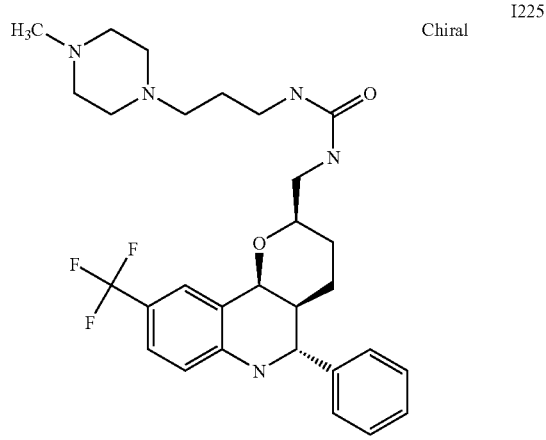

75
-continued
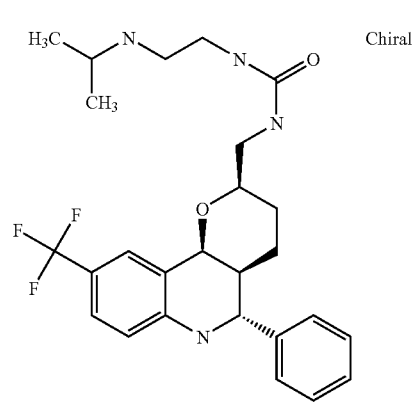
I226
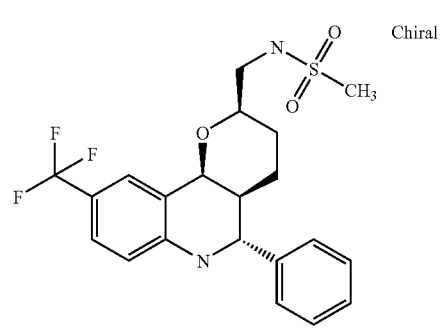
I227
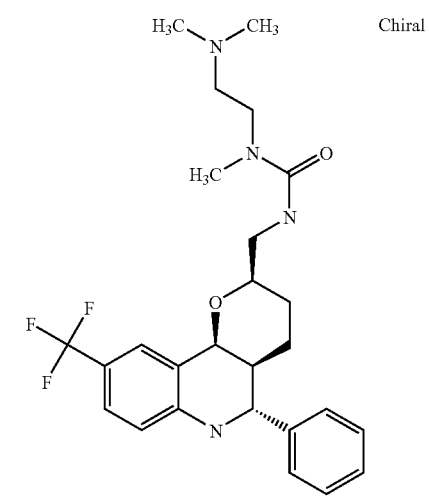
I228
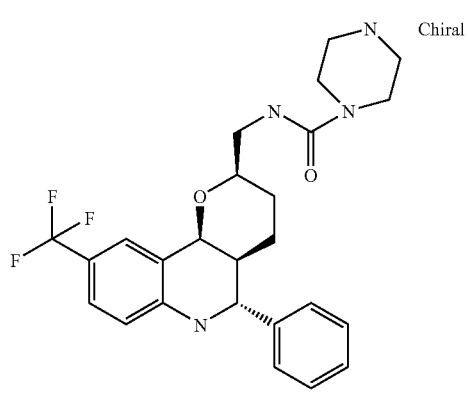
I229
76
-continued
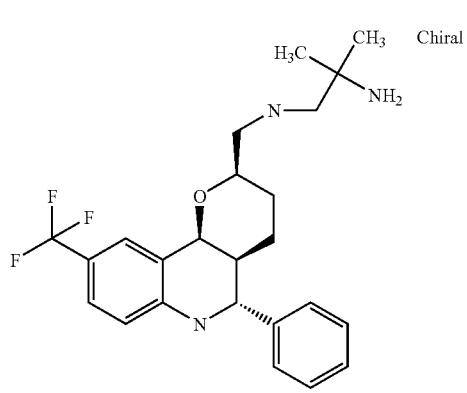
I230
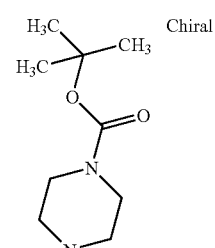
I231
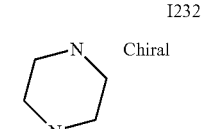
I232

I233
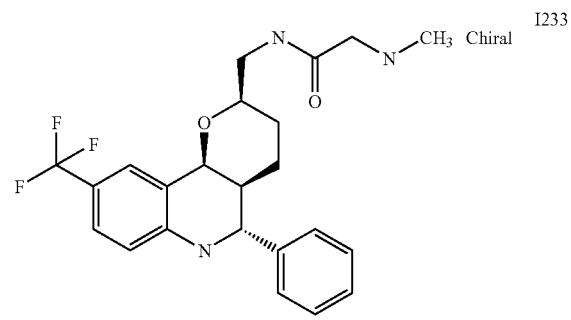
I234
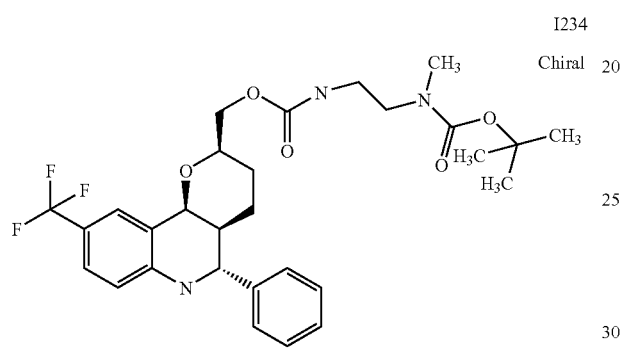
I235
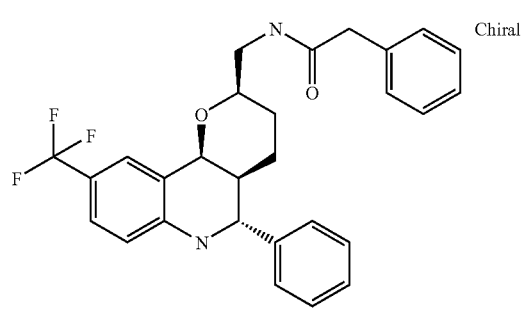
I236
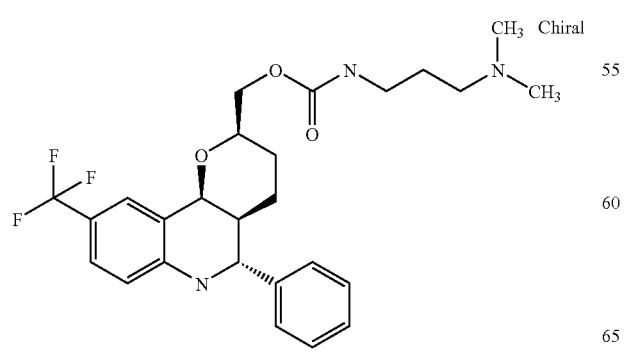
I237
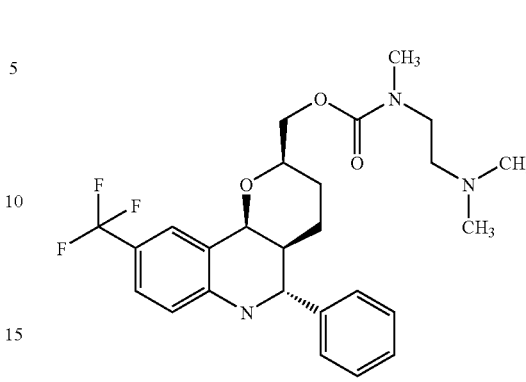
I238
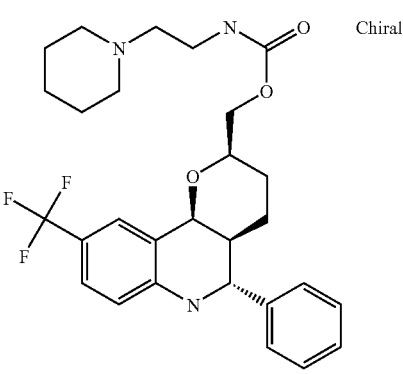
I239
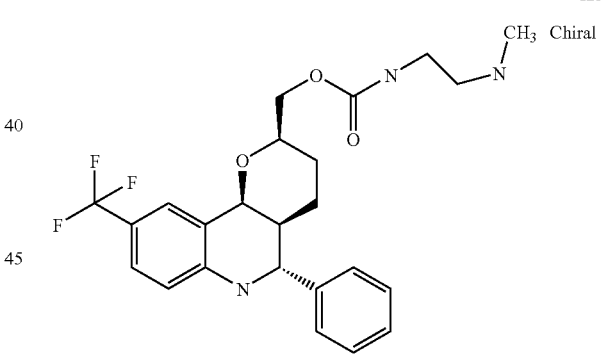
I240
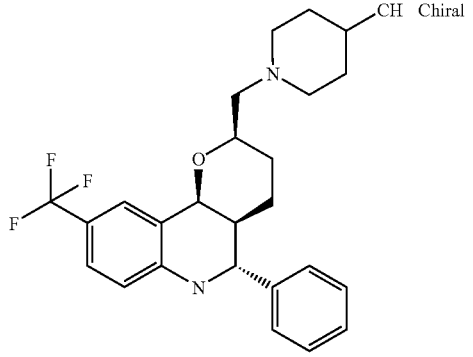

-continued
I241
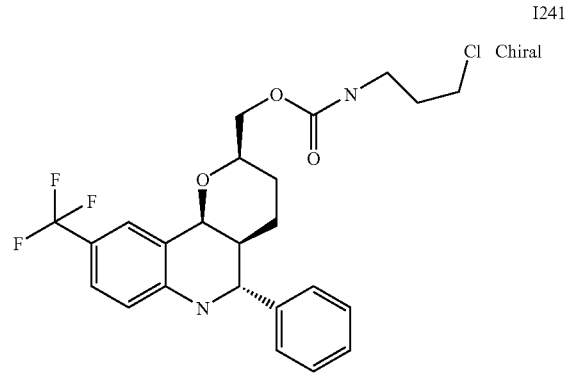
I242
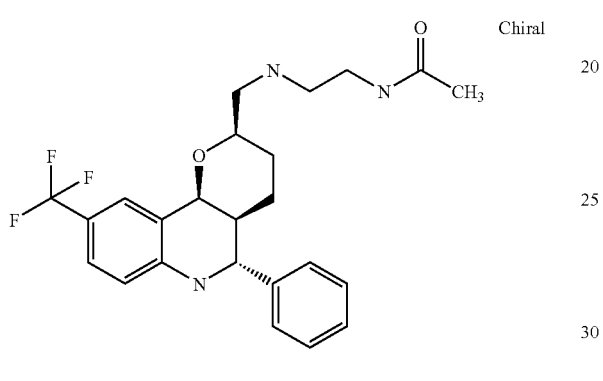
I243
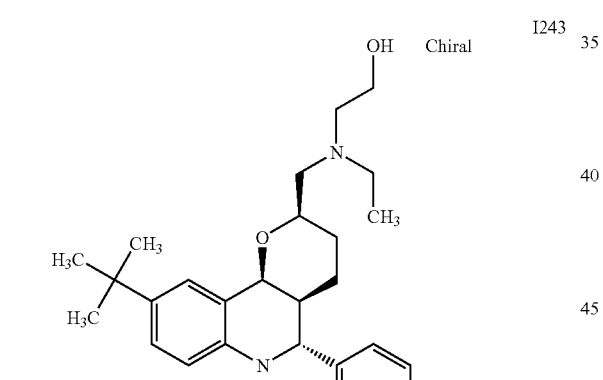
I244
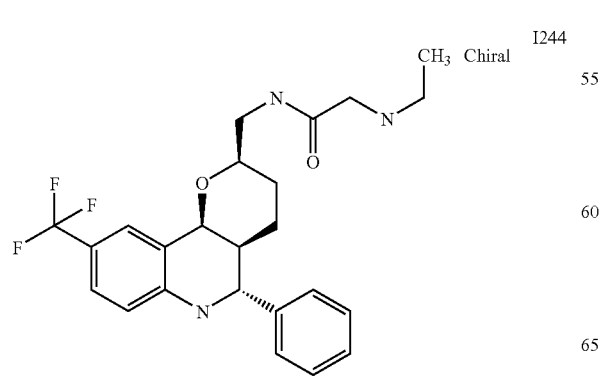
-continued
I245
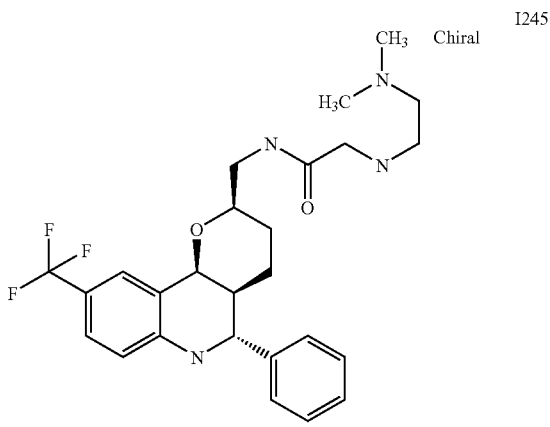
I246
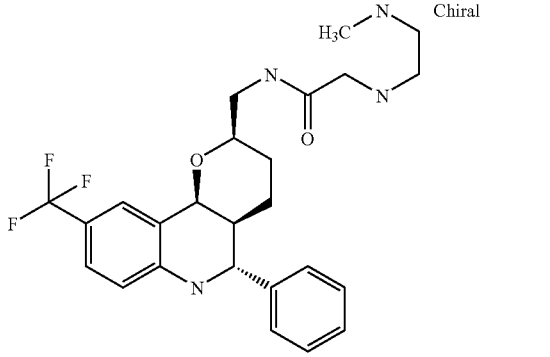
I247
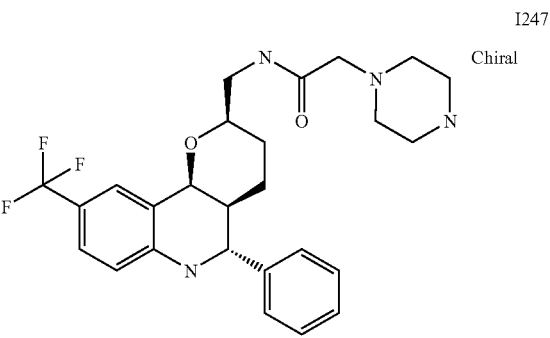
I248
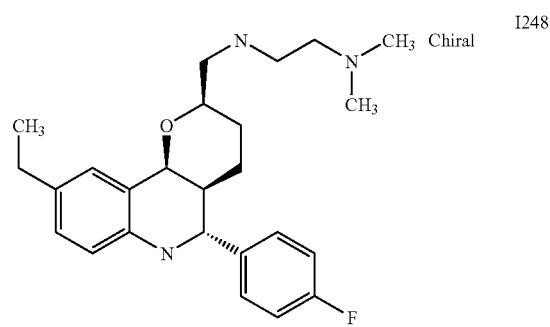

I249
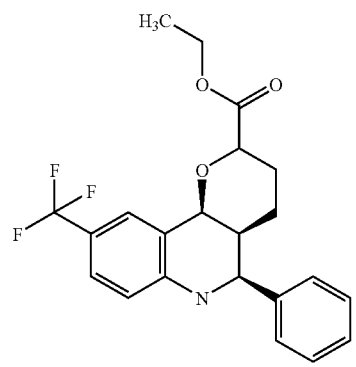
I250
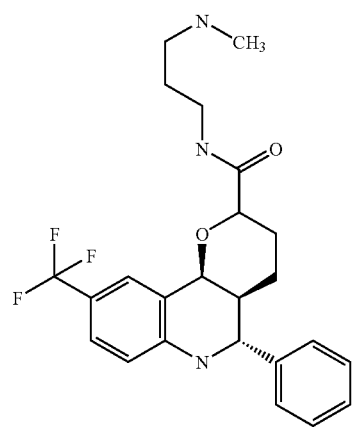
I251
Chiral
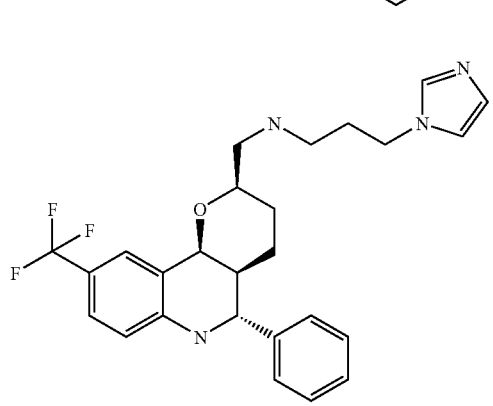
I252
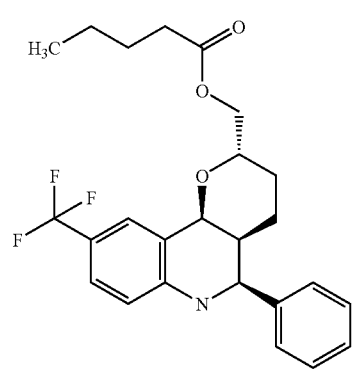
I253
Chiral
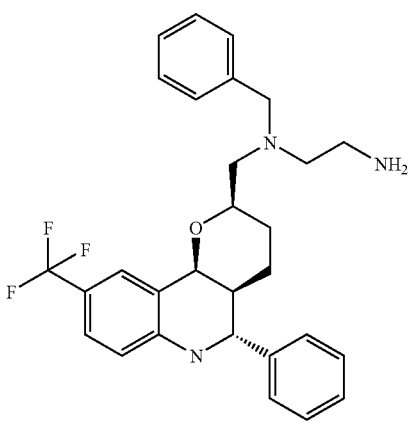
I254
Chiral
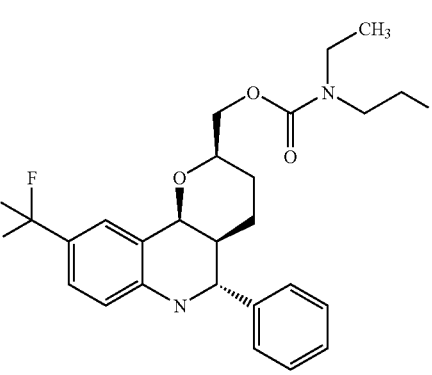
I255
Chiral
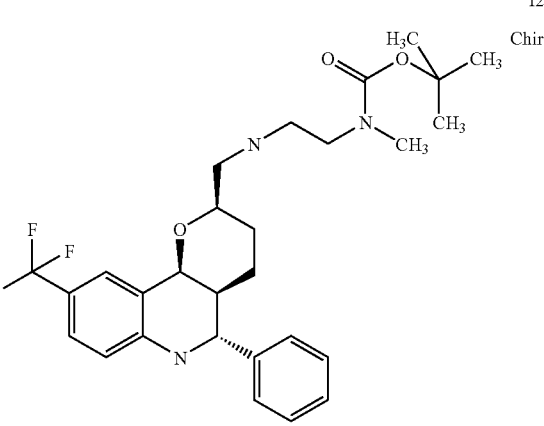
I256
Chiral
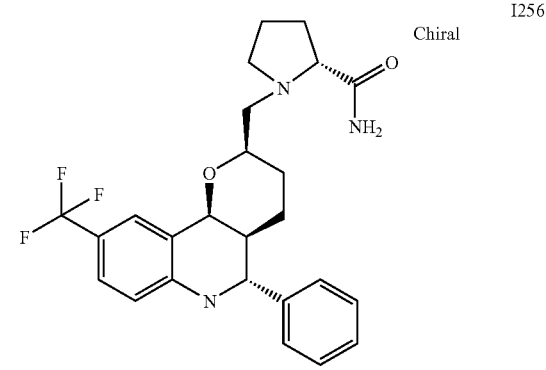

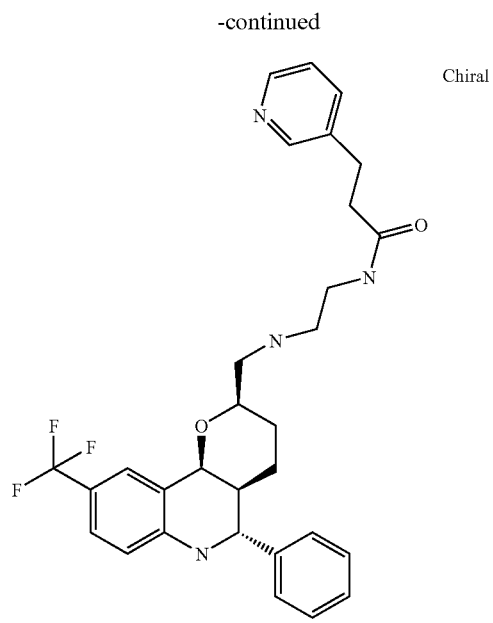
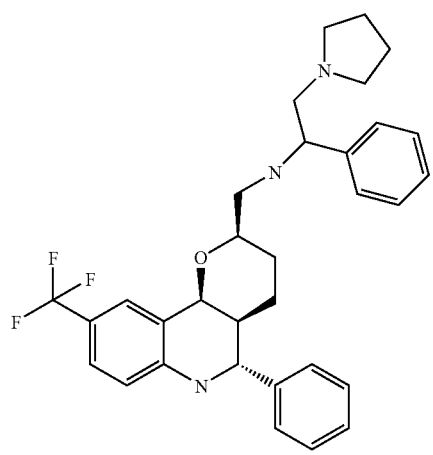
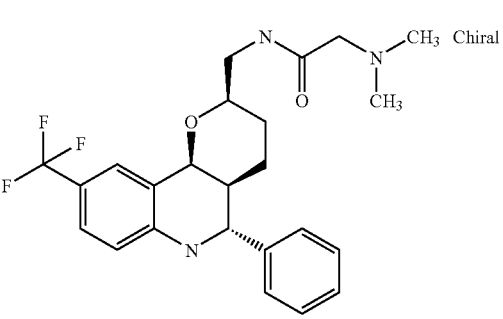
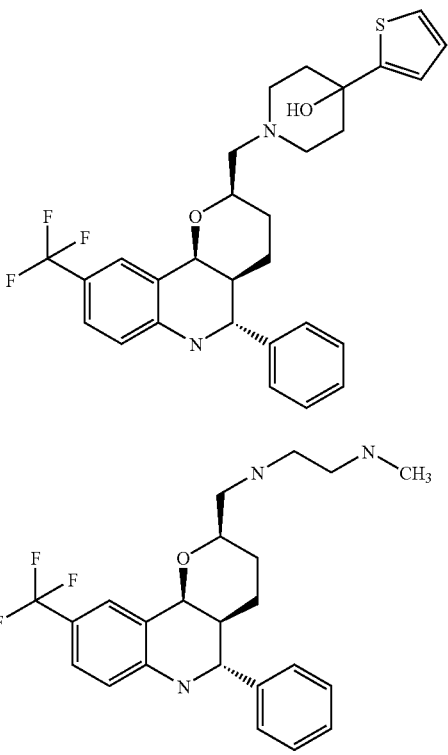
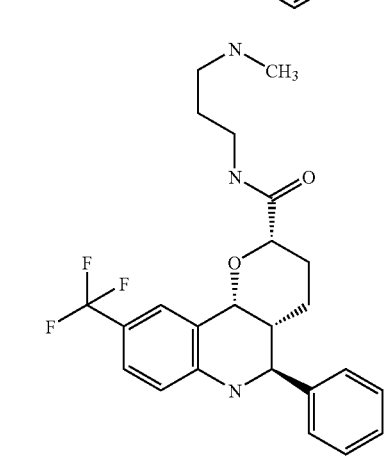
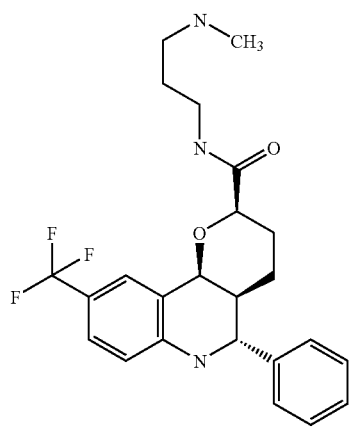

I264 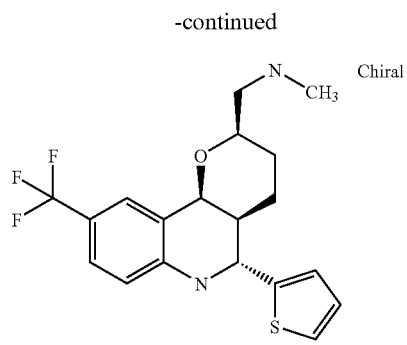
I265 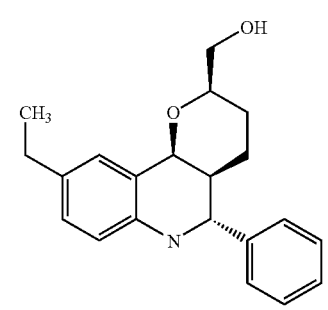
I266 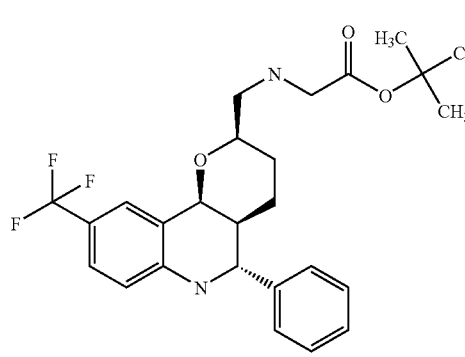
I267 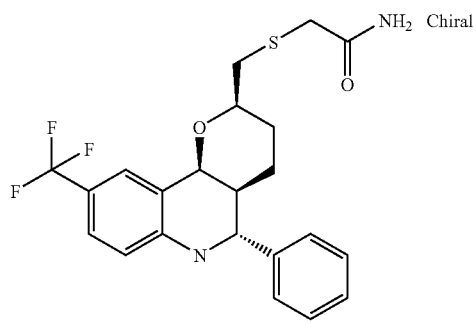
I268 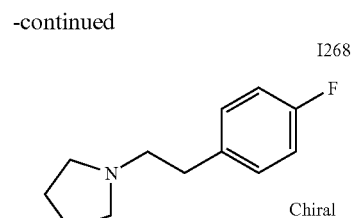
I269 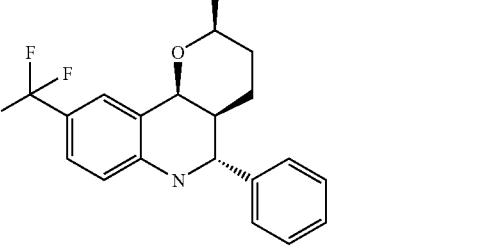
I270 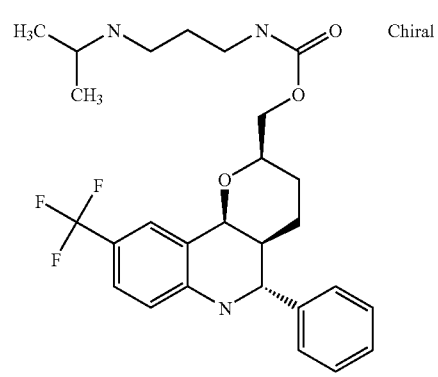

-continued
| | |
|---|---|
| 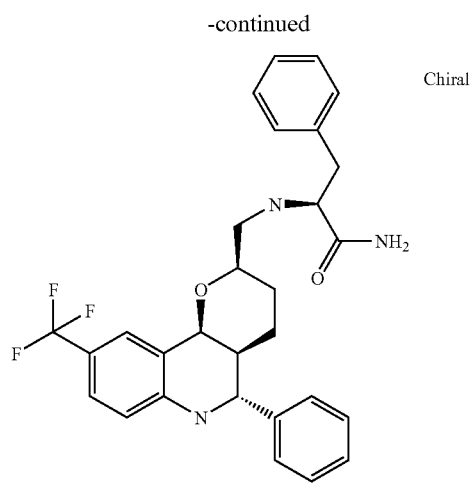 | I271 Chiral |
| 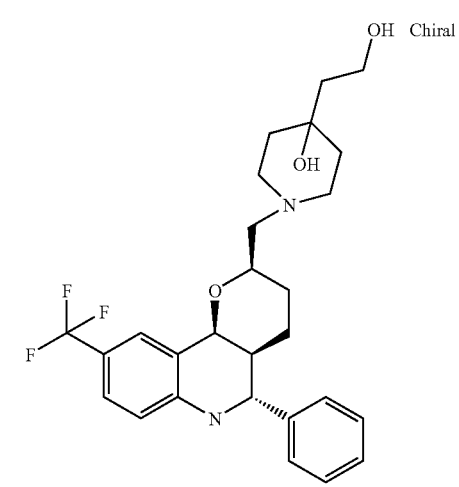 | I272 Chiral |
| 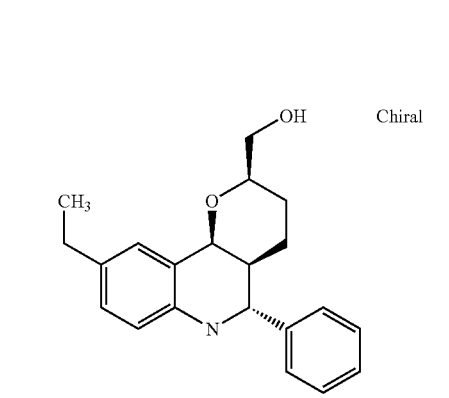 | I273 Chiral |
| 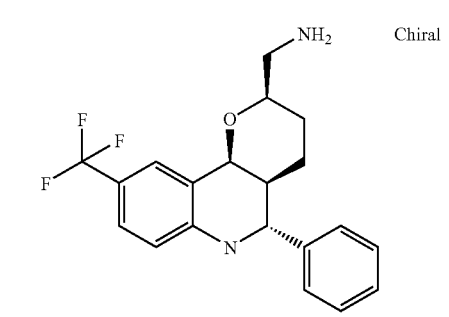 | I274 Chiral |
-continued
| | |
|---|---|
| 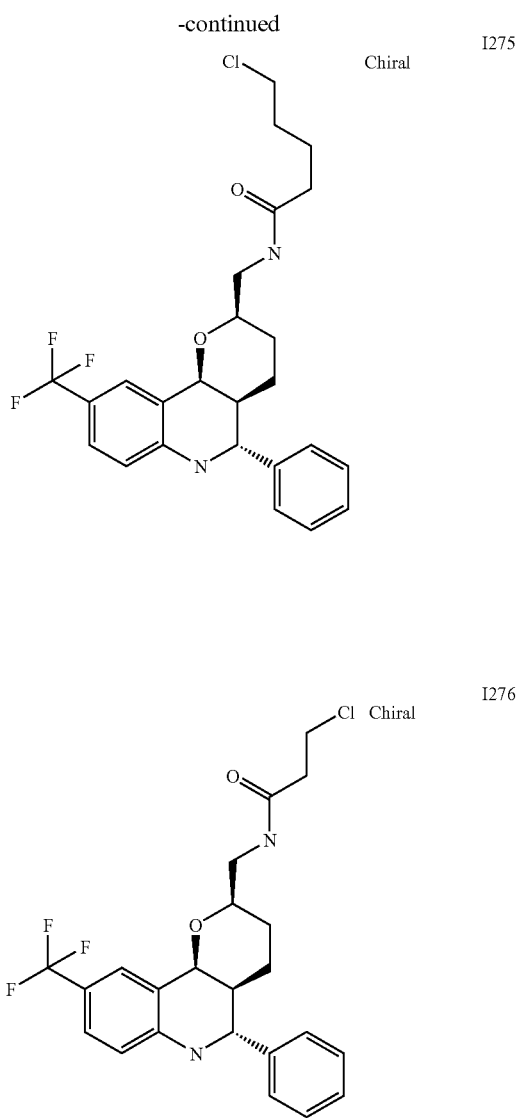 | I275 Chiral |
| | I276 Chiral |
| 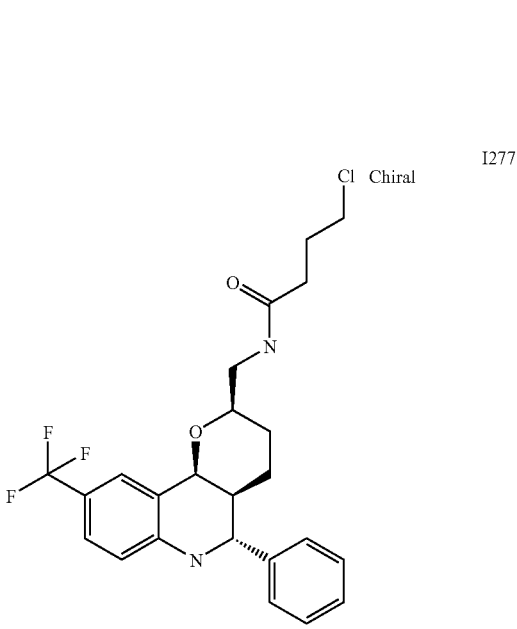 | I277 Chiral |

-continued
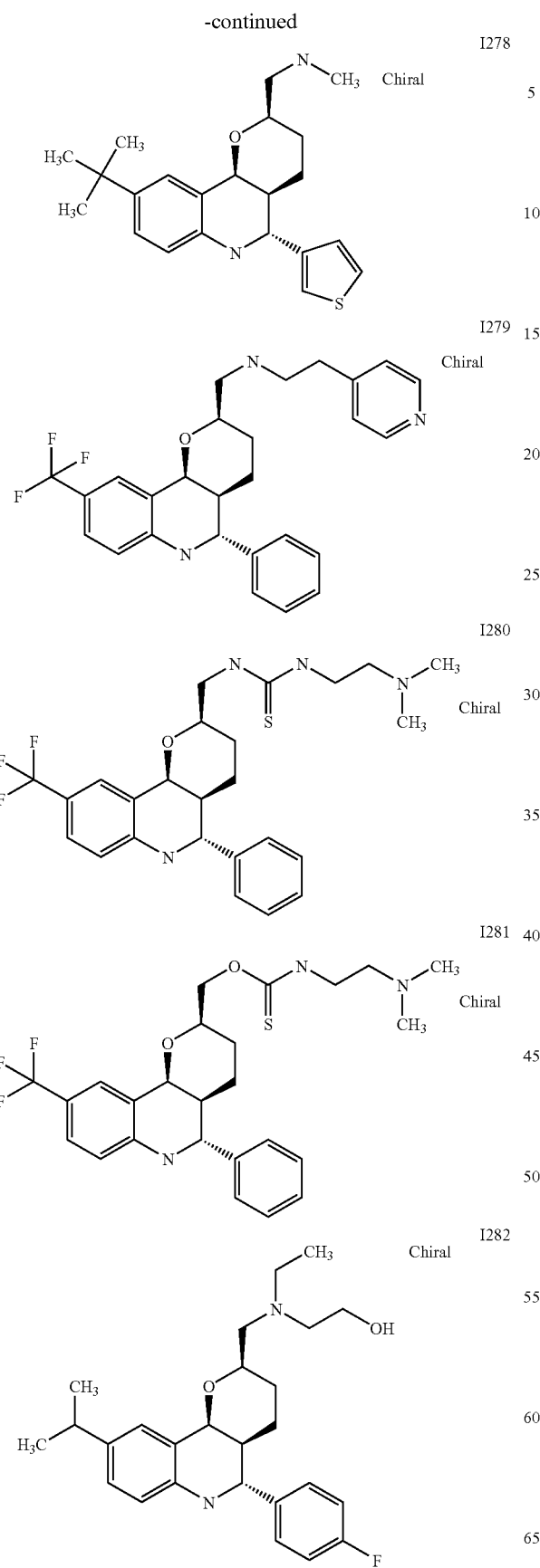
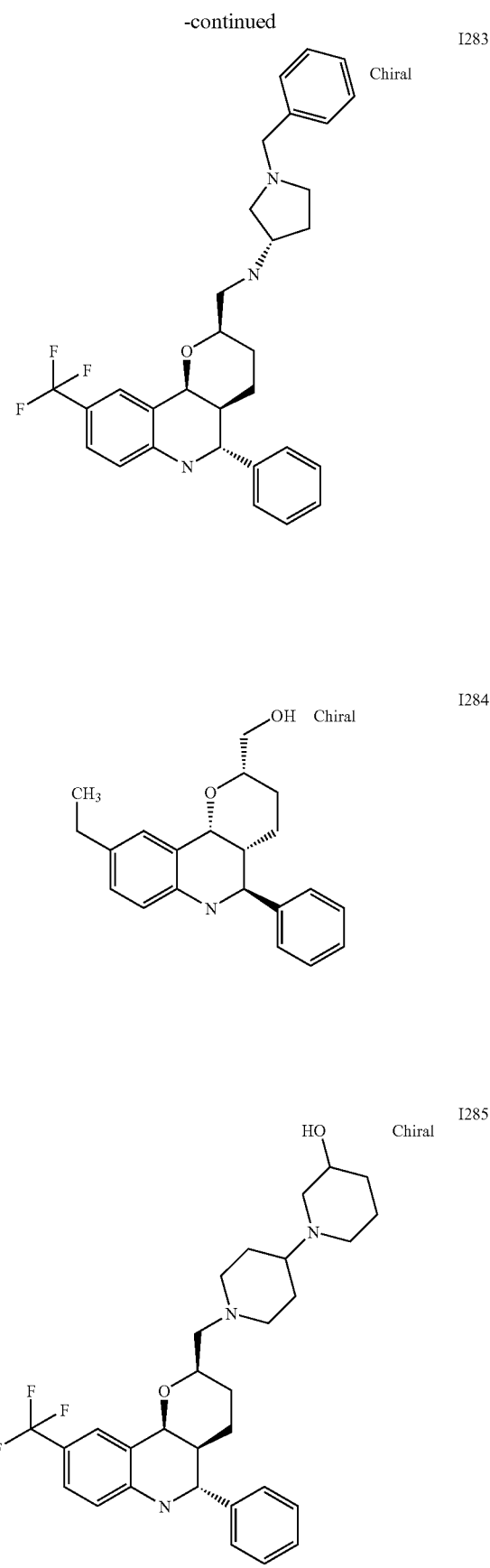

-continued
I286
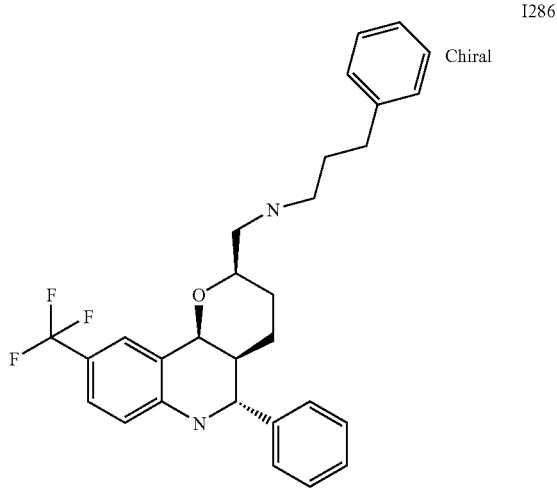
I287
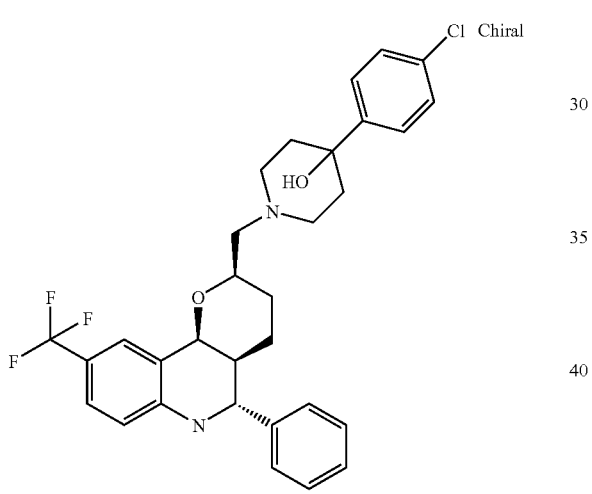
I288
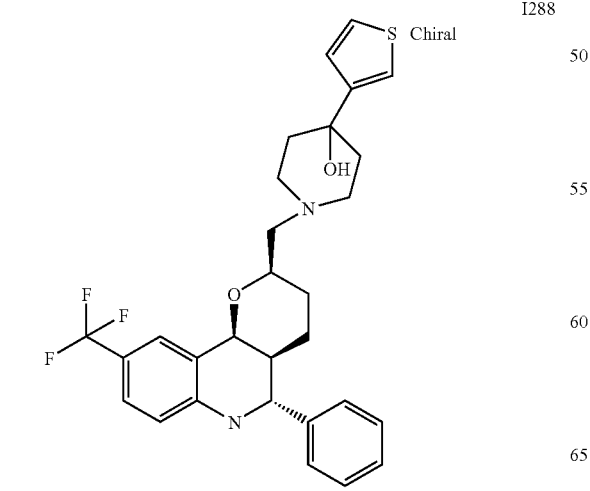
-continued
I289
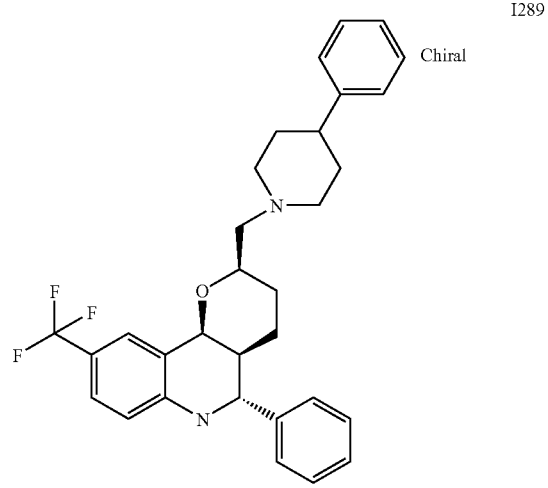
I290
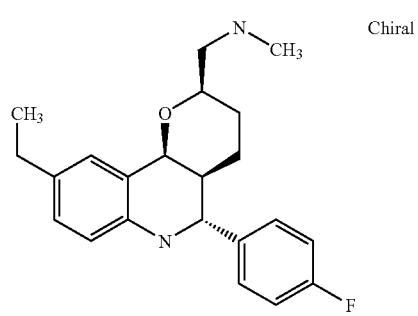
I291
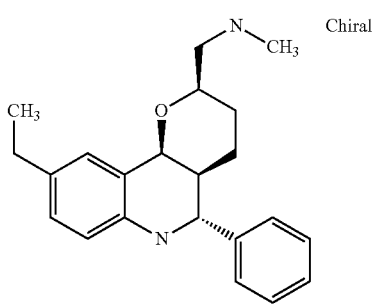
I292
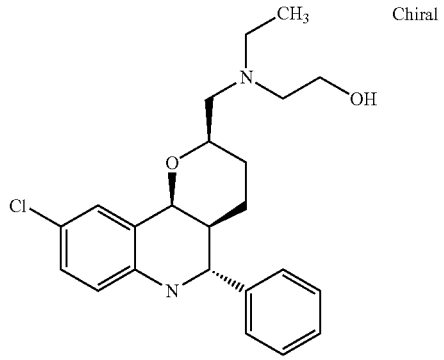

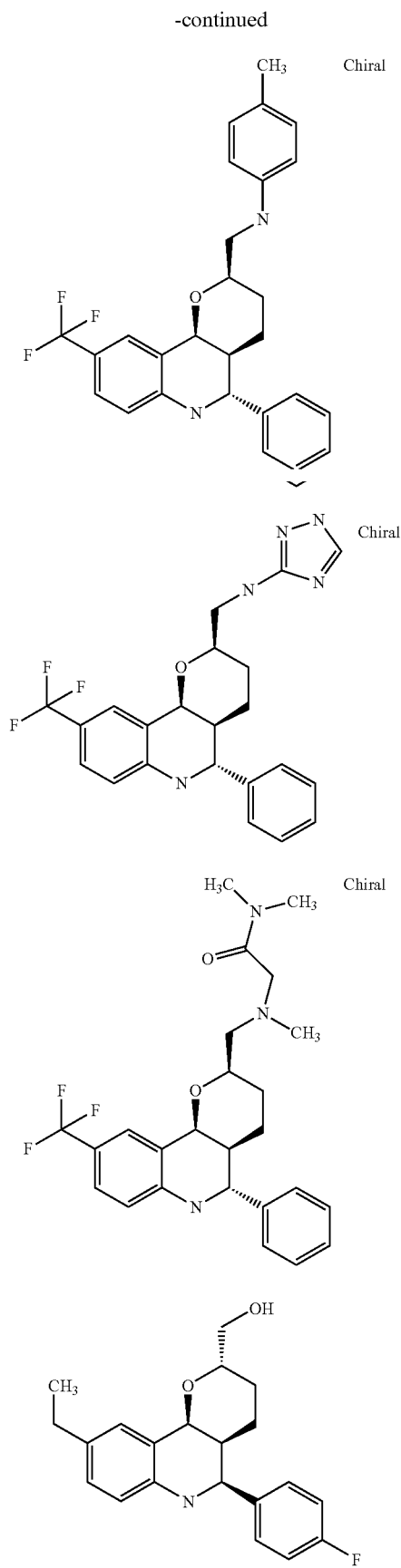
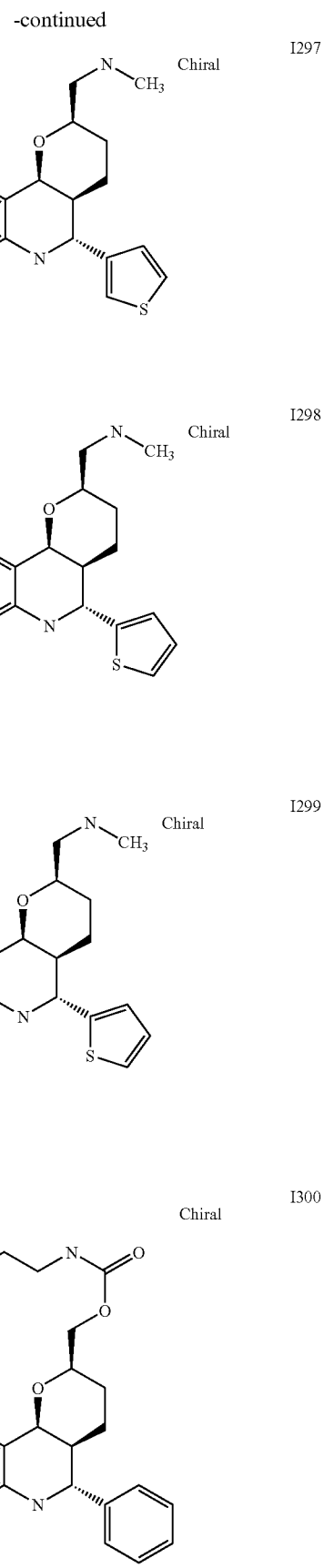

-continued
I301
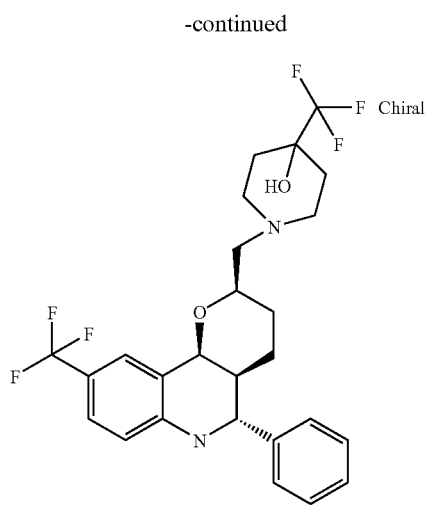
I302
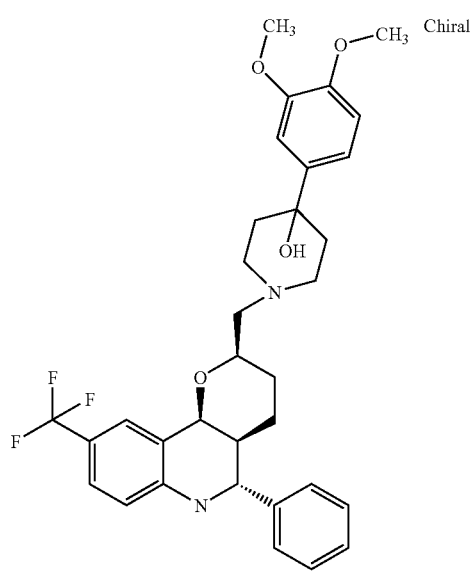
I303
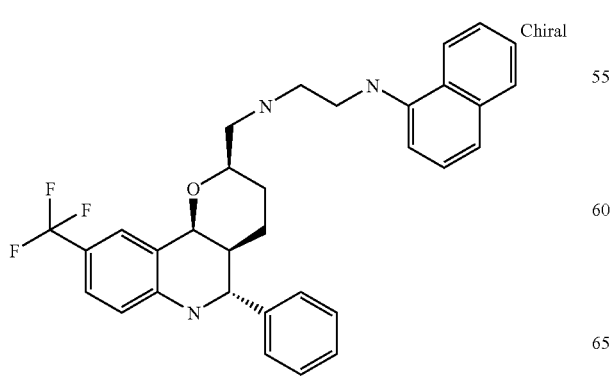
-continued
I304
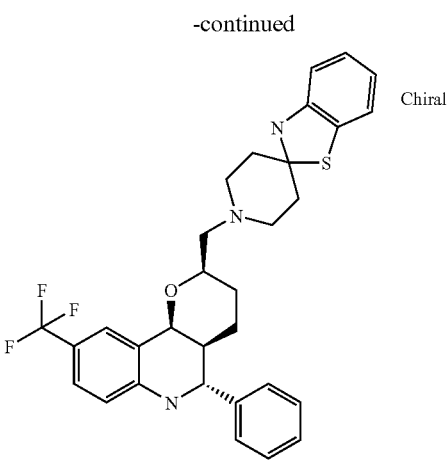
I305
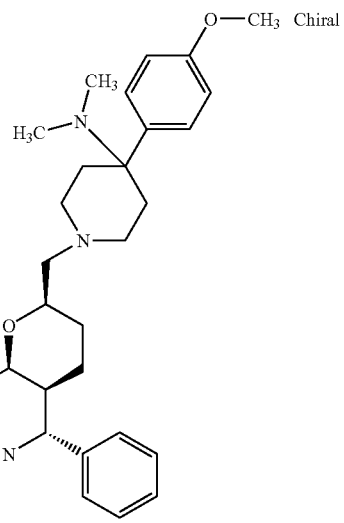
I306
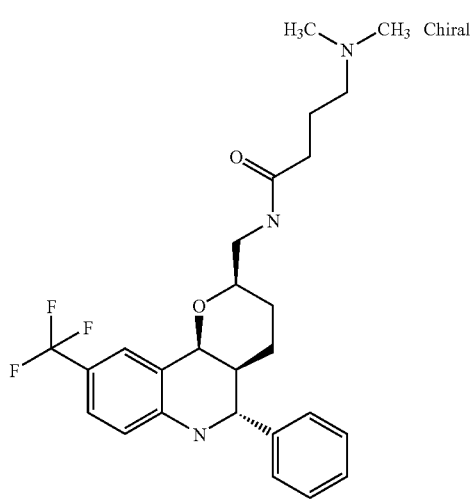

-continued
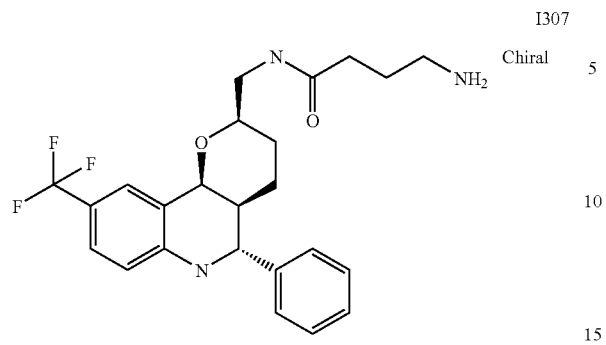
I307
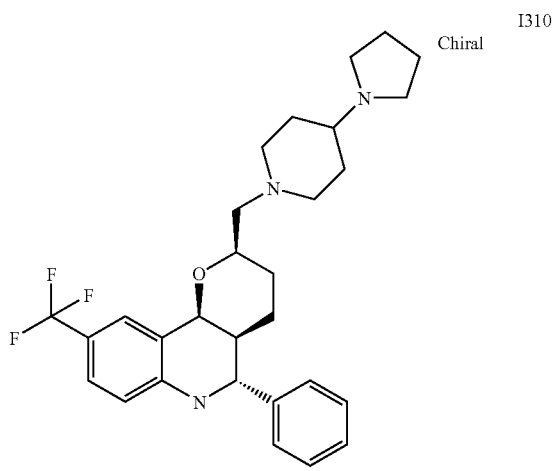
I310
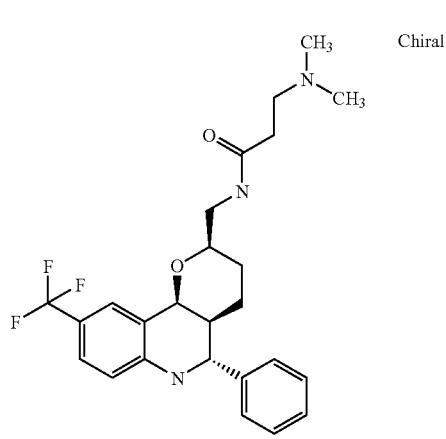
I308
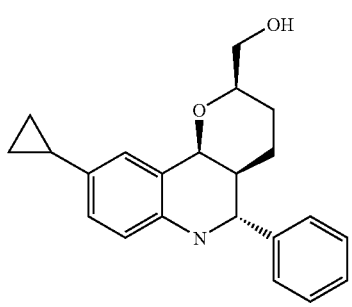
I311
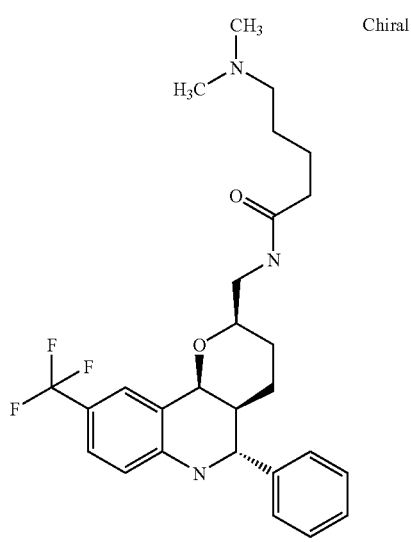
I309
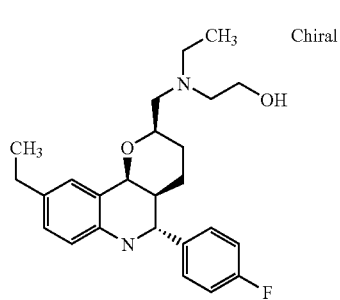
I312
I313

-continued
I314 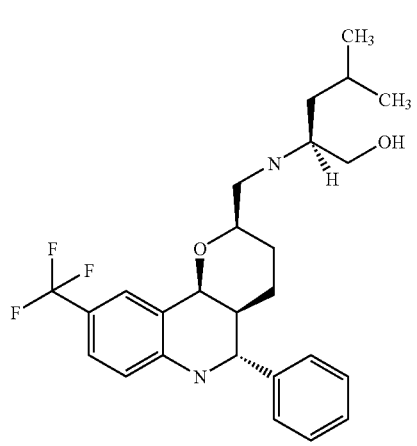
I315 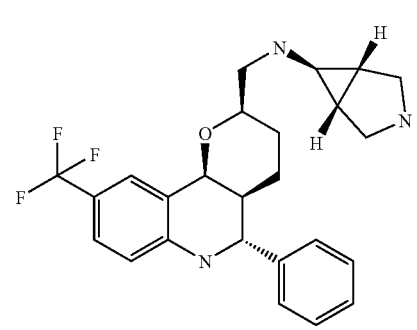
I316 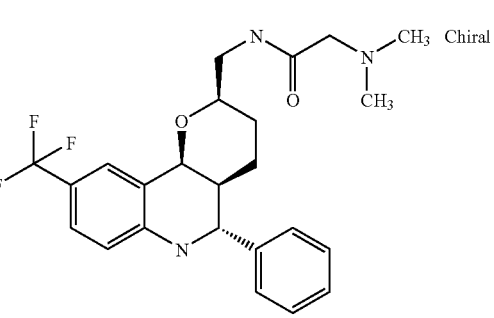
I317 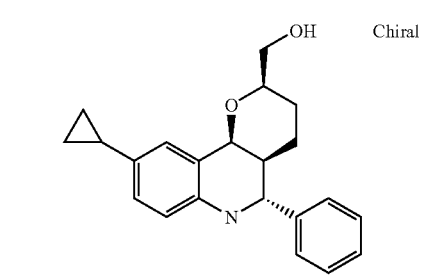
I318 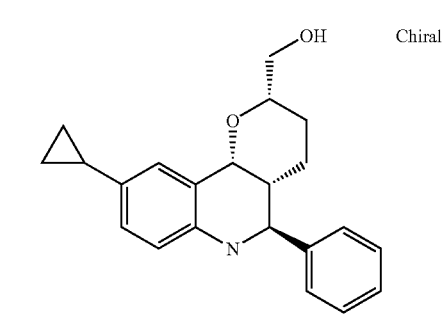
-continued
I319 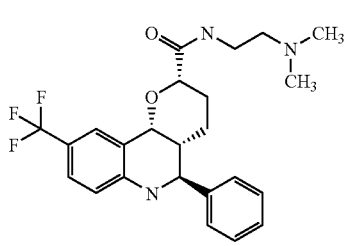
I320 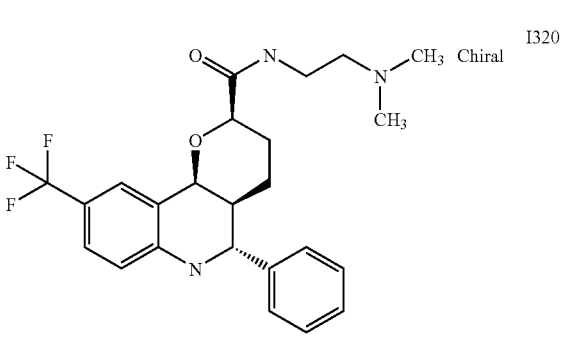
I321 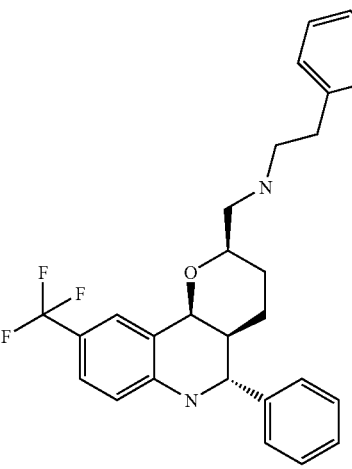
I322 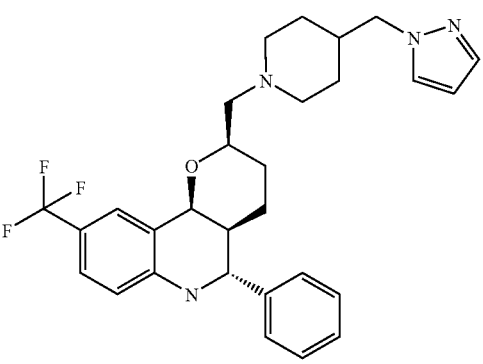

-continued
I323
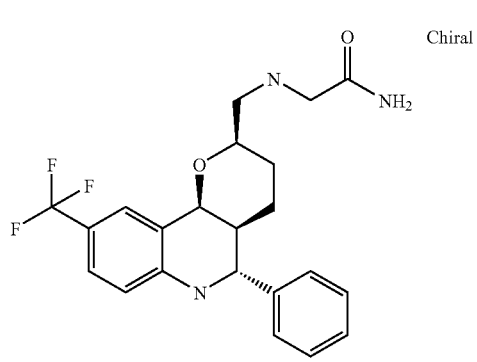
I324
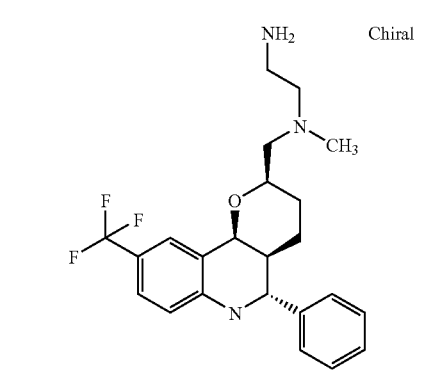
I325
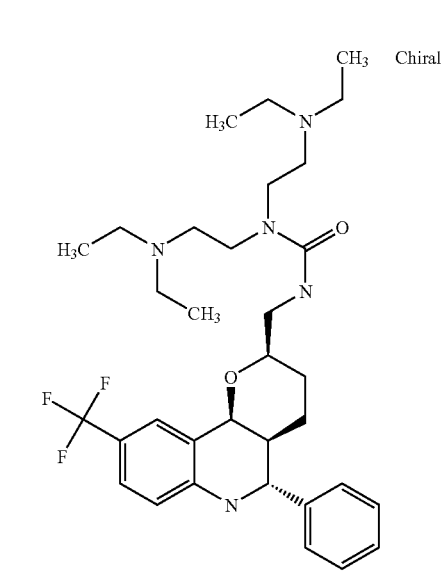
I326
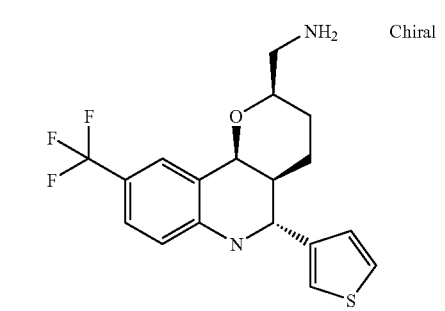
-continued
I327
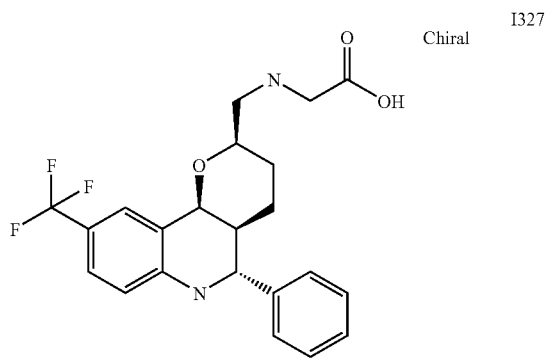
I328
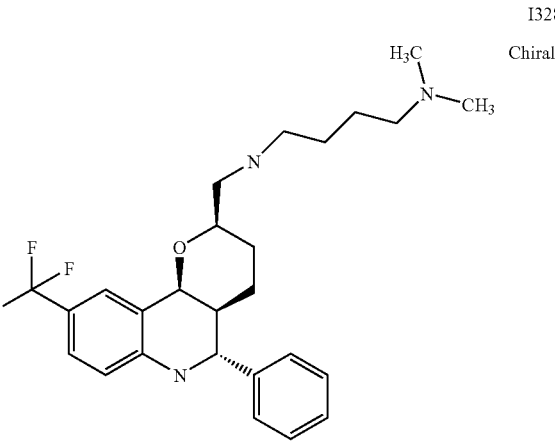
I329
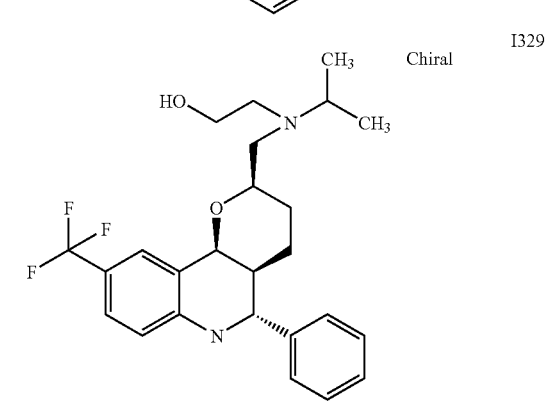
I330
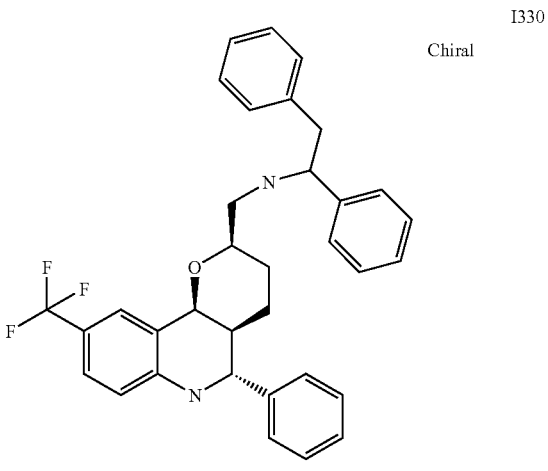

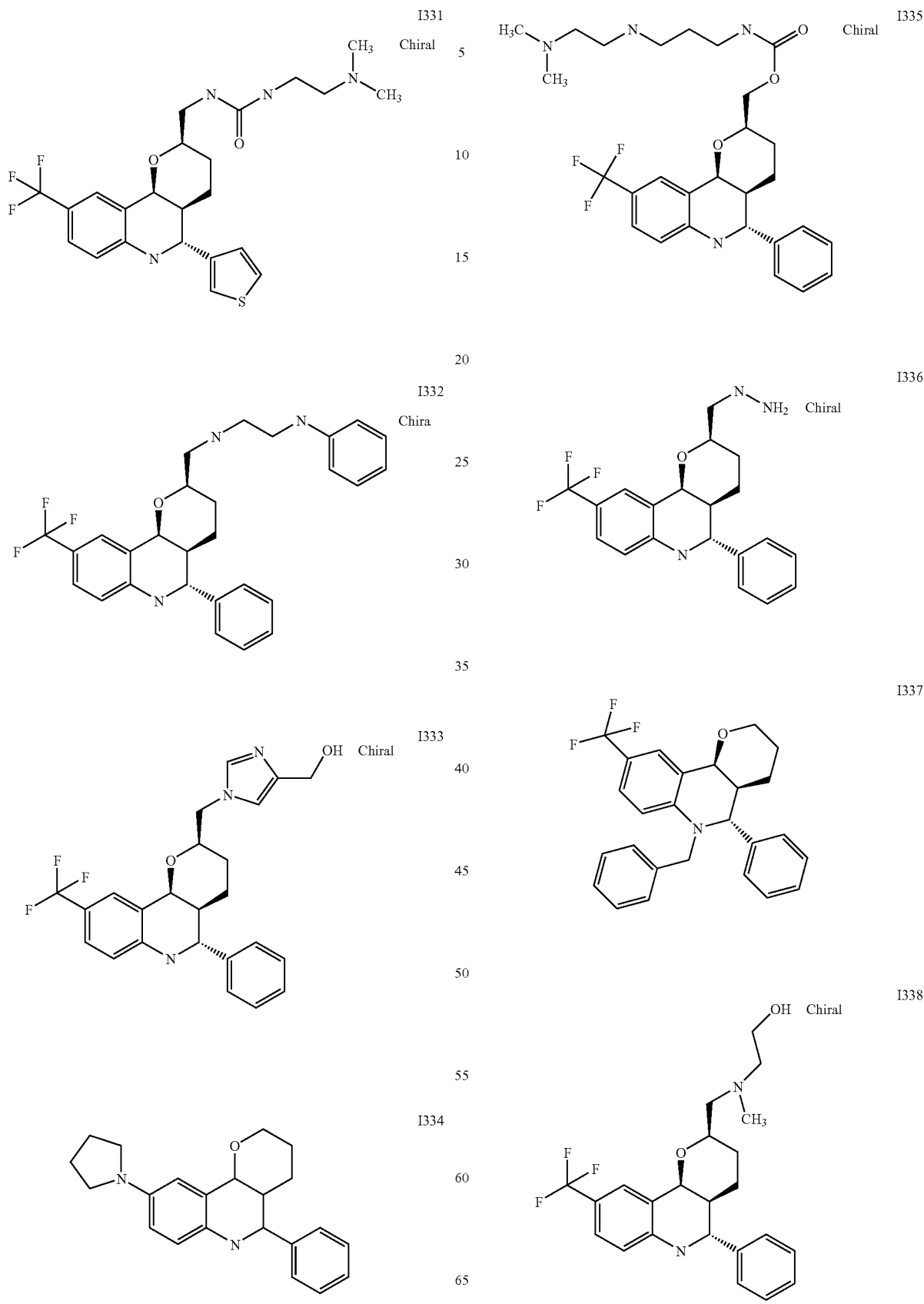

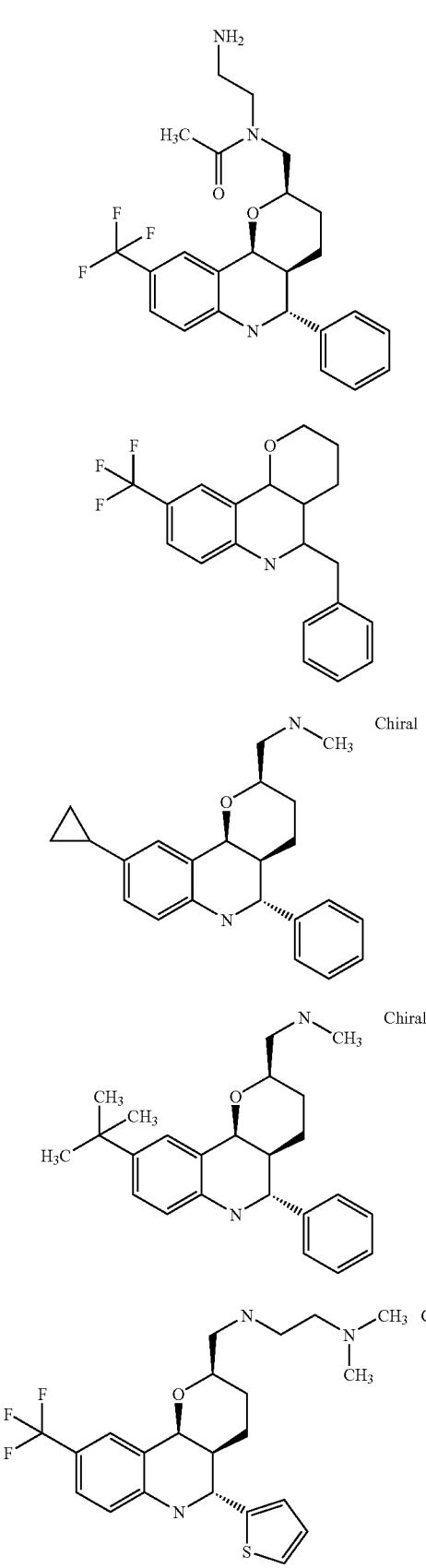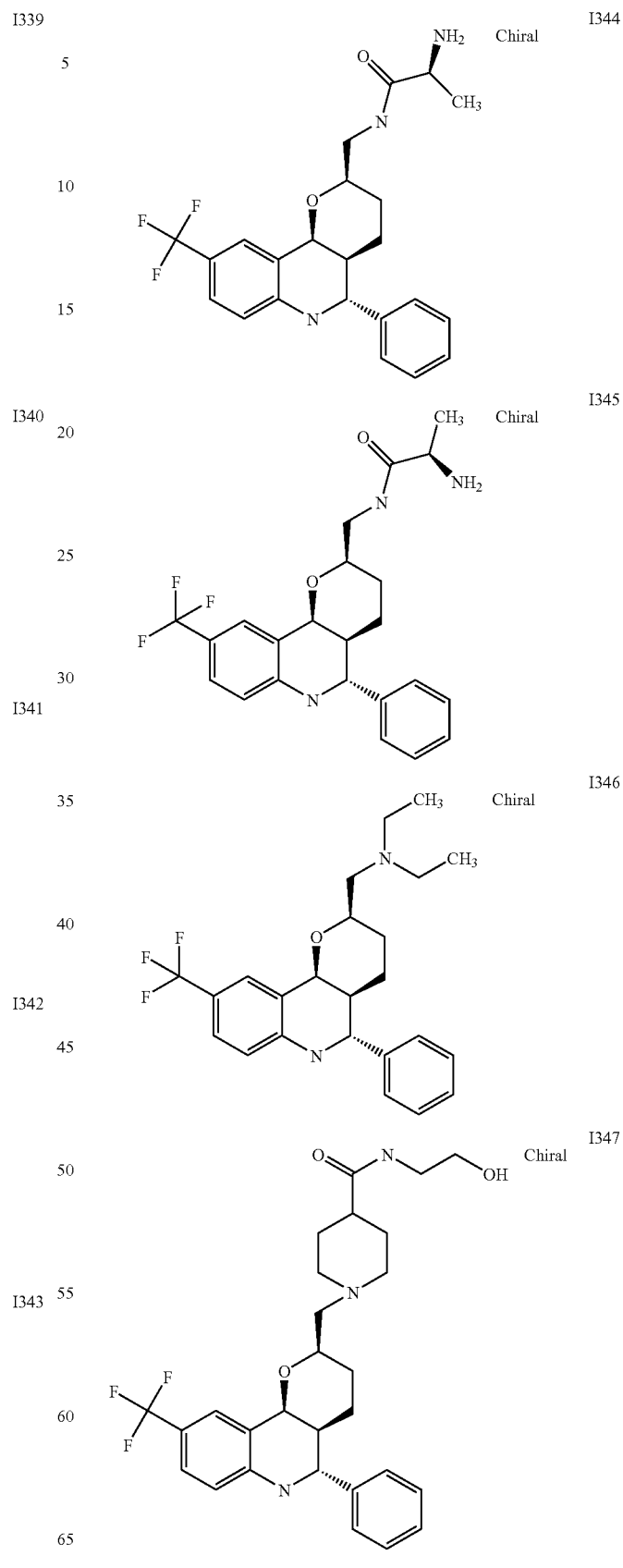

-continued
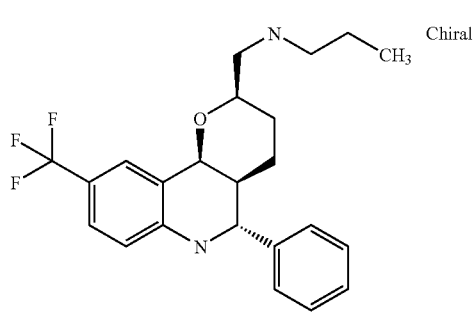 I348
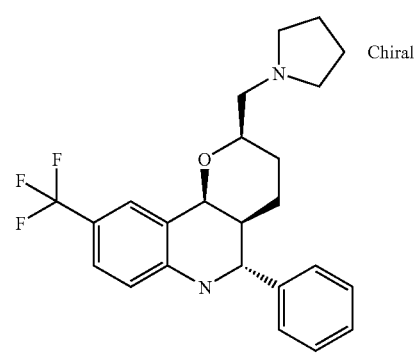 I349
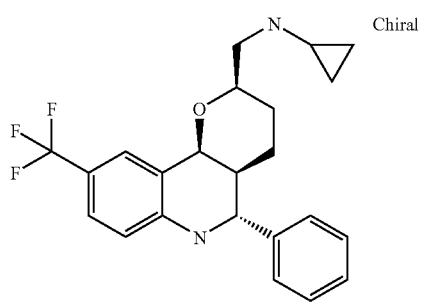 I350
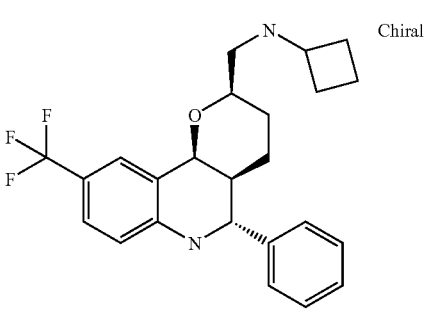 I351
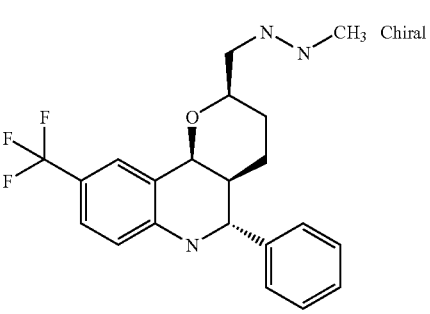 I352
-continued
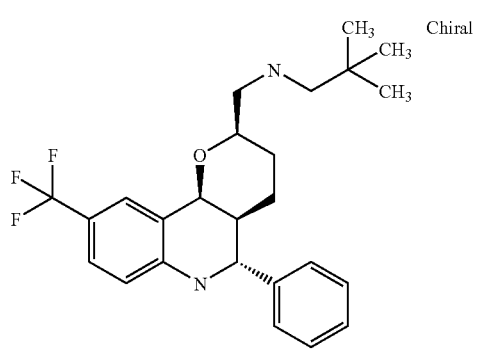 I353
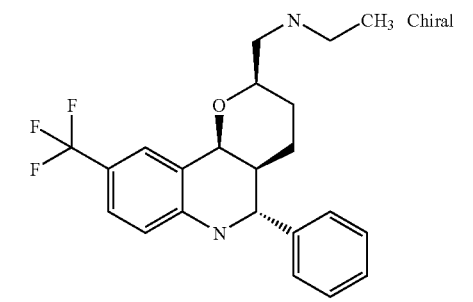 I354
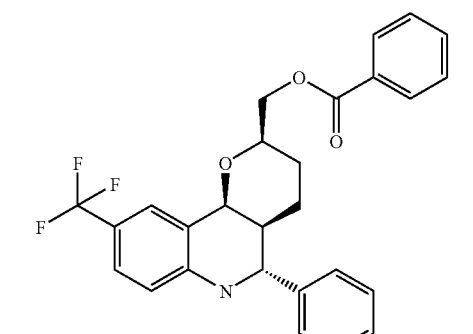 I355
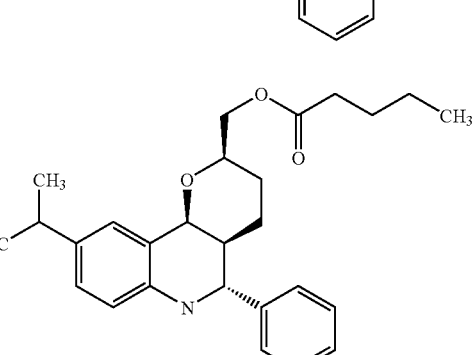 I356
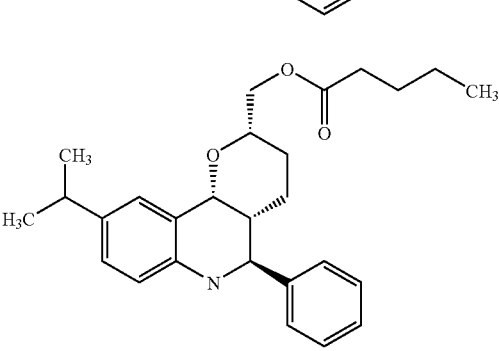 I357

109 110
-continued
I358 Chiral
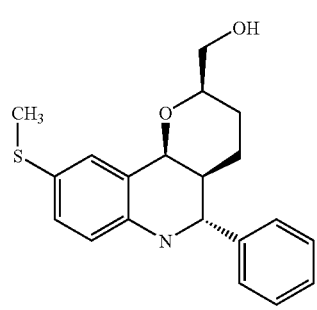
I359 Chiral
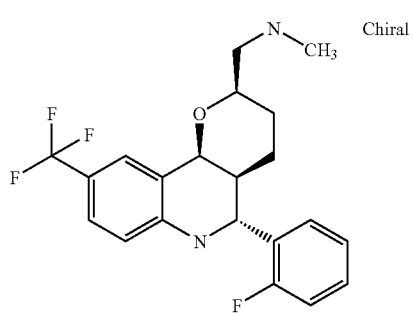
I360 Chiral
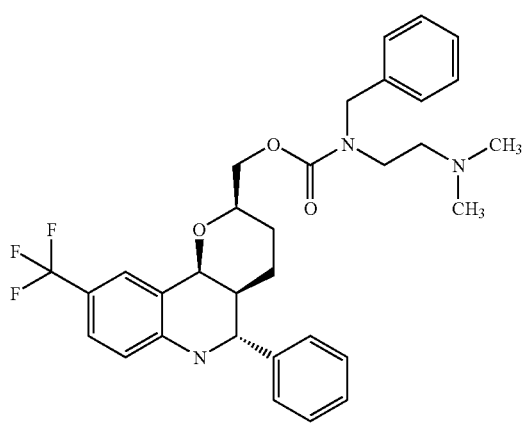
I361
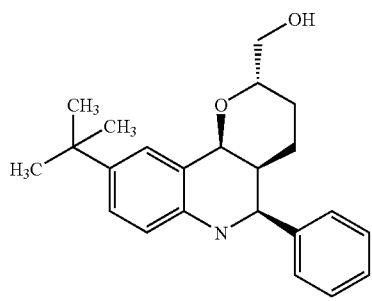
-continued
I362 Chiral
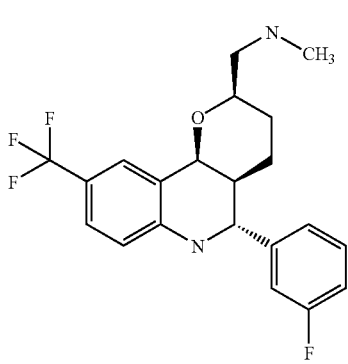
I363 Chiral
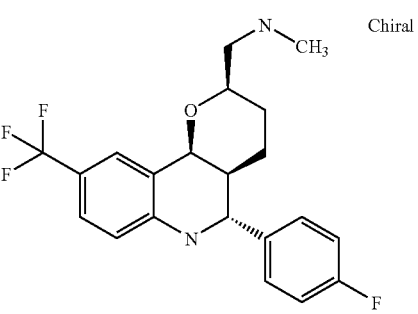
I364 Chiral
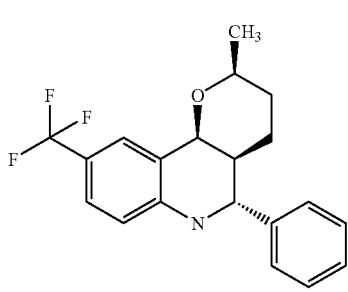
I365 Chiral
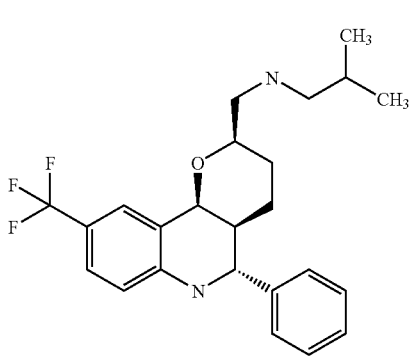
I366 Chiral
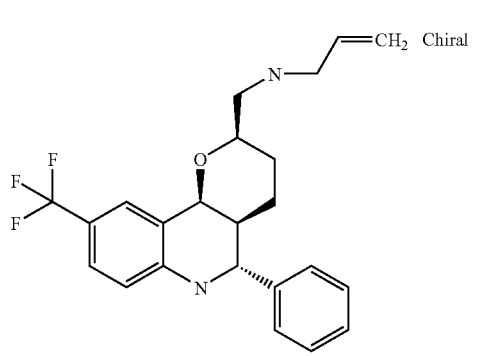

-continued
I367
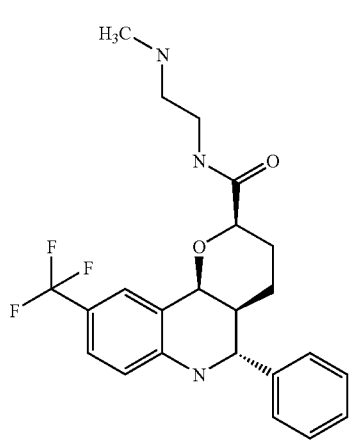
I368
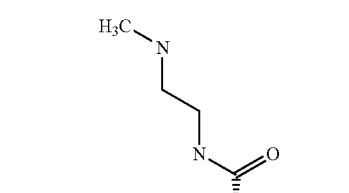
I369 Chiral
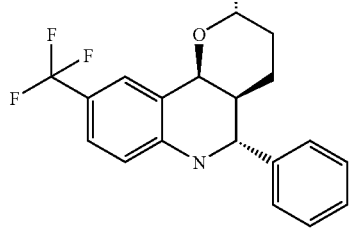
I370 Chiral
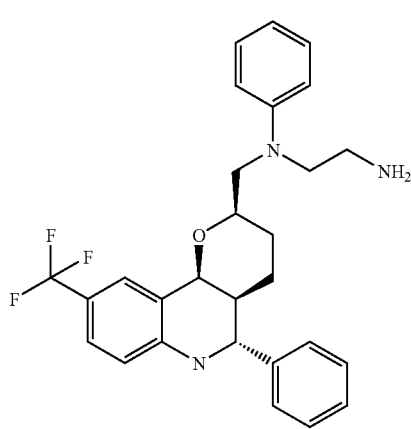
-continued
I371 Chiral
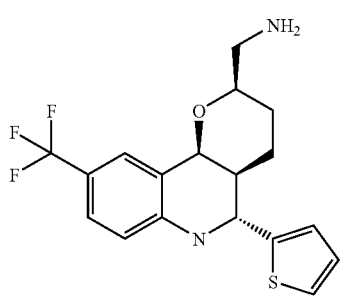
I372 Chiral
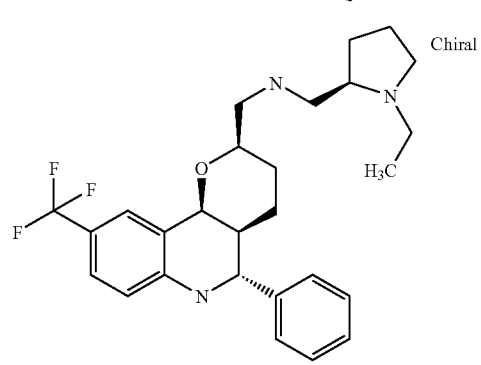
I373 Chiral
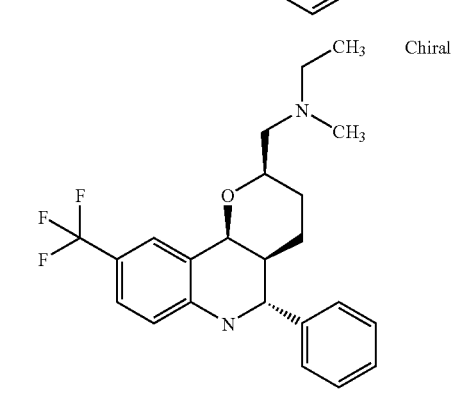
I374 Chiral
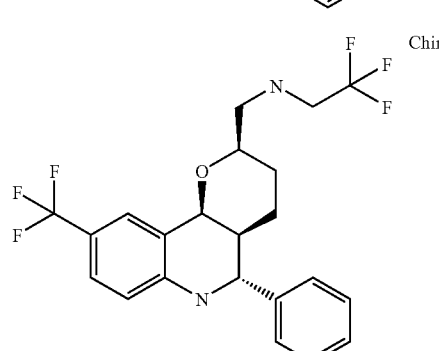
I375 Chiral
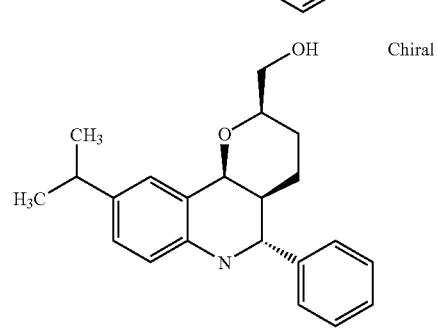

-continued
I376 Chiral
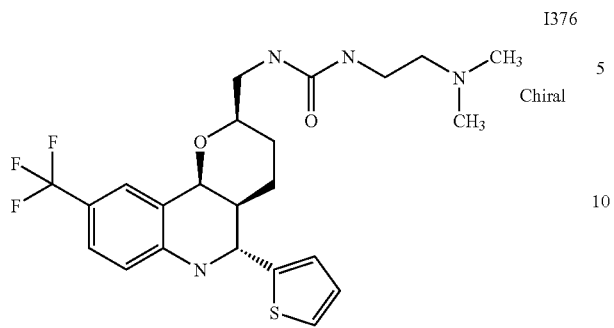
I377
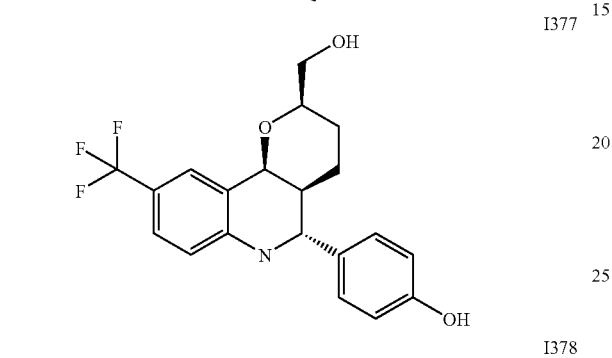
I378 Chiral
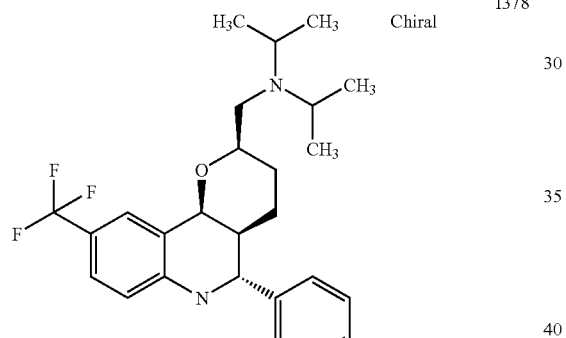
I379
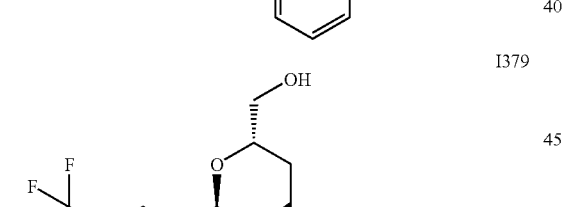
I380 Chiral
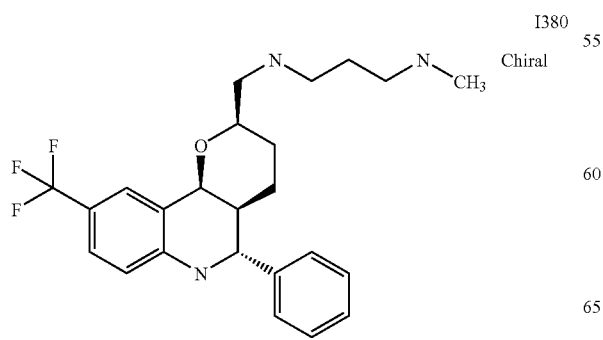
-continued
I381
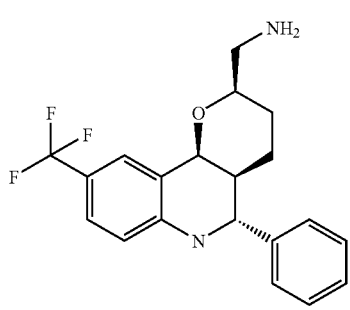
I382 Chiral
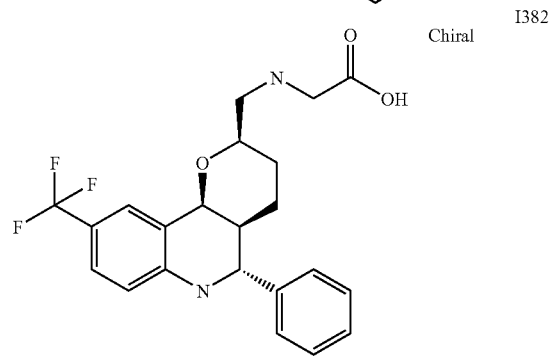
I383 Chiral
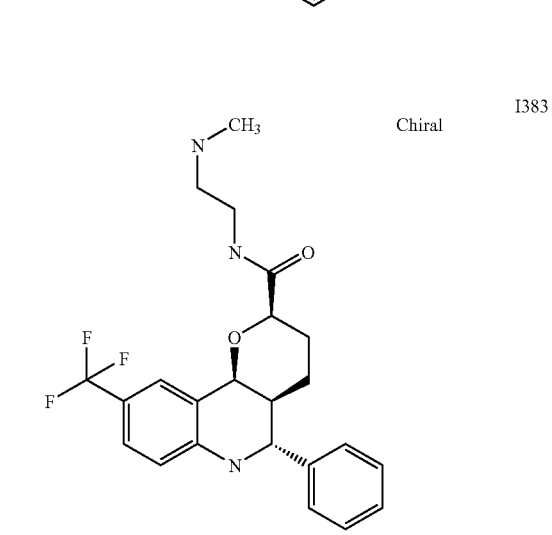
I384 Chiral
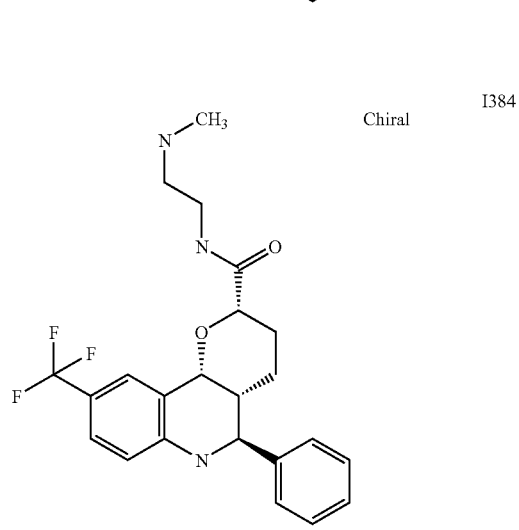

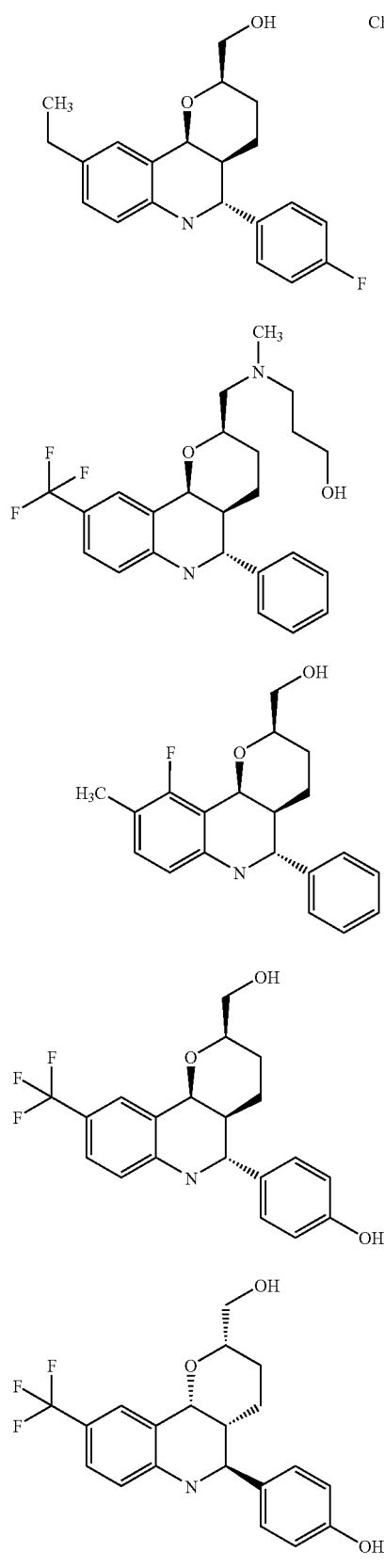
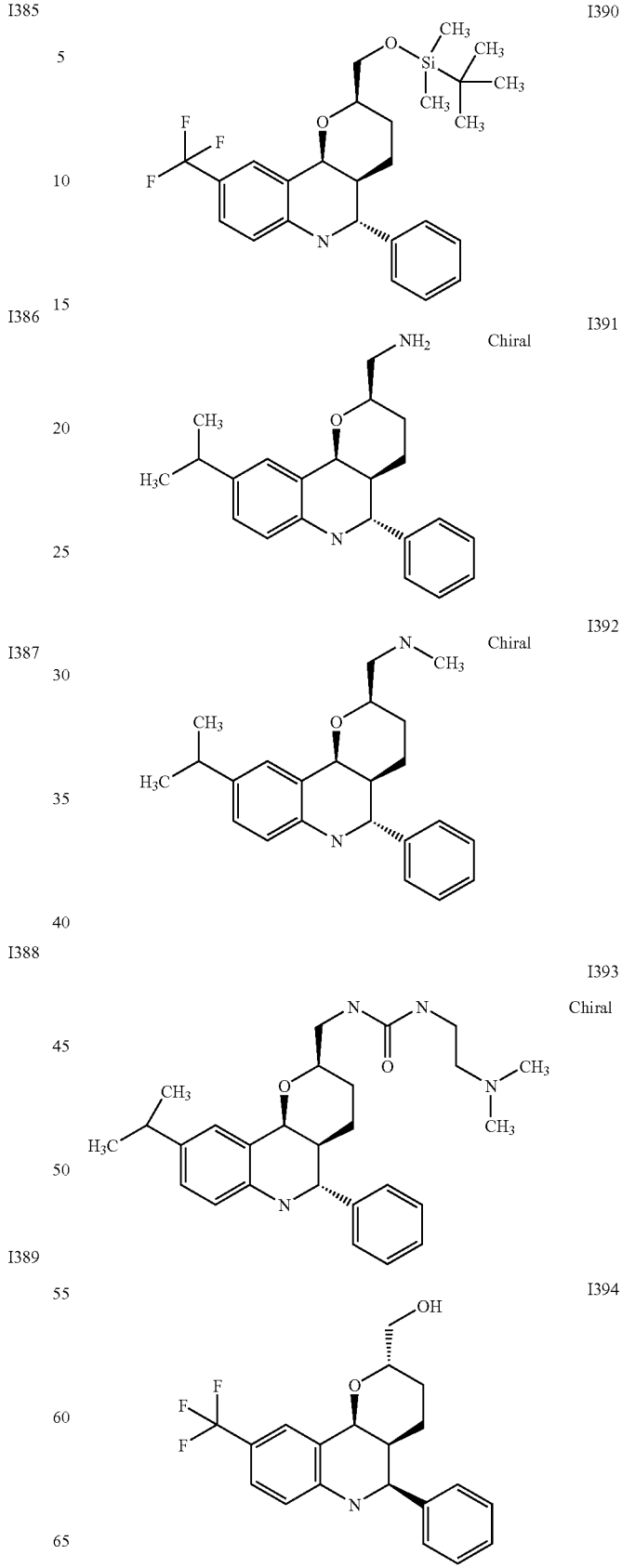

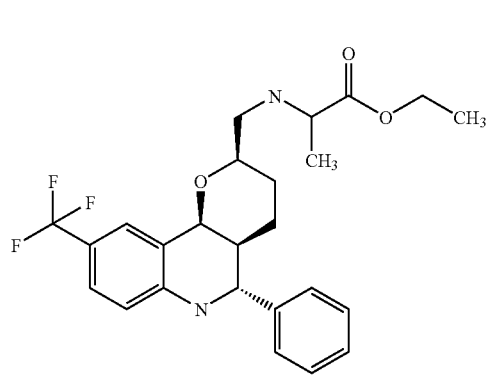
I395 Chiral
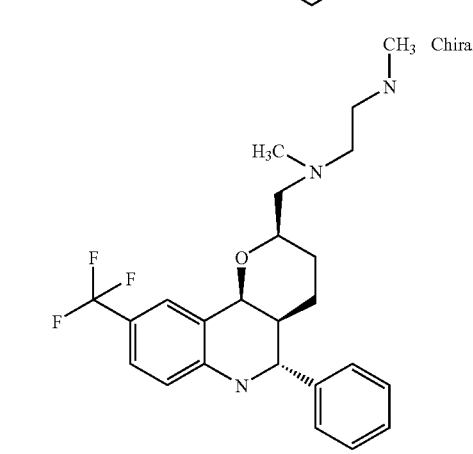
I396 Chiral
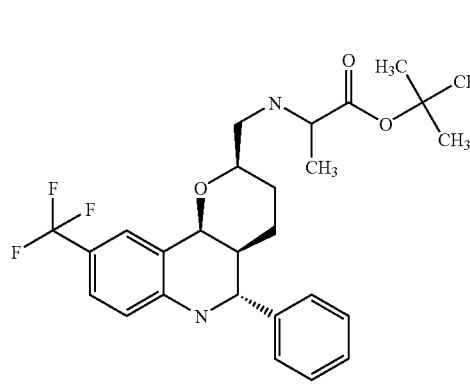
I397 Chiral
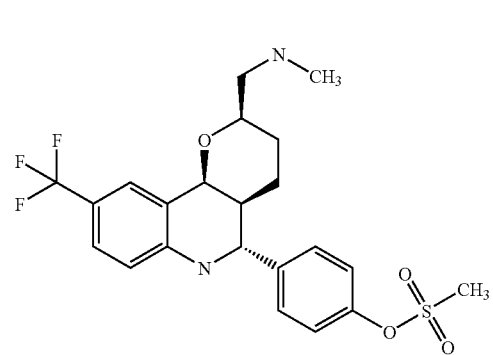
I398 Chiral
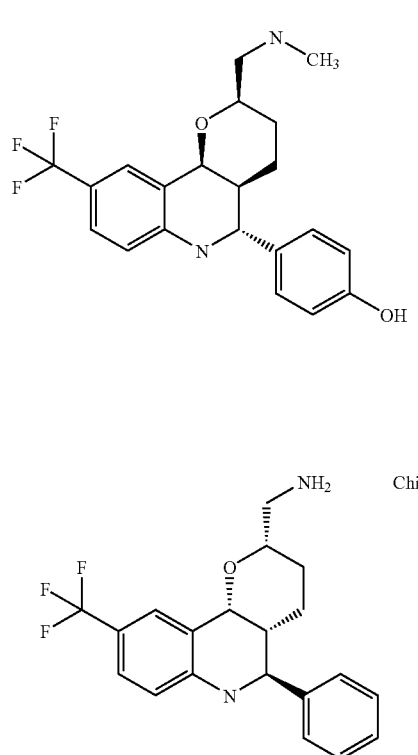
I399 Chiral
I400 Chiral
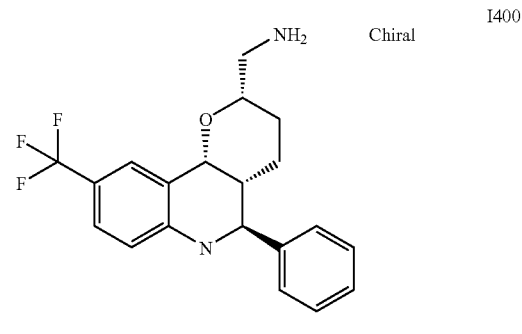
I401 Chiral
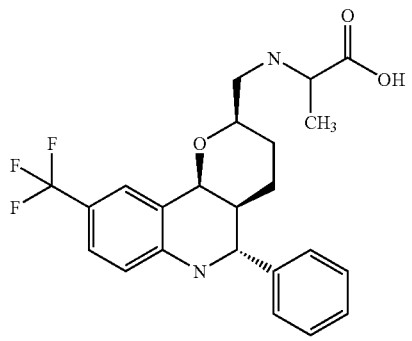
I402
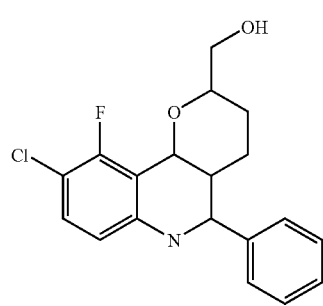

-continued
I403
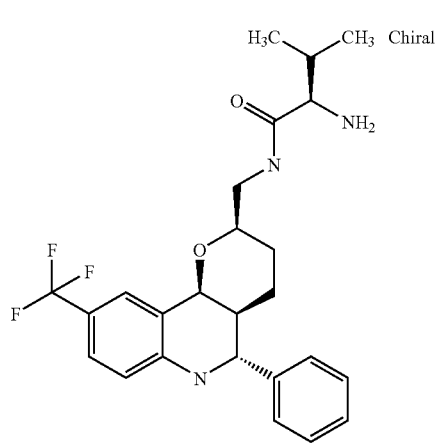
I404
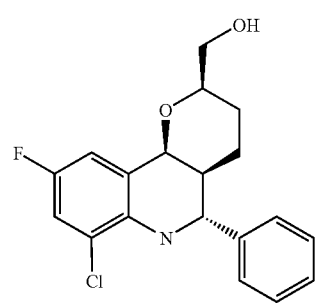
I405
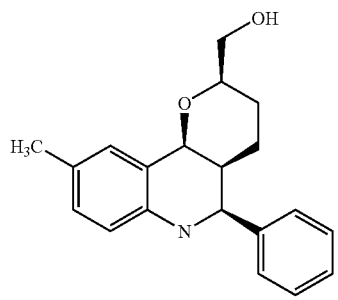
I406
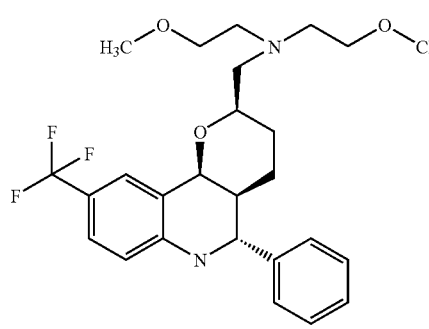
-continued
I407
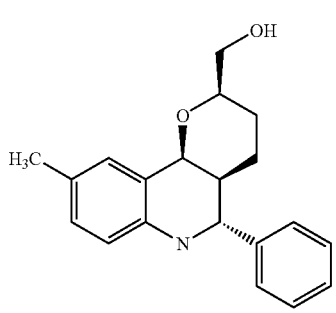
I408
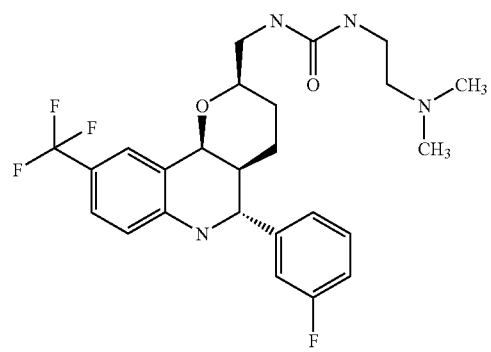
I409
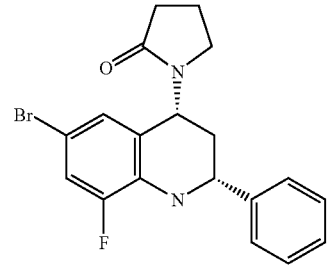
I410
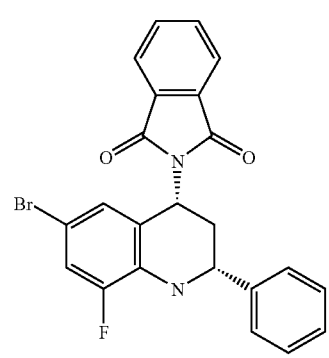
I411
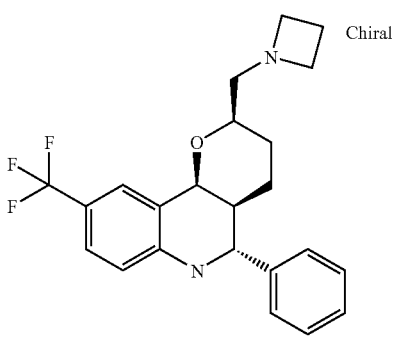

-continued
I412
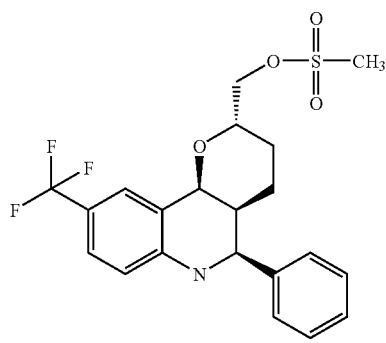
I413
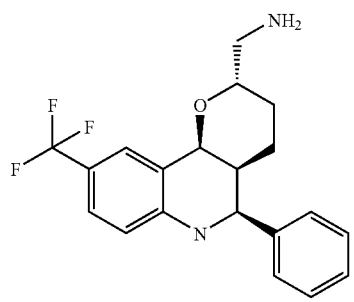
I414
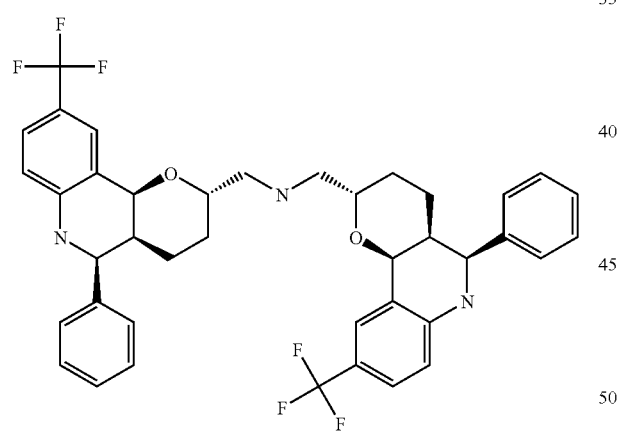
I415 Chiral
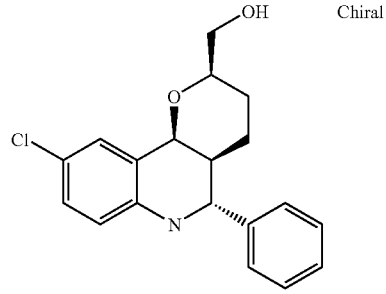
-continued
I416 Chiral
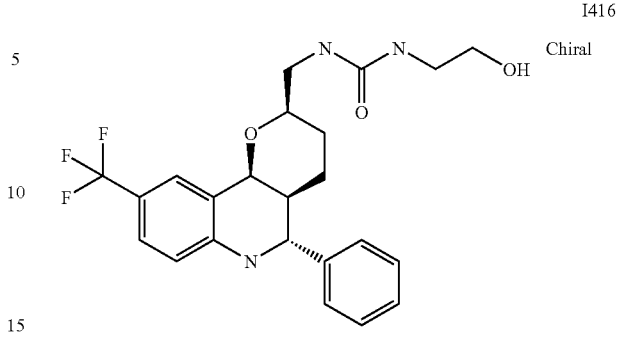
I417 Chiral
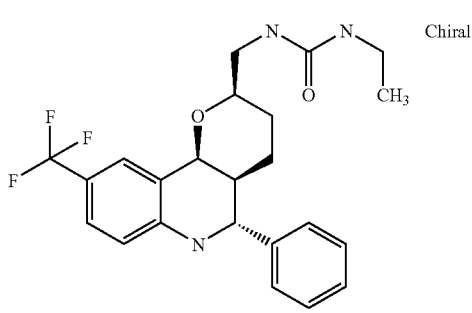
I418 Chiral
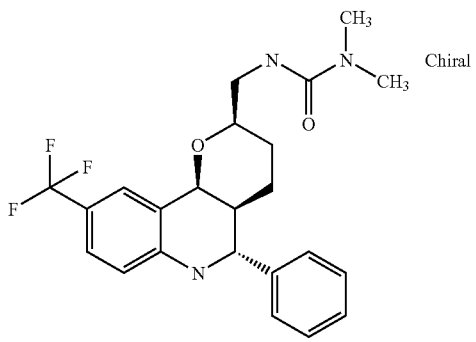
I419 Chiral
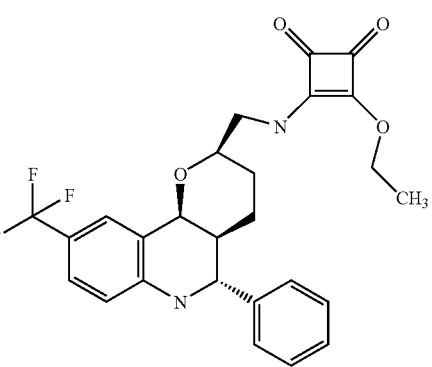

-continued
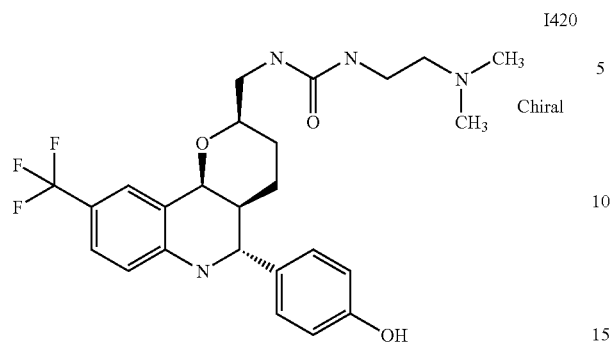
I420
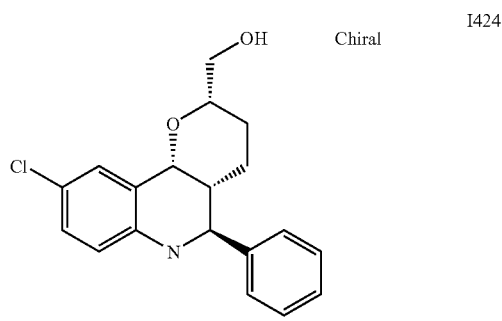
I424
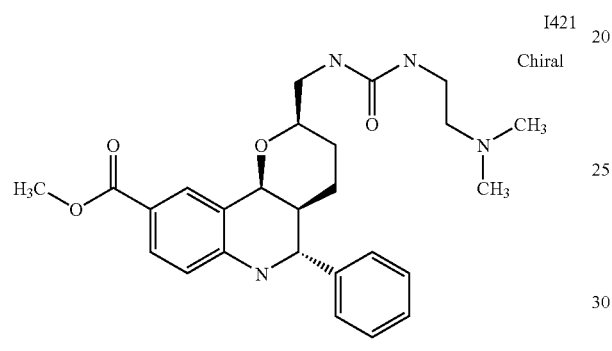
I421
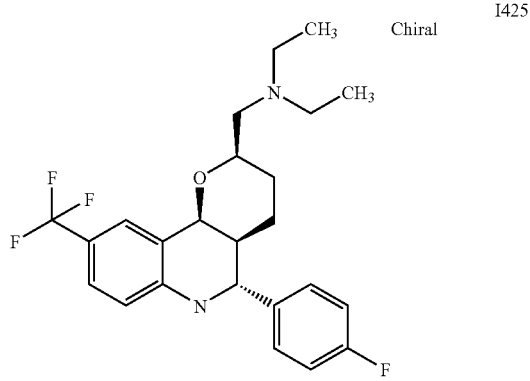
I425
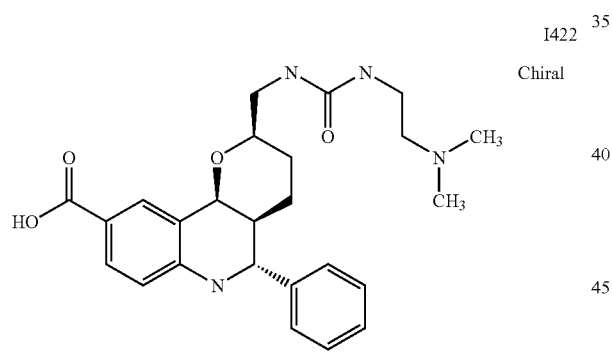
I422
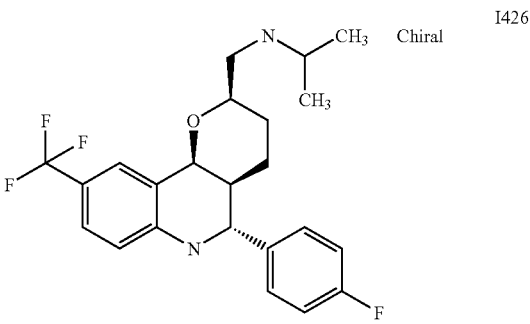
I426
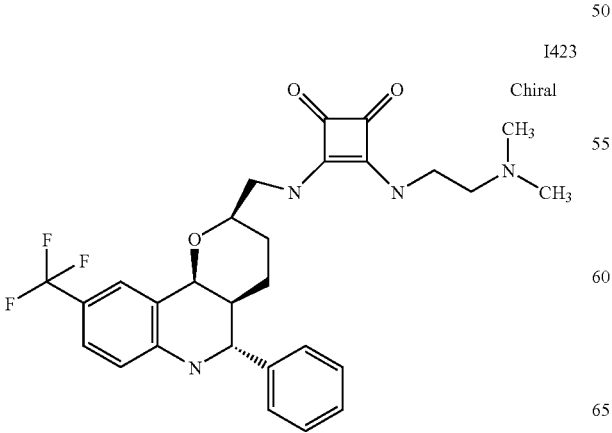
I423
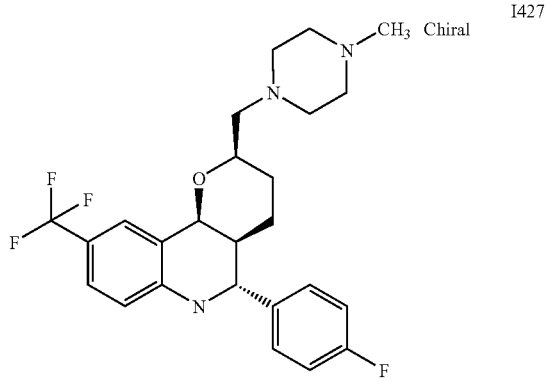
I427

-continued
I428
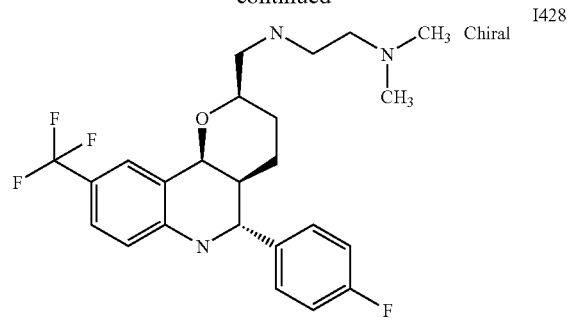
I429
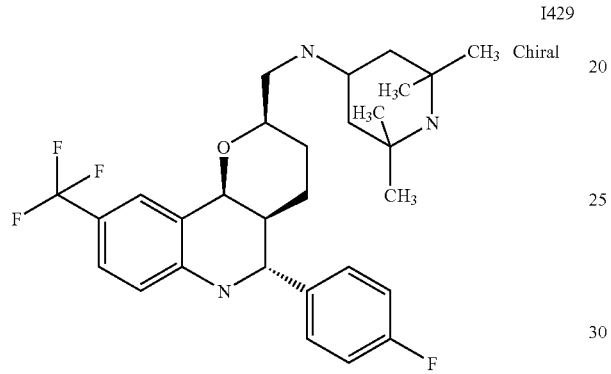
I430
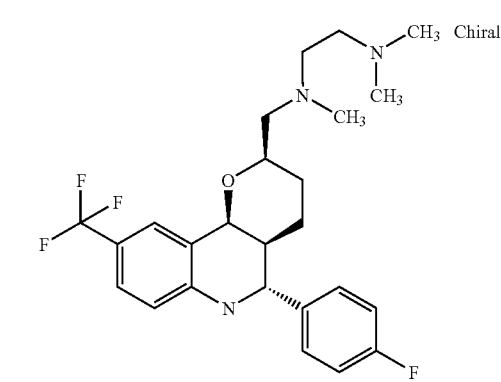
I431
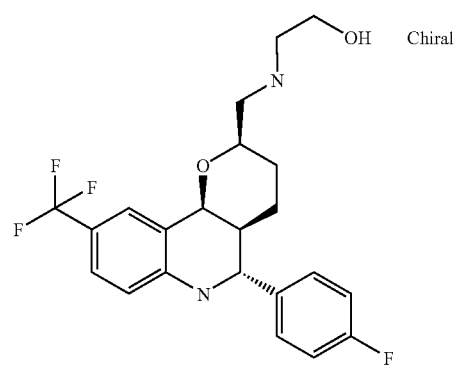
-continued
I432
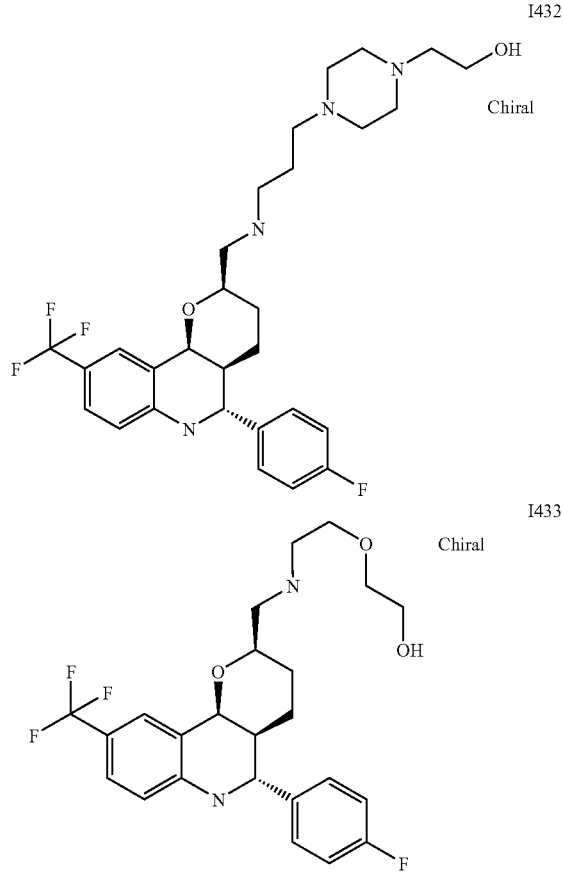
I433
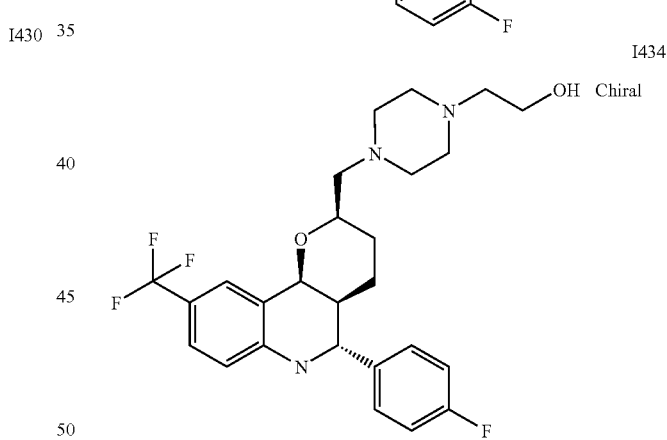
I434
I435
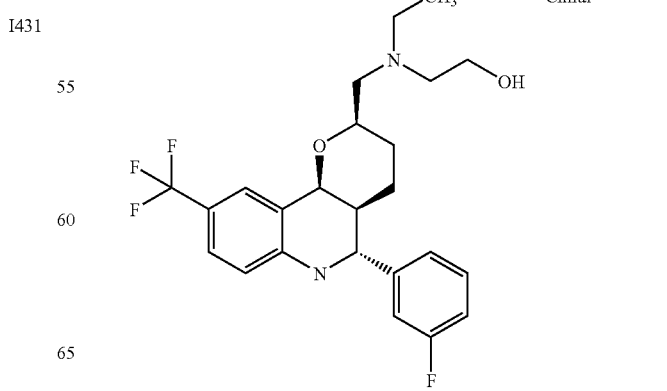

-continued
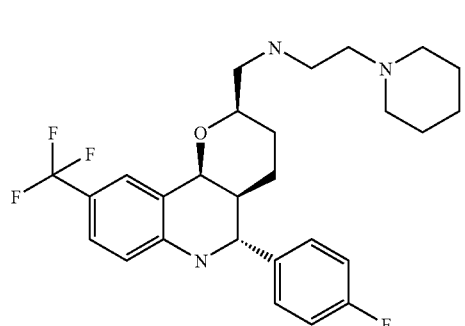
I436 Chiral
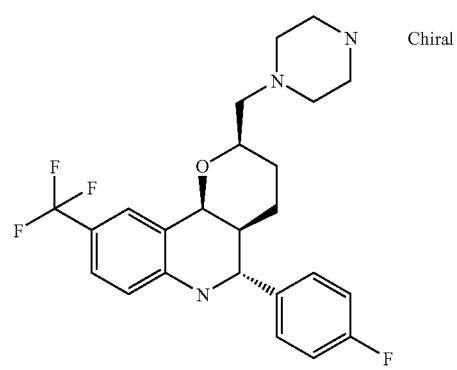
I437 Chiral
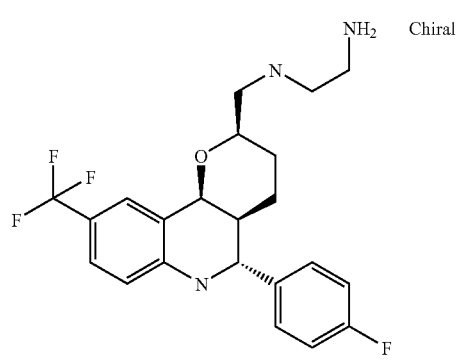
I438 Chiral
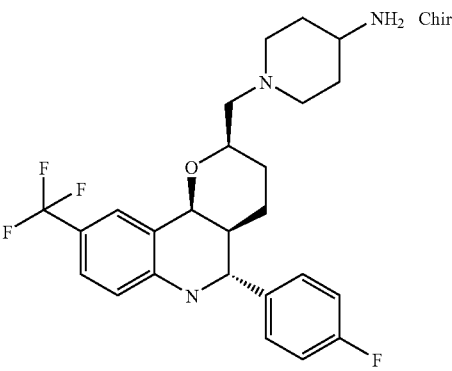
I439 Chiral
-continued
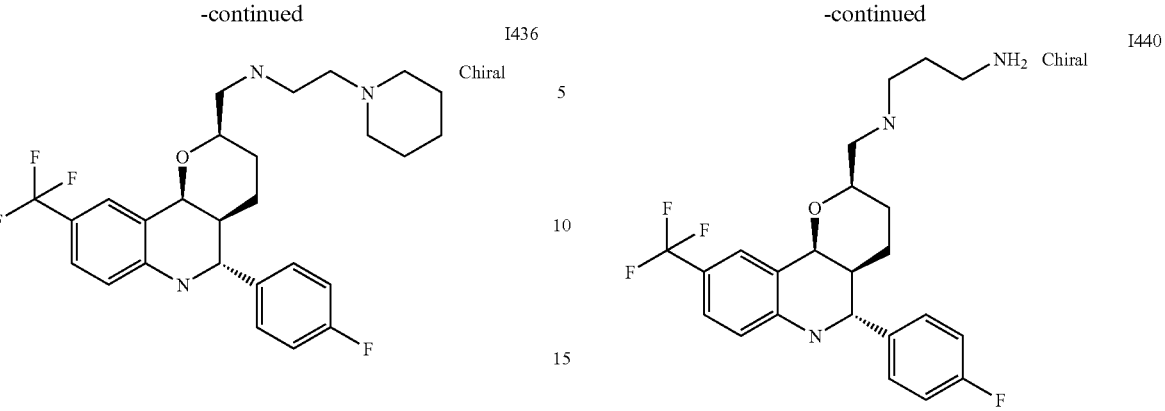
I440 Chiral
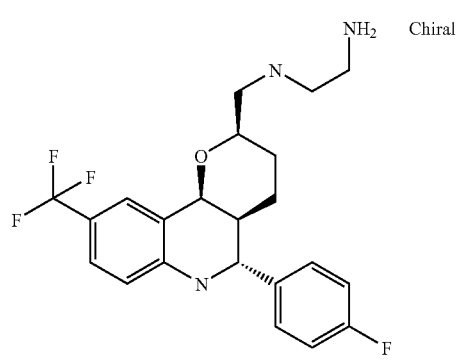
I441 Chiral
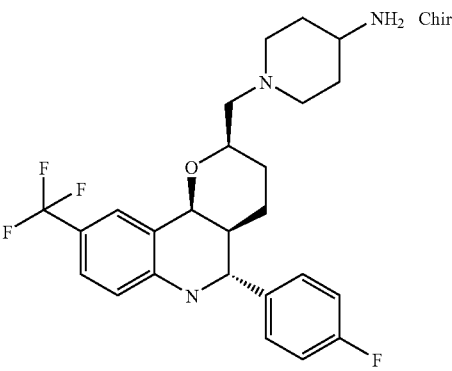
I442 Chiral
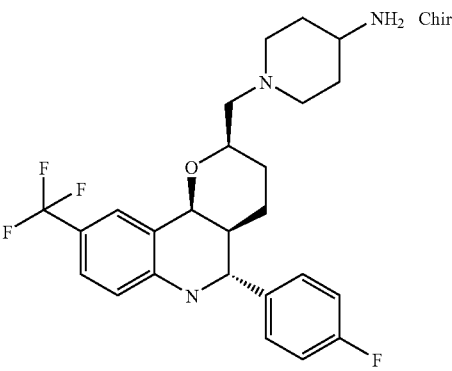
I443 Chiral -continued
I444
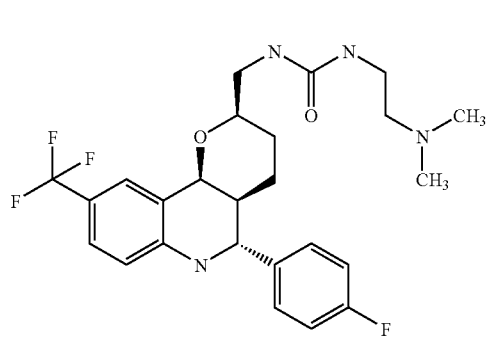
I445
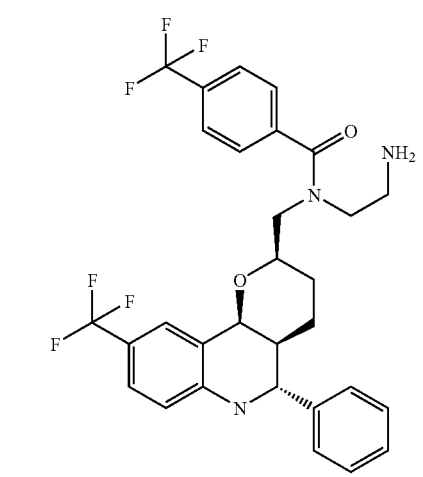
I446
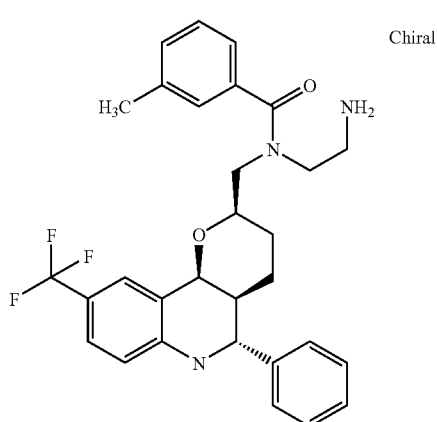
I447
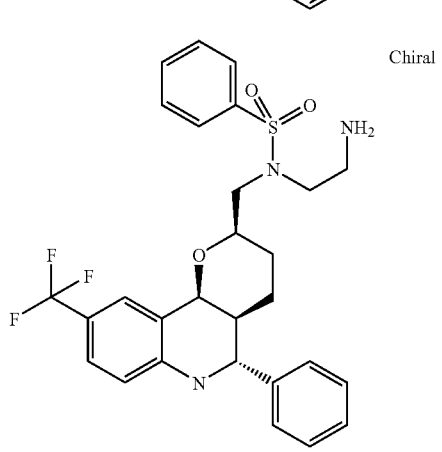
-continued
I448
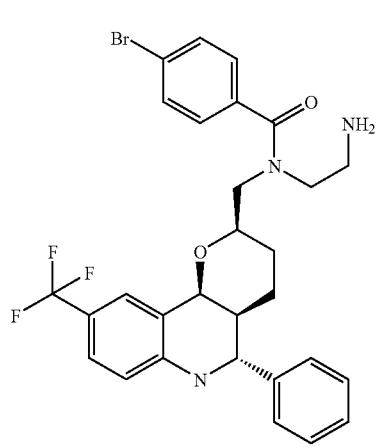
I449
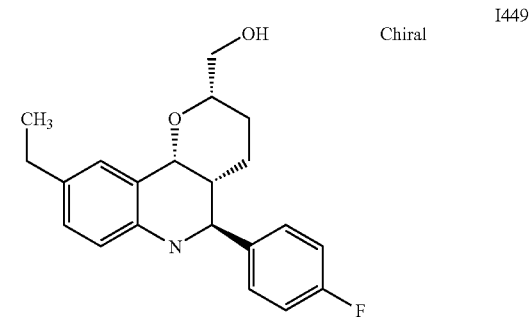
I450
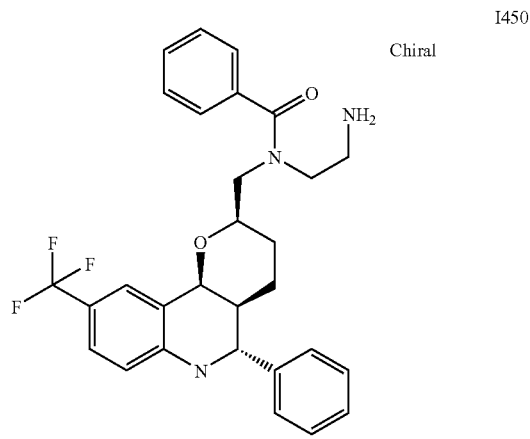
I451
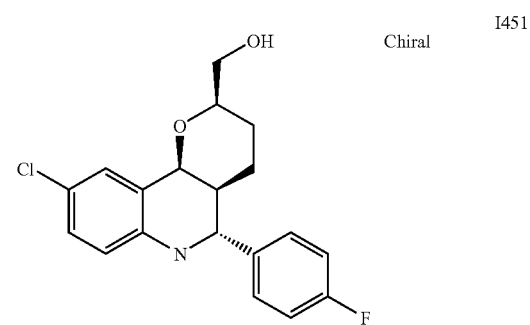

| | |
|---|---|
| 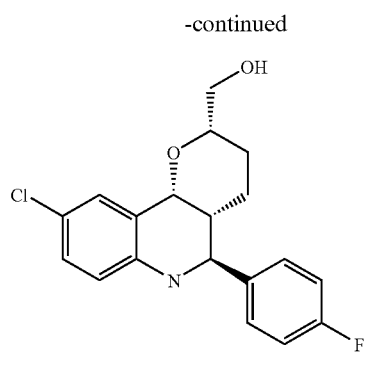 I452 Chiral | 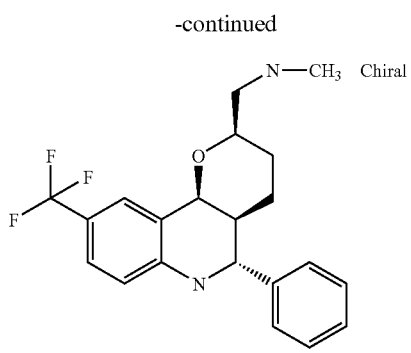 I456 Chiral |
| 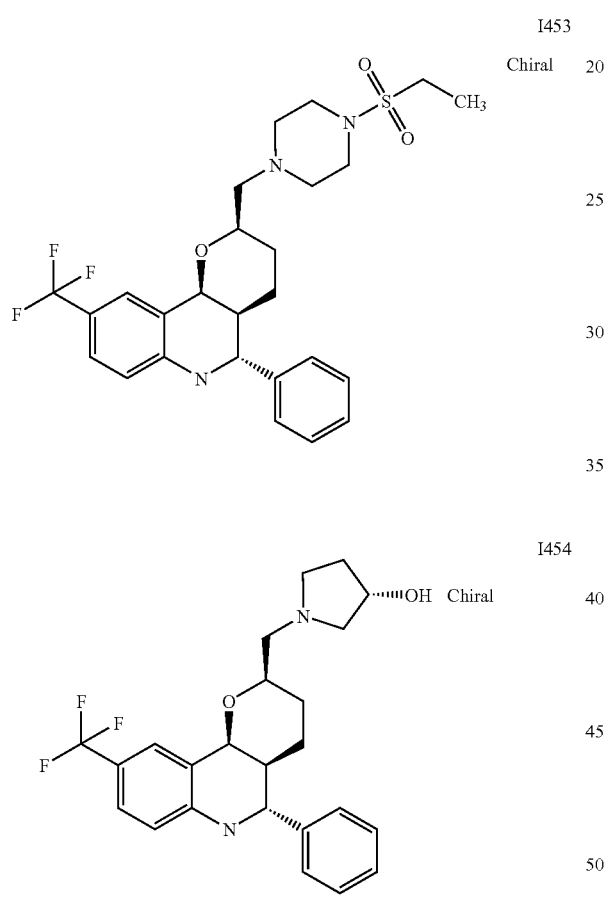 I453 Chiral<br><br>I454 Chiral<br><br>I455 Chiral | 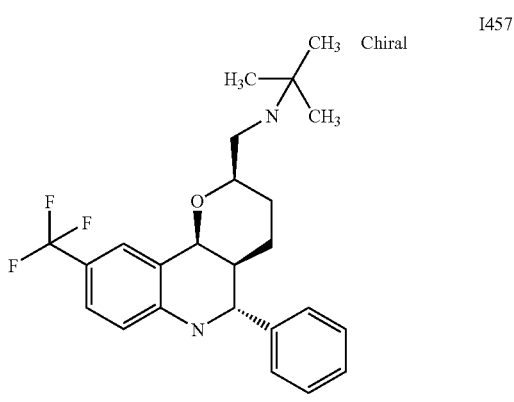 I457 Chiral<br><br>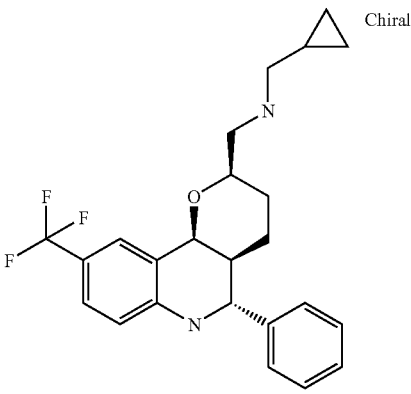 I458 Chiral<br><br>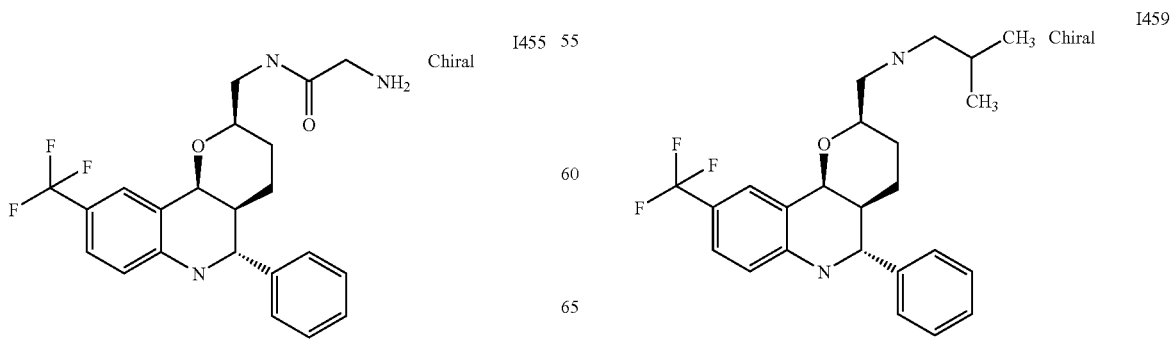 I459 Chiral |

-continued
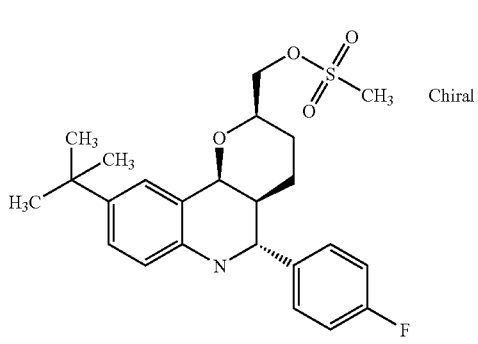
I460
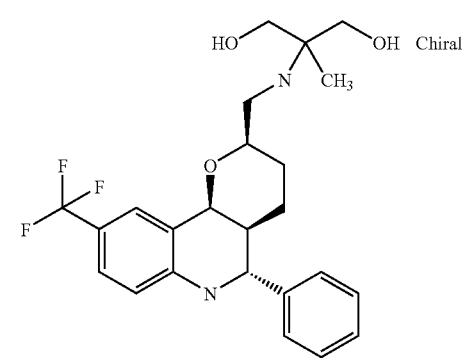
I461
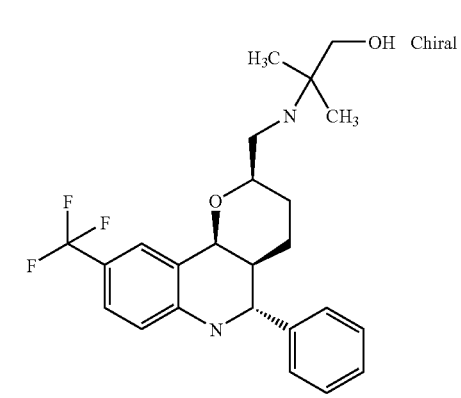
I462
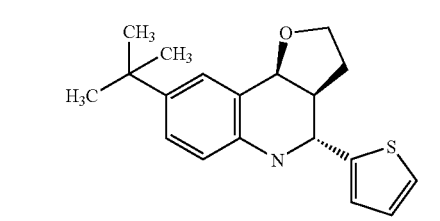
I463
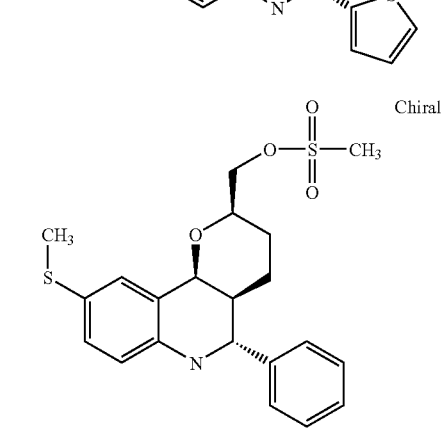
I464
-continued
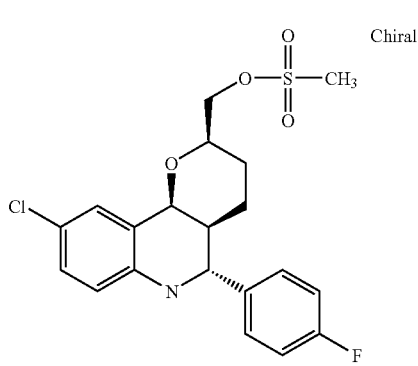
I465
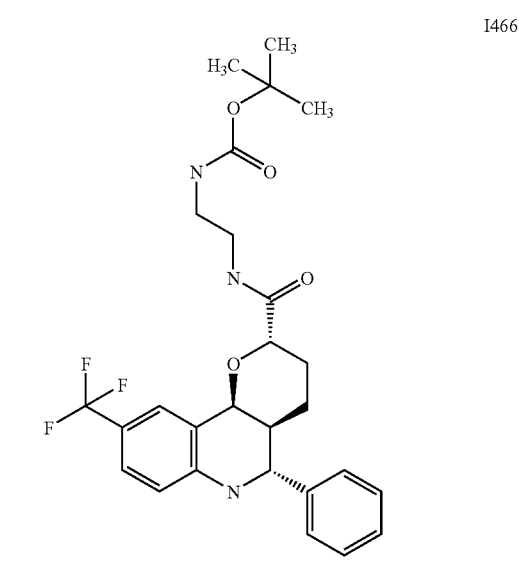
I466
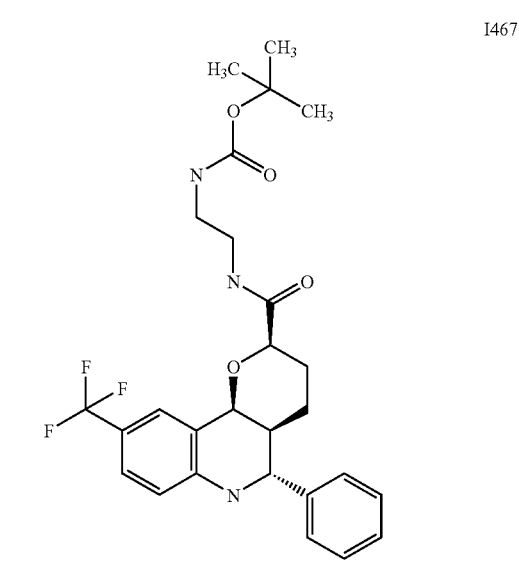
I467

I468
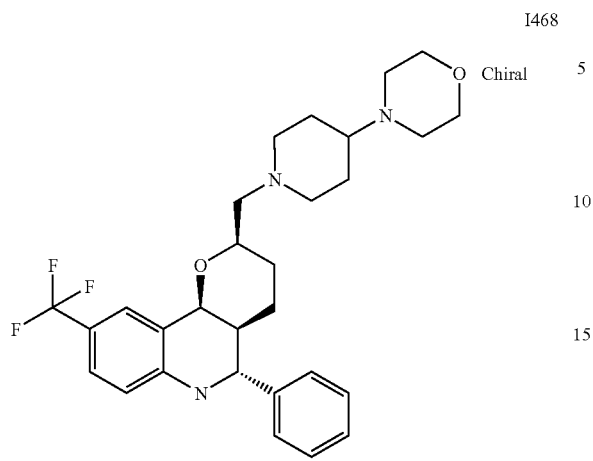
I469
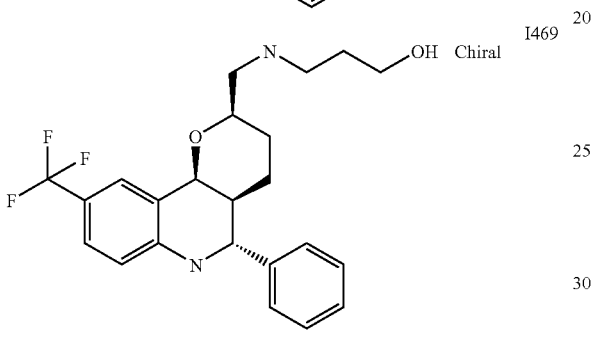
I470
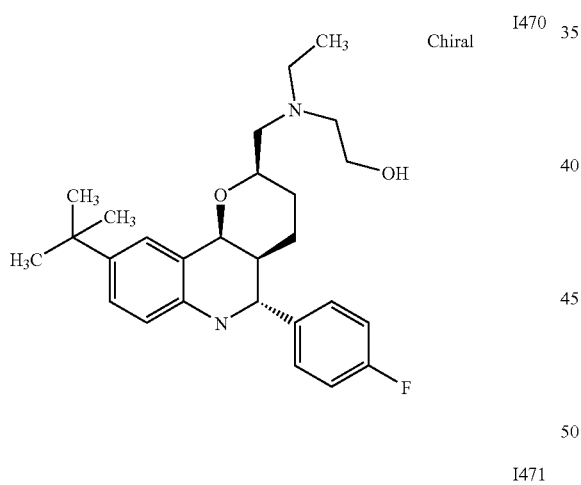
I471
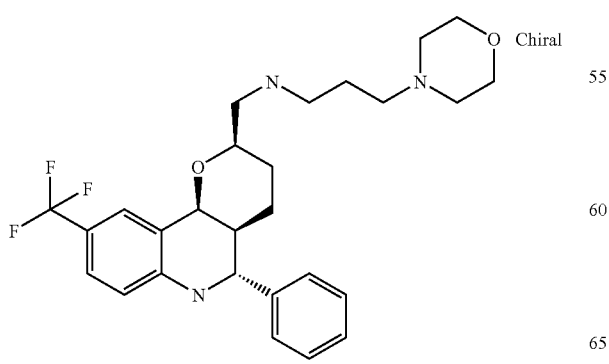
I472
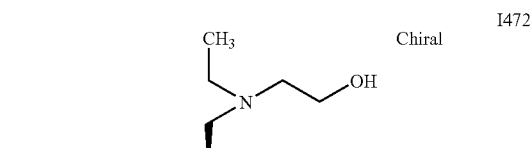
I473
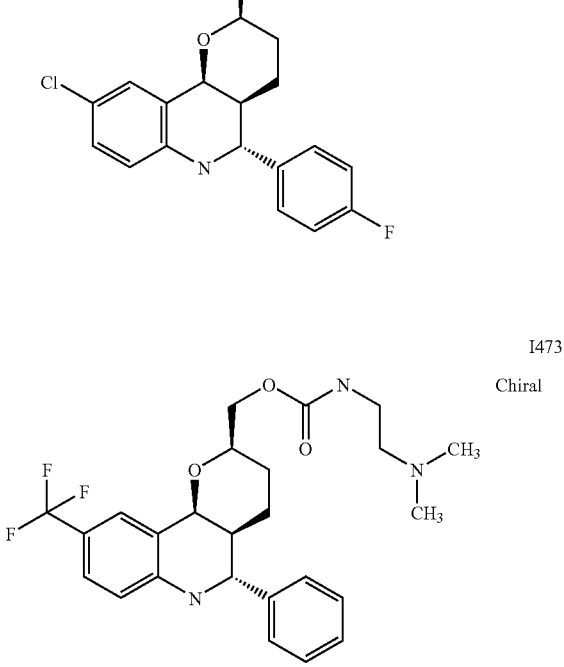
I474
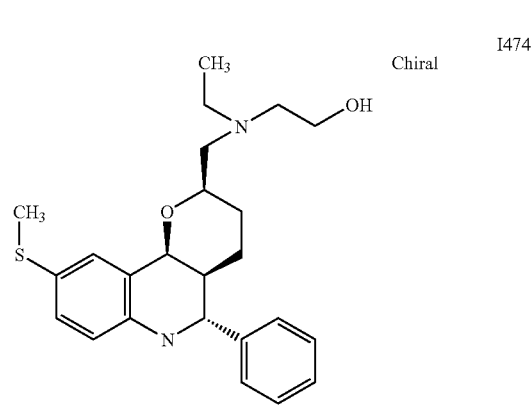
I475
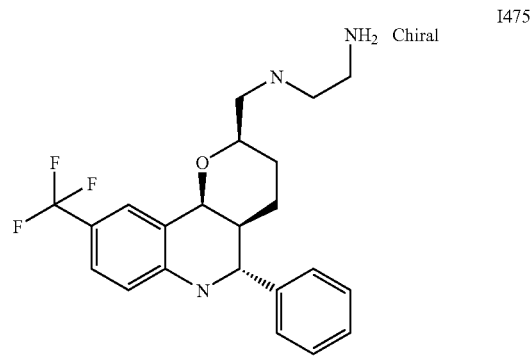

I476
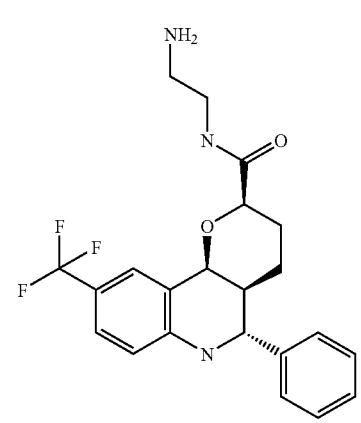
I477 Chiral
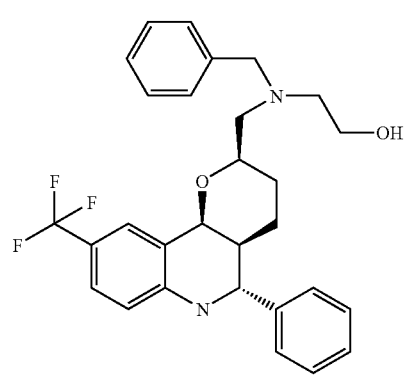
I478
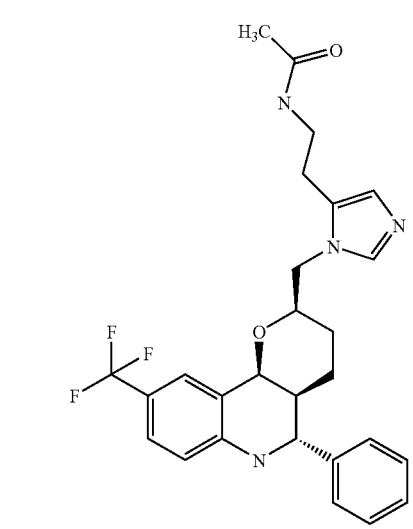
I479
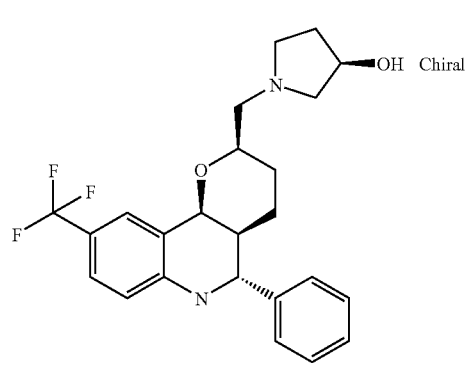
I480 Chiral
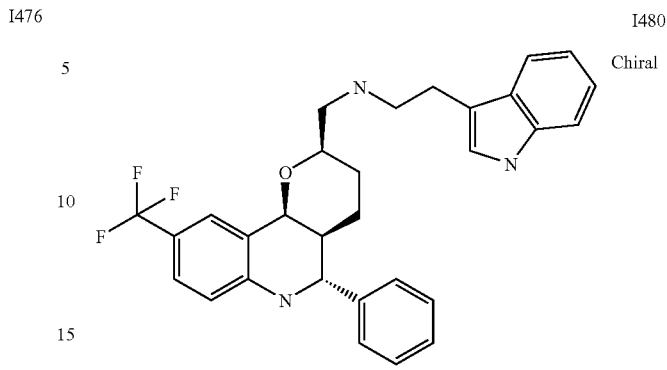
I481 Chiral
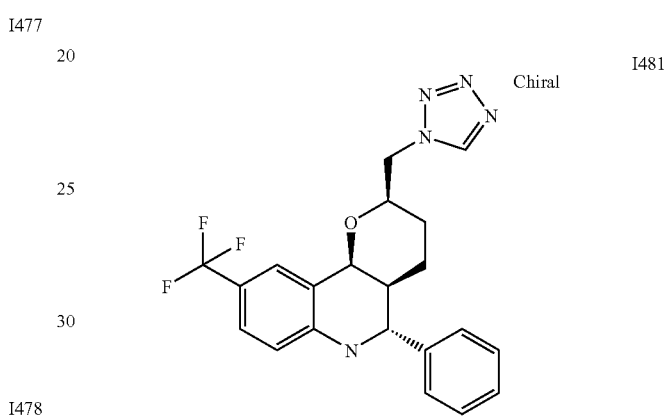
I482 Chiral
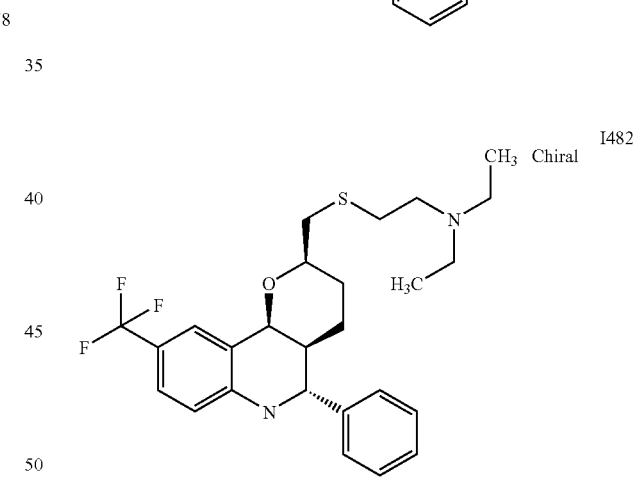
I483 Chiral
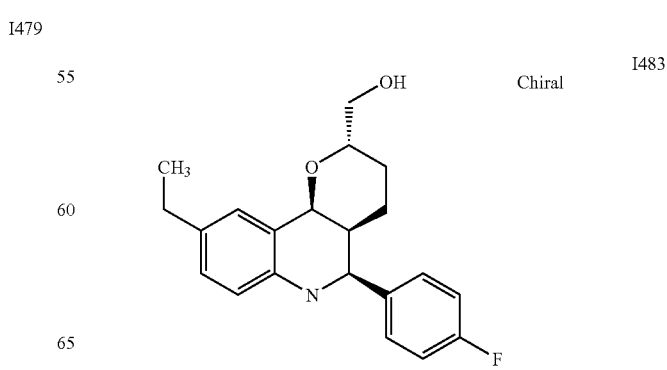

-continued
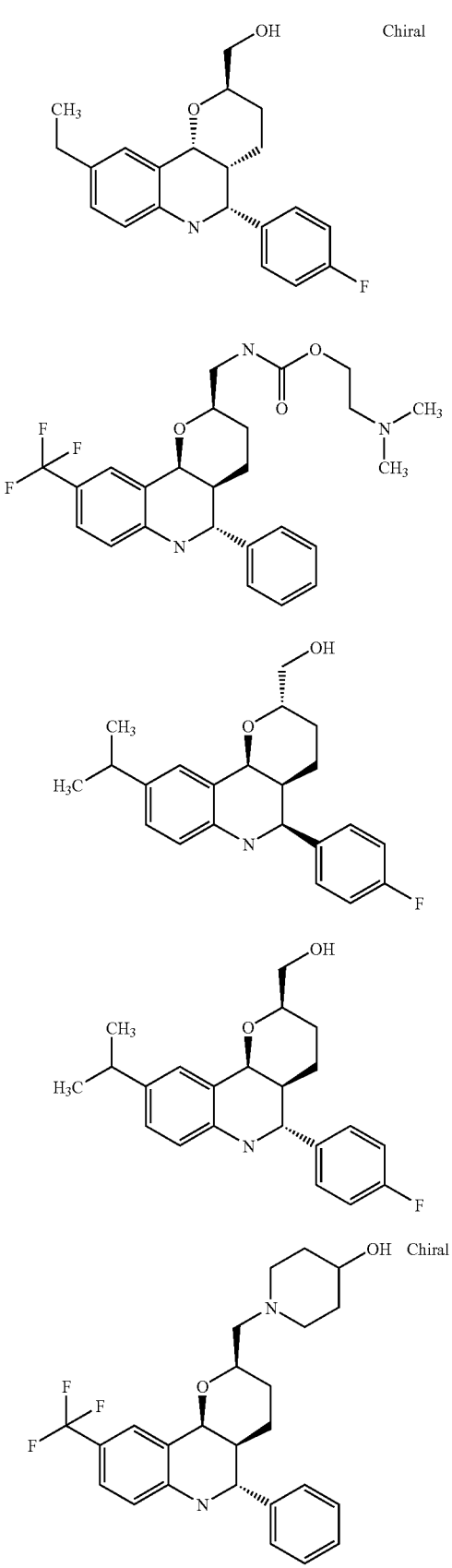
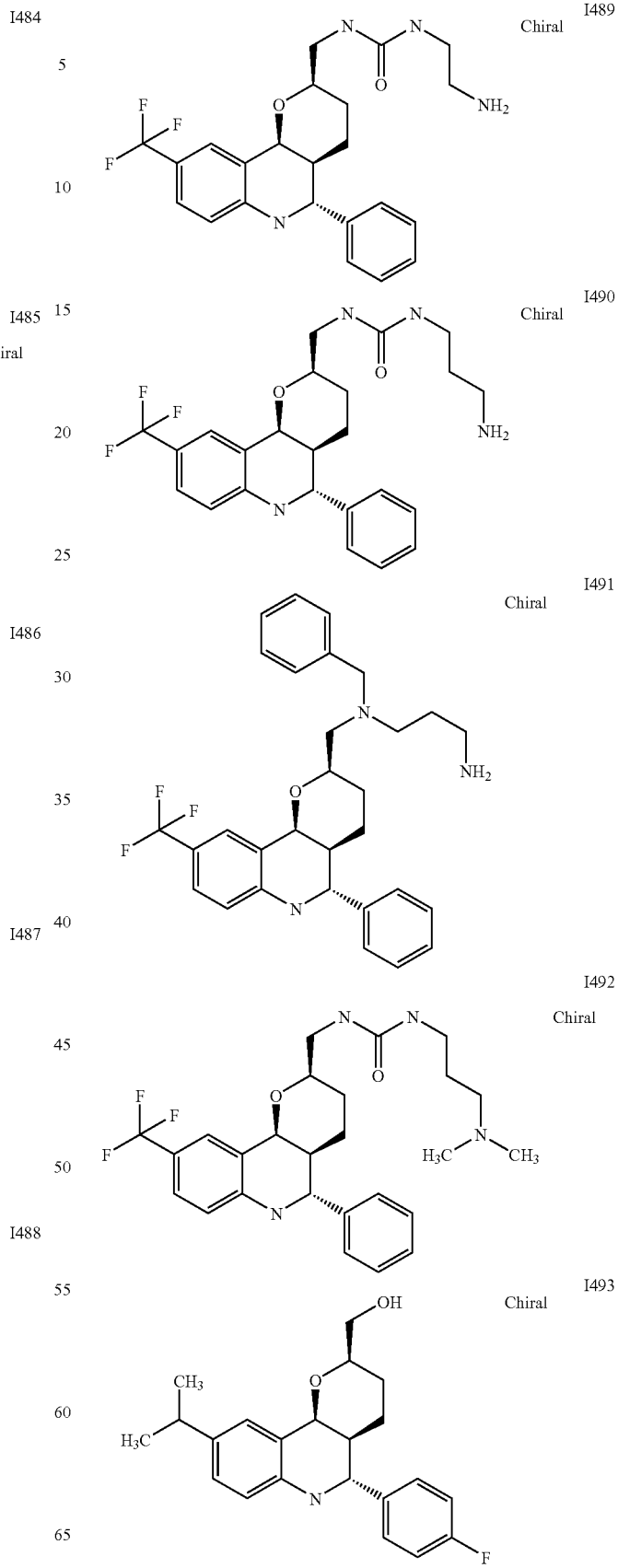

-continued
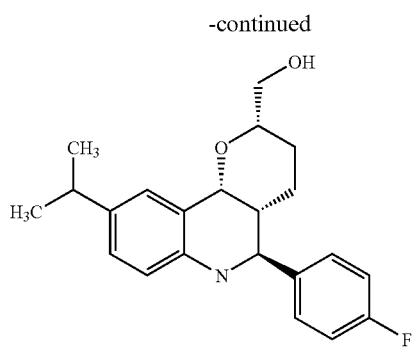
I494
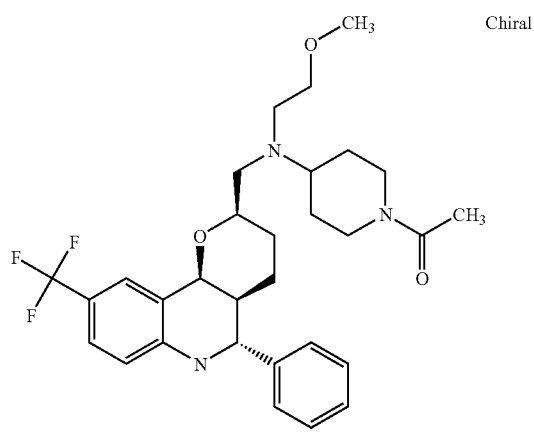
I495
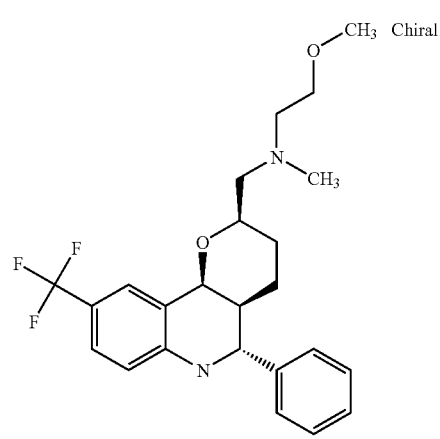
I496
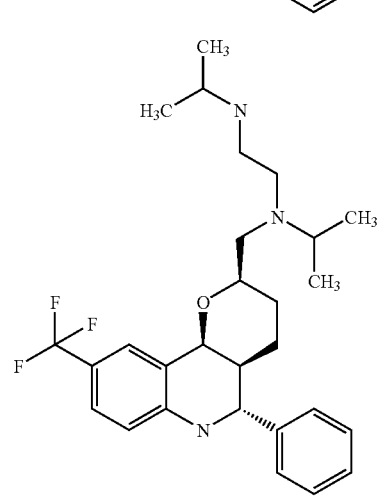
I497
-continued
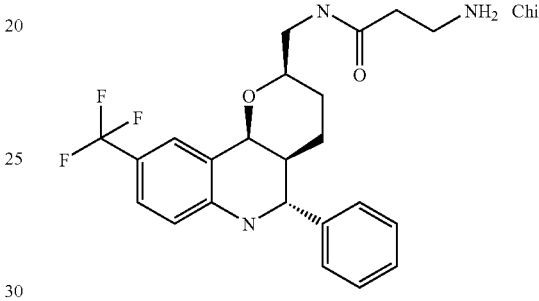
I498
I499
I500
I501

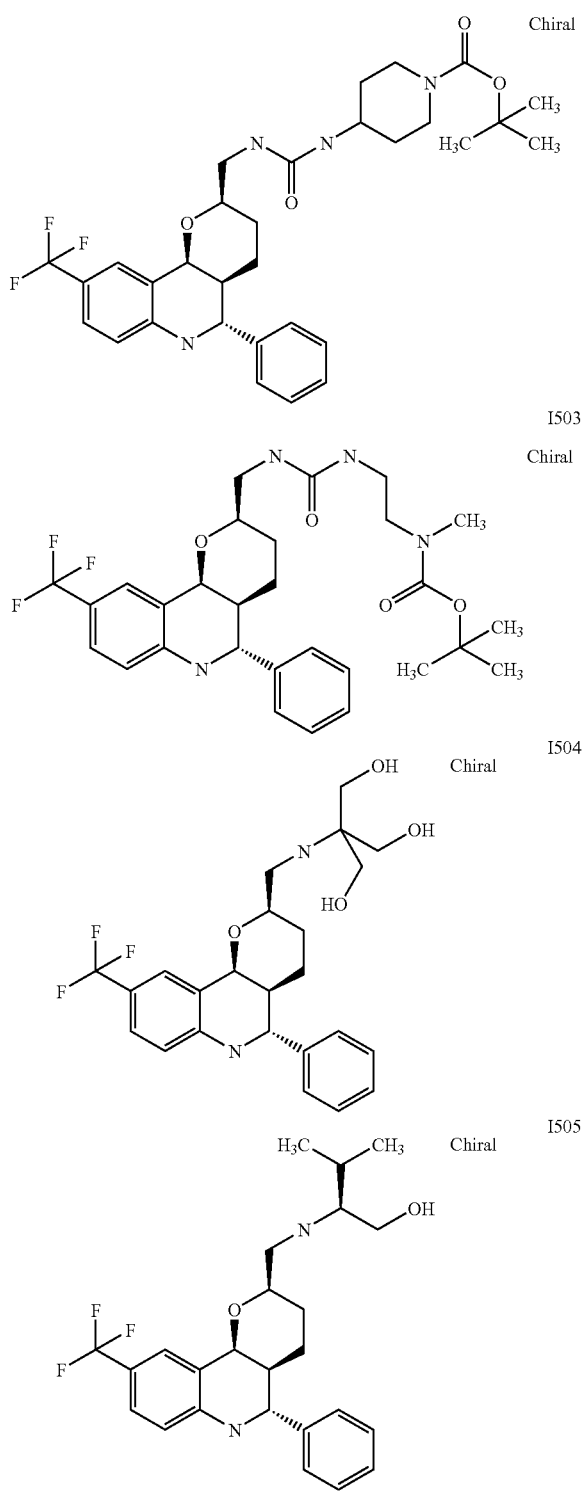

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials may also be formed in situ so that they are not isolated from the reaction mixture, but instead are immediately converted further into the compounds of the formula I.

The reaction is generally carried out in an inert solvent, preferably in the presence of a protonic acid or Lewis acid, such as TFA, HFIP, bismuth(III) salts, ytterbium(III) salts or CAN. Depending on the conditions used, the reaction time is between a few minutes and 14 days, the reaction temperature is between about 0° and 180°, normally between 0° and 100°, particularly preferably between 15° and 35° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; nitriles, such as acetonitrile; carbon disulfide; carboxylic acids, such as formic acid or acetic acid; nitro compounds, such as nitromethane or nitrobenzene, or mixtures of the said solvents.

Compounds of the formula I in which $R^7$ has a meaning other than H are preferably prepared by alkylation or acylation from the compounds of the formula I in which $R^7$ denotes H.

If desired, a functionally modified amino and/or hydroxyl group in a compound of the formula I can be liberated by solvolysis or hydrogenolysis by conventional methods. This can be carried out, for example, using NaOH or KOH in water, water/THF or water/dioxane at temperatures between 0 and 100°.

The reduction of an ester to the aldehyde or alcohol or the reduction of a nitrile to the aldehyde or amine is carried out by methods as are known to the person skilled in the art and are described in standard works of organic chemistry.

The said compounds according to the invention can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methyl-glutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The medicaments from Table 1 are preferably, but not exclusively, combined with the compounds of the formula I. A combination of the formula I and medicaments from Table 1 can also be combined with compounds of the formula V.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson |
| | Tetraplatin | Matthey) |
| | Ormiplatin | BBR-3464 (Hoffmann- |
| | Iproplatin | La Roche) |
| | | SM-11355 (Sumitomo) |
| | | AP-5280 (Access) |

TABLE 1-continued

| | | |
|---|---|---|
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilone B (Novartis) | AZ10992 (Asahi) |
| | T 900607 (Tularik) | !DN-5109 (Indena) |
| | T 138067 (Tularik) | AVLB (Prescient NeuroPharma) |
| | Cryptophycin 52 (Eli Lilly) | Azaepothilon B (BMS) |
| | Vinflunine (Fabre) | BNP-7787 (BioNumerik) |
| | Auristatin PE (Teikoku Hormone) | CA-4-Prodrug (OXiGENE) |
| | BMS 247550 (BMS) | Dolastatin-10 (NrH) |
| | BMS 184476 (BMS) | CA-4 (OXiGENE) |
| | BMS 188797 (BMS) | |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope | |

TABLE 1-continued

| | | |
|---|---|---|
| | Solutions) | O6-Benzylguanine |
| | Thymectacin (NewBiotics) | (Paligent) |
| | Edotreotid (Novartis) | |
| Farnesyl transferase inhibitors | Arglabin (NuOncology Labs) | Tipifarnib (Johnson & Johnson) |
| | lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | | BMS-275291 (Celltech) |
| Ribonucleoside reductase inhibitors | Marimastat (British Biotech) | Tezacitabine (Aventis) |
| | | Didox (Molecules for Health) |
| | Gallium maltolate (Titan) | |
| | Triapin (Vion) | |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immuno-modulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | |
| | | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | | !3-Alethin (Dovetail) |
| | Melanoma vaccine (CTL Immuno) | CLL-Thera (Vasogen) |
| | p21-RAS vaccine (GemVax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (EntreMed) |
| | Tamoxifen | |
| | Toremofin | Arzoxifen (Eli Lilly) |
| | Dexamethasone | |
| Photodynamic agents | Talaporfin (Light Sciences) | Pd-Bacteriopheophorbid (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide(Sugen/Pharmacia) | CEP-701 (Cephalon) |
| | ZD1839 (AstraZeneca) | CEP-751 (Cephalon) |
| | Erlotinib (Oncogene Science) | MLN518 (Millenium) |
| | | PKC412 (Novartis) |
| | Canertjnib (Pfizer) | Phenoxodiol O |
| | Squalamine (Genaera) | Trastuzumab (Genentech) |
| | SU5416 (Pharmacia) | C225 (ImClone) |
| | SU6668 (Pharmacia) | rhu-Mab (Genentech) |
| | ZD4190 (AstraZeneca) | MDX-H210 (Medarex) |
| | ZD6474 (AstraZeneca) | 2C4 (Genentech) |
| | Vatalanib (Novartis) | MDX-447 (Medarex) |
| | PKI166 (Novartis) | ABX-EGF (Abgenix) |
| | GW2016 | IMC-1C11 (ImClone) |

TABLE 1-continued

| | | |
|---|---|---|
| Various agents | (GlaxoSmithKline)<br>EKB-509 (Wyeth)<br>EKB-569 (Wyeth)<br>SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist, Merck KGaA)<br>SR-31747 (IL-1 antagonist, Sanofi-Synthelabo)<br>CCI-779 (mTOR kinase inhibitor, Wyeth)<br>Exisulind (PDE-V inhibitor, Cell Pathways)<br>CP-461 (PDE-V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>Bortezomib (proteasome inhibitor, Millennium)<br>SRL-172 (T-cell stimulant, SR Pharma)<br>TLK-286 (glutathione-S transferase inhibitor, Telik)<br>PT-100 (growth factor agonist, Point Therapeutics)<br>Midostaurin (PKC inhibitor, Novartis)<br>Bryostatin-1 (PKC stimulant, GPC Biotech)<br>CDA-II (apoptosis promoter, Everlife)<br>SDX-101 (apoptosis promoter, Salmedix)<br>Ceflatonin (apoptosis promoter, ChemGenex) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar)<br>Rituximab (CD20 antibody, Genentech)<br>Gemtuzumab (CD33 antibody, Wyeth Ayerst)<br>PG2 (haematopoiesis promoter, Pharmagenesis)<br>Immunol ™ (triclosan mouthwash, Endo)<br>Triacetyluridine (uridine prodrug, Wellstat)<br>SN-4071 (sarcoma agent, Signature BioScience)<br>TransMID-107 ™ (immunotoxin, KS Biomedix)<br>PCK-3145 (apoptosis promoter, Procyon)<br>Doranidazole (apoptosis promoter, Pola)<br>CHS-828 (cytotoxic agent, Leo)<br>Trans-retinic acid (differentiator, NIH)<br>MX6 (apoptosis promoter, MAXIA)<br>Apomine (apoptosis promoter, ILEX Oncology)<br>Urocidin (apoptosis promoter, Bioniche)<br>Ro-31-7453 (apoptosis promoter, La Roche)<br>Brostallicin (apoptosis promoter, Pharmacia) |

The compounds of the formula I are preferably combined with known anti-cancer agents:

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibition of VEGF in combination with radiotherapy have been described by specialists (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl-retinamide.

"Cytotoxic agents" refers to compounds which result in cell death primarily through direct action on the cellular function or inhibit or interfere with cell division, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)mu-[diamine-platinum(II)]bis[diamine(chloro)platinum(II)]tetrachloride, diarisidinyl-spermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplastone, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS 188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido [4,3-b]carbazole-1-carboxamide, asulacrine, (5a,5aB,8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]-acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]-quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo-(7.4.1.0.0)tetradeca-2, 4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal anti-bodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Particular preference is given to the use of the compound according to the invention for the treatment and prophylaxis of tumour diseases.

The tumour is preferably selected from the group of tumours of the squamous epithelium, bladder, stomach, kidneys, head and neck, oesophagus, cervix, thyroid, intestine, liver, brain, prostate, urogenital tract, lymphatic system, stomach, larynx and/or lung.

The tumour is furthermore preferably selected from the group lung adeno-carcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention also encompasses a method for the treatment of a patient who has a neoplasm, such as a cancer, by administration of a) one or more of the compounds of the formula I:

b) and one or more of the compounds of the formula V or acid-addition salts thereof, in particular hydrochlorides:

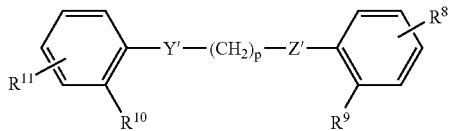

in which Y' and Z' each, independently of one another, denote O or N, $R^6$ and $R^7$ each, independently of one another, denote H, OH, halogen, $OC1$-10-alkyl, $OCF_3$, $NO_2$ or $NH_2$, n denotes an integer between 2 and 6, each inclusive, and $R^8$ and $R^9$ are each, independently of one another, preferably in the meta- or para-position and are selected from the group:

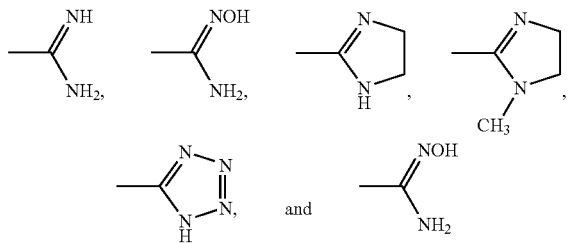

where the first and second compound are administered simultaneously or within 14 days of one another in amounts which are sufficient to inhibit the growth of the neoplasm.

The combination of the compounds of the formula I with the compounds of the formula V and other pentamidine analogues results in a synergistic action in the inhibition of neoplasias. Combinations comprising the compounds of the formula V are mentioned, for example, in WO 02058684.

The mechanism of action of pentamidine or derivatives thereof has not been clearly explained at present: pentamidine or derivatives thereof appears to have pleiotropic actions since it results in a decrease in DNA, RNA and protein synthesis. It was recently described that pentamidine is a capable inhibitor of PRL1, -2 and 3 phosphatases (Pathak et al., 2002) and tyrosine phosphatases, and overexpression thereof is accompanied by neoplastic malignant tumours in humans. On the other hand, it has been described that pentamidine is a medicament which binds to the DNA minor groove (Puckowska et al., 2004) and is able to exert its action via disturbance of gene expression and/or DNA synthesis.

The appended experiments show that:
both pentamidine and also the compounds of the formula I maintain cells in the G2/M cell cycle.
the combination of pentamidine and compounds of the formula I have additive to synergistic actions on cell proliferation.

Other suitable pentamidine analogues include stilbamidine (G-1) and hydroxystilbamidine (G-2) and indole analogues thereof (for example G-3):

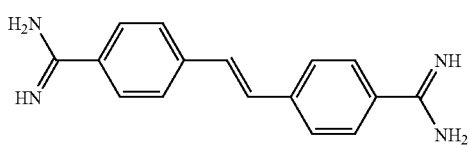

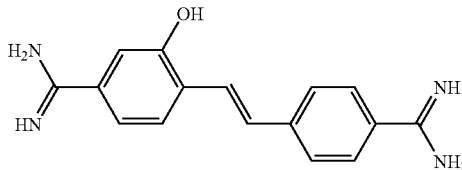

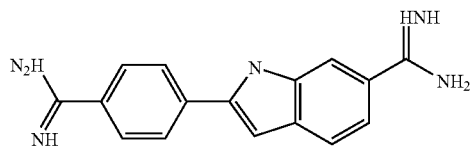

Each amidine unit may be replaced, independently of one another, by one of the units defined above for $R^8$ and $R^{11}$. As in the case of benzimidazoles and pentamidines, salts of stilbamidine, hydroxystilbamidine and indole derivatives thereof are also suitable for the process according to the invention. Preferred salts include, for example, dihydrochloride and methanesulfonate salts.

Still other analogues are those which fall under a formula which are provided in one of the U.S. Pat. Nos. 5,428,051, 5,521,189, 5,602,172, 5,643,935, 5,723,495, 5,843,980, 6,172,104 and 6,326,395 or the US patent application with the publication No. US 2002/0019437 Al, each of which is incorporated in its entirety by way of reference. Illustrative analogues include 1,5-bis(4'-(N-hydroxyamidino)phenoxy) pentane, 1,3-bis(4'-(N-hydroxyamidino)phenoxy)propane, 1,3-bis(2'-methoxy-4'-(N-hydroxyamidino)phenoxy)propane, 1,4-bis(4'-(N-hydroxyamidino)phenoxy)butane, 1,5-bis(4'-(N-hydroxyamidino)phenoxy)pentane, 1,4-bis(4'-(N-hydroxyamidino)phenoxy)butane, 1,3-bis(4'-(4-hydroxyamidino)phenoxy)propane, 1,3-bis(2'-methoxy-4'-(N-hydroxyamidino)phenoxy)propane, 2,5-bis[4-amidinophenyl]furan, 2,5-bis[4-amidinophenyl]furan bisamide oxime, 2,5-bis[4-amidinophenyl]furan bis-O-methylamide oxime, 2,5-bis[4-amidinophenyl]furan bis-O-ethylamide oxime, 2,8-diamidinodibenzothiophene, 2,8-bis (N-isopropylamidino)carbazole, 2,8-bis(N-hydroxyamidino)carbazole, 2,8-bis(2-imidazolinyl)dibenzothiophene, 2,8-bis(2-imidazolinyl)-5,5-dioxodibenzothiophene, 3,7-diamidinodibenzothiophene, 3,7-bis(N-isopropylamidino)dibenzothiophene, 3,7-bis(N-hydroxyamidino)dibenzothiophene, 3,7-diaminodibenzothiophene, 3,7-dibromodibenzothiophene, 3,7-dicyanodibenzothiophene, 2,8-diamidinodibenzofuran, 2,8-di-(2-imidazolinyl)dibenzofuran, 2,8-di-(N-isopropylamidino)dibenzofuran, 2,8-di-(N-hydroxylamidino)dibenzofuran, 3,7-di-(2-imidazolinyl)dibenzofuran, 3,7-di-(isopropylamidino)dibenzofuran, 3,7-di-(A-hydroxylamidino)dibenzofuran, 2,8-dicyanodibenzofuran, 4,4'-dibromo-2,2'-dinitrobiphenyl, 2-methoxy-2'-nitro-4,4'-dibromobiphenyl, 2-methoxy-2'-amino-4,4'-dibromobiphenyl, 3,7-dibromodibenzofuran, 3,7-dicyanodibenzofuran, 2,5-bis(5-amidino-2-benzimidazolyl)pyrrole, 2,5-bis[5-(2-imidazolinyl)-2-benzimidazolyl]pyrrole, 2,6-bis[5-(2-imidazolinyl)-2-benzimidazolyl]pyridine, 1-methyl-2,5-bis(5-amidino-2-benzimidazolyl)pyrrole, 1-methyl-2,5-bis[5-(2-imidazolyl)-2-benzimidazolyl]pyrrole, 1-methyl-2,5-bis[5-(1,4,5,6-tetrahydro-2-pyrimidinyl)-2-benzimidazolyl]pyrrole, 2,6-bis (5-amidino-2-benzimidazoyl)pyridine, 2,6-bis[5-(1,4,5,6-tetrahydro-2-pyrimidinyl)-2-benzimidazolyl]pyridine, 2,5- bis-(5-amidino-2-benzimidazolyl)furan, 2,5-bis[5-(2-imidazolinyl)-2-benzimidazolyl]furan, 2,5-bis(5-N-isopropylamidino-2-benzimidazolyl)furan, 2,5-bis(4-guanylphenyl)furan, 2,5-bis(4-guanylphenyl)-3,4-dimethylfuran, 2,5-di-p-[2-(3,4,5,6-tetrahydropyrimidyl)phenyl]furan, 2,5-bis[4-(2-imidazolinyl)phenyl]-furan, 2,5-[bis{4-(2-tetrahydropyrimidinyl)}phenyl]p-(tolyloxy)furan, 2,5-[bis{4-(2-imidazolinyl)}phenyl]-3-p-(tolyloxy)furan, 2,5-bis{4-[5-(N-2-aminoethylamido)benzimidazol-2-yl]phenyl}furan, 2,5-bis[4-(3a,4,5,6,7,7a-hexahydro-1H-benzimidazol-2-yl)phenyl]furan, 2,5-bis[4-(4,5,6,7-tetrahydro-1H-1,3-diazepin-2-yl)phenyl]furan, 2,5-bis(4-N,N-dimethylcarboxhydrazidophenyl)furan, 2,5-bis{4-[2-(N-2-hydroxyethyl)imidazolinyl]phenyl}furan, 2,5-bis[4-(N-isopropylamidino)phenyl]furan, 2,5-bis{4-[3-(dimethylaminopropyl)amidino]phenyl}furan, 2,5-bis{4-[N-(3-aminopropyl)amidino]phenyl}-furan, 2,5-bis[2-(imidzaolinyl)phenyl]-3,4-bis(methoxymethyl)furan, 2,5-bis-[4-N-(dimethylaminoethyl)guanyl]phenylfuran, 2,5-bis{4-[(N-2-hydroxyethyl)guanyl]phenyl}furan, 2,5-bis[4-N-(cyclopropylguanyl)phenyl]furan, 2,5-bis[4-(N,N-diethylaminopropyl)guanyl]phenylfuran, 2,5-bis{4-[2-(N-ethylimidazolinyl)]phenyl}furan, 2,5-bis{4-[N-(3-pentylguanyl)]}phenylfuran, 2,5-bis[4-(2-imidazolinyl)phenyl]-3-methoxyfuran, 2,5-bis[4-(N-isopropylamidino)phenyl]-3-methylfuran, bis[5-amidino-2-benzimidazolyl]methane, bis[5-(2-imidazolyl)-2-benzimidazolyl]methane, 1,2-bis[5-amidino-2-benzimidazolyl]ethane, 1,2-bis[5-(2-imidazolyl)-2-benzimidazolyl]ethane, 1,3-bis[5-amidino-2-benzimidazolyl]propane, 1,3-bis[5-(2-imidazolyl)-2-benzimidazolyl]propane, 1,4-bis[5-amidino-2-benzimidazolyl]propane, 1,4-bis[5-(2-imidazolyl)-2-benzimidazolyl]butane, 1,8-bis[5-amidino-2-benzimidazolyl]octane, trans-1,2-bis[5-amidino-2-benzimidazolyl]ethene, 1,4-bis[5-(2-imidazolyl)-2-benzimidazolyl]-1-butene, 1,4-bis[5-(2-imidazolyl)-2-benzimidazolyl]-2-butene, 1,4-bis[5-(2-imidazolyl)-2-benzimidazolyl]-1-methylbutane, 1,4-bis[5-(2-imidazolyl)-2-benzimidazolyl]-2-ethylbutane, 1,4-bis[5-(2-imidazolyl)-2-benzimidazolyl]-1-methyl-1-butene, 1,4-bis[5-(2-imidazolyl)-2-benzimidazolyl]-2,3-diethyl-2-butene, 1,4-bis[5-(2-imidazolyl)-2-benzimidazolyl]-1,3-butadiene, 1,4-bis[5-(2-imidazolyl)-2-benzimidazolyl]-2-methyl-1,3-butadiene, bis[5-(2-pyrimidyl)-2-benzimidazolyl]methane, 1,2-bis[5-(2-pyrimidyl)-2-benzimidazolyl]ethane, 1,3-bis[5-amidino-2-benzimidazolyl]propane, 1,3-bis[5-(2-pyrimidyl)-2-benzimidazolyl]propane, 1,4-bis[5-(2-pyrimidyl)-2-benzimidazolyl]butane, 1,4-bis[5-(2-pyrimidyl)-2-benzimidazolyl]-1-butene, 1,4-bis[5-(2-pyrimidyl)-2-benzimidazolyl]-2-butene, 1,4-bis[5-(2-pyrimidyl)-2-benzimidazolyl]-1-methyl-butane, 1,4-bis[5-(2-pyrimidyl)-2-benzimidazolyl]-2-ethylbutane, 1,4-bis[5-(2-pyrimidyl)-2-benzimidazolyl]-1-methyl-1-butene, 1,4-bis[5-(2-pyrimidyl)-2-benzimidazolyl]-2,3-diethyl-2-butene, 1,4-bis[5-(2-pyrimidyl)-2-benzimidazolyl]-1,3-butadiene and 1,4-bis[5-(2-pyrimidyl)-2-benzimidazolyl]-2-methyl-1,3-butadiene, 2,4-bis(4-guanylphenyl)pyrimidine, 2,4-bis(4-imidazolin-2-yl)pyrimidine, 2,4-bis[(tetrahydropyrimidinyl-2-yl)phenyl]pyrimidine, 2-(4-[N-i-propylguanyl]phenyl)-4-(2-methoxy-4-[N-i-propylguanyl]phenyl)pyrimidine, 4-(N-cyclopentylamidino)-1,2-phenylenediamine, 2,5-bis[2-(5-amidino)benzimidazoyl]furan, 2,5-bis[2-{5-(2-imidazolino)}benzimidazoyl]-furan, 2,5-bis[2-(5-N-isopropylamidino)benzimidazoyl]furan, 2,5-bis[2-(5-N-cyclopentylamidino)benzimidazoyl]furan, 2,5-bis[2-(5-amidino)benzimidazoyl]pyrrole, 2,5-bis[2-{5-(2-imidazolino)}benzimidazoyl]pyrrole, 2,5-bis[2-(5-N-isopropylamidino)benzimidazoyl]pyrrole, 2,5-bis[2-(5-N-cyclopentylamidino)benzimidazoyl]pyrrole, 1-methyl-2,5-bis[2-(5-amidino)benzimidazoyl]pyrrole, 2,5-bis[2-{5-(2-imidazolino)}benzimidazoyl]-1-methylpyrrole, 2,5-bis[2-(5-N-cyclopentylamidino)benzimidazoyl]-1-methylpyrrole, 2,5-bis-[2-(5-N-isopropylamidino)benzimidazoyl]thiophene, 2,6-bis[2-{5-(2-imidazolino)}benzimidazoyl]pyridine, 2,6-bis[2-(5-amidino)benzimidazoyl]-pyridine, 4,4'-bis[2-(5-N-isopropylamidino)benzimidazoyl]-1,2-diphenylethane, 4,4'-bis[2-(5-N-cyclopentylamidino)benzimidazoyl]-2,5-diphenylfuran, 2,5-bis[2-(5-amidino)benzimidazoyl]benzo[b]furan, 2,5-bis[2-(5-N-cyclopentylamidino)benzimidazoyl]benzo[b]furan, 2,7-bis[2-(5-N-isopropylamidino)benzimidazoyl]fluorine, 2,5-bis[4-(3-(N-morpholinopropyl)carbamoyl)phenyl]furan, 2,5-bis[4-(2-N,N-dimethylaminoethylcarbamoyl)phenyl]furan, 2,5-bis[4-(3-N,N-dimethylaminopropylcarbamoyl)phenyl]-furan, 2,5-bis[4-(3-N-methyl-3-N-phenylaminopropylcarbamoyl)phenyl]-furan, 2,5-bis[4-(3-N,N8,N11-trimethylaminopropylcarbamoyl)phenyl]furan, 2,5-bis[3-amidinophenyl]furan, 2,5-bis[3-(N-isopropylamidino)amidinophenyl]furan, 2,5-bis[3-[(N-(2-dimethylaminoethyl)amidino]phenylfuran, 2,5-bis[4-(N-2,2,2-trichloroethoxycarbonyl)amidinophenyl]furan, 2,5-bis[4-(N-thioethylcarbonyl)amidinophenyl]furan, 2,5-bis[4-(N-benzyloxycarbonyl)amidinophenyl]furan, 2,5-bis[4-(N-phenoxycarbonyl)amidinophenyl]furan, 2,5-bis[4-(N-(4-fluoro)phenoxycarbonyl)amidinophenyl]furan, 2,5-bis[4-(N-(4-methoxy)phenoxycarbonyl)amidinophenyl]furan, 2,5-bis[4-(1-acetoxyethoxycarbonyl)amidinophenyl]furan and 2,5-bis[4-(N-(3-fluoro)phenoxycarbonyl)amidinophenyl]furan. Processes for the preparation of one of the above compounds are described in U.S. Pat. Nos. 5,428,051, 5,521,189, 5,602,172, 5,643,935, 5,723,495, 5,843,980, 6,172,104 and 6,326,395 or the US patent application with the publication no. US 2002/0019437 A1.

Pentamidine metabolites are likewise suitable in the antiproliferative combination according to the invention. Pentamidine is rapidly metabolised in the body to at least seven primary metabolites. Some of these metabolites have one or more actions in common with pentamidine. Pentamidine metabolites have an antiproliferative action when combined with a benzimidazole or an analogue thereof.

Seven pentamidine analogues are shown below.

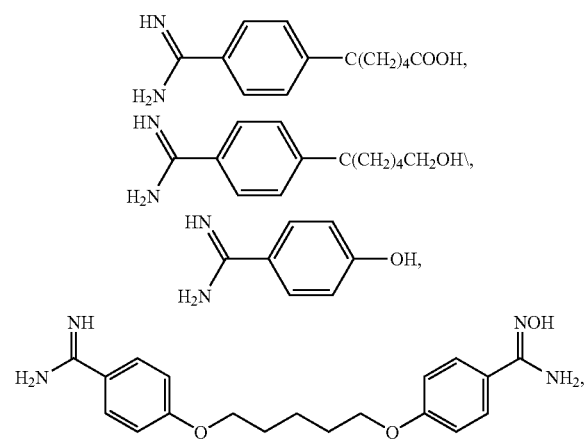

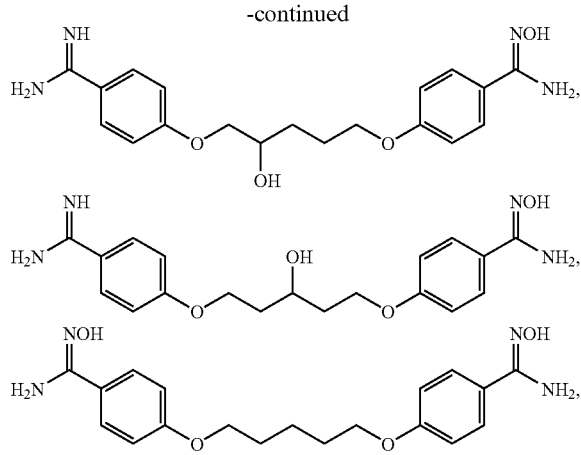

The combinations according to the invention of compounds of the formula I and formula V or analogues thereof and metabolites thereof are suitable for the treatment of neoplasms. Combination therapy can be carried out alone or in combination with another therapy (for example operation, irradiation, chemotherapy, biological therapy). In addition, a person whose risk of developing a neoplasm is greater (for example someone who is genetically predisposed or someone who previously had a neoplasm) can be given prophylactic treatment in order to inhibit or delay neoplasm formation.

The invention likewise relates to the combination of kinesin ATPase Eg5/KSP with the compounds of the formula V, pentamidine, analogues thereof and/or metabolites thereof.

The dosage and frequency of administration of each compound in the combination can be controlled independently. For example, one compound may be administered orally three times daily, while the second compound may be administered intramuscularly once per day. The compounds may also be formulated together, leading to administration of both compounds.

The antiproliferative combinations according to the invention can also be provided as components of a pharmaceutical package. The two medicaments can be formulated together or separately and in individual dosage amounts.

Under another aspect, the invention encompasses a method for the treatment of a patient who has a neoplasm, such as a cancer, by administration of a compound of the formula (I) and (V) in combination with an antiproliferative agent. Suitable antiproliferative agents encompass those provided in Table 1.

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS):
EI (electron impact ionisation) M+
FAB (fast atom bombardment) (M+H)+
ESI (electrospray ionisation) (M+H)+
APC-MS (atmospheric pressure chemical ionisation-mass spectrometry) (M+H)+

EXAMPLE 1

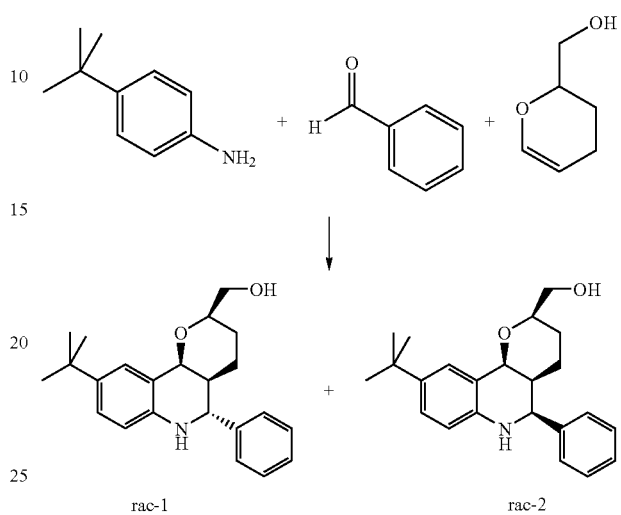

a. Reaction in the Presence of Trifluoroacetic Acid (TFA)

The solution of the TFA salt of 4-tert-butylaniline in acetonitrile (4-tert-butylaniline (0.50 g, 3.35 mmol) was taken up in acetonitrile (4 ml), cooled to 0° C. and TFA (0.38 g, 3.35 mmol) was slowly added with stirring) was added rapidly to a solution, cooled to 0° C., of an equimolar amount of benzaldehyde and an equimolar amount of the substituted 3,4-dihydro-2H-pyran in acetonitrile (2 ml), and the mixture was stirred at this temperature for a further 60 min. The reaction solution was evaporated to dryness and separated by column chromatography, giving a colourless solid, which proved to be the isomer mixture of the respective racemic trans/cis compound.

In order to separate the cis/trans isomers, the solid was taken up in 0.1 N HCl in isopropanol (20 ml), 100 ml of both diethyl ether and cyclohexane were added, and the product was crystallised overnight at 4° C. The colourless solid was filtered off, washed with a little diethyl ether and dried, giving the colourless compound rac-1 hydrochloride. The mother liquor was evaporated to dryness in a rotary evaporator, and the cis isomer was purified by column chromatography and converted into the hydrochloride, giving rac-2.

Relatively small amounts of rac-1 and rac-2 were separated into the corresponding enantiomers by chiral HPLC (2× Chiralpak AD 20 μm, eluent: methanol) and reconverted into the hydrochlorides.

The individual compounds can subsequently be processed further by known methods.

For example, they can be esterified using a carboxylic acid. It is likewise possible to convert the free hydroxyl group into a leaving group using methanesulfonyl chloride and into the corresponding amines or nitrites by reaction with nucleophiles, such as, for example, NH₃ or NaCN.

All further compounds of the formula I can be obtained analogously using the corresponding precursors. The following examples relate to pharmaceutical compositions.

EXAMPLE 2

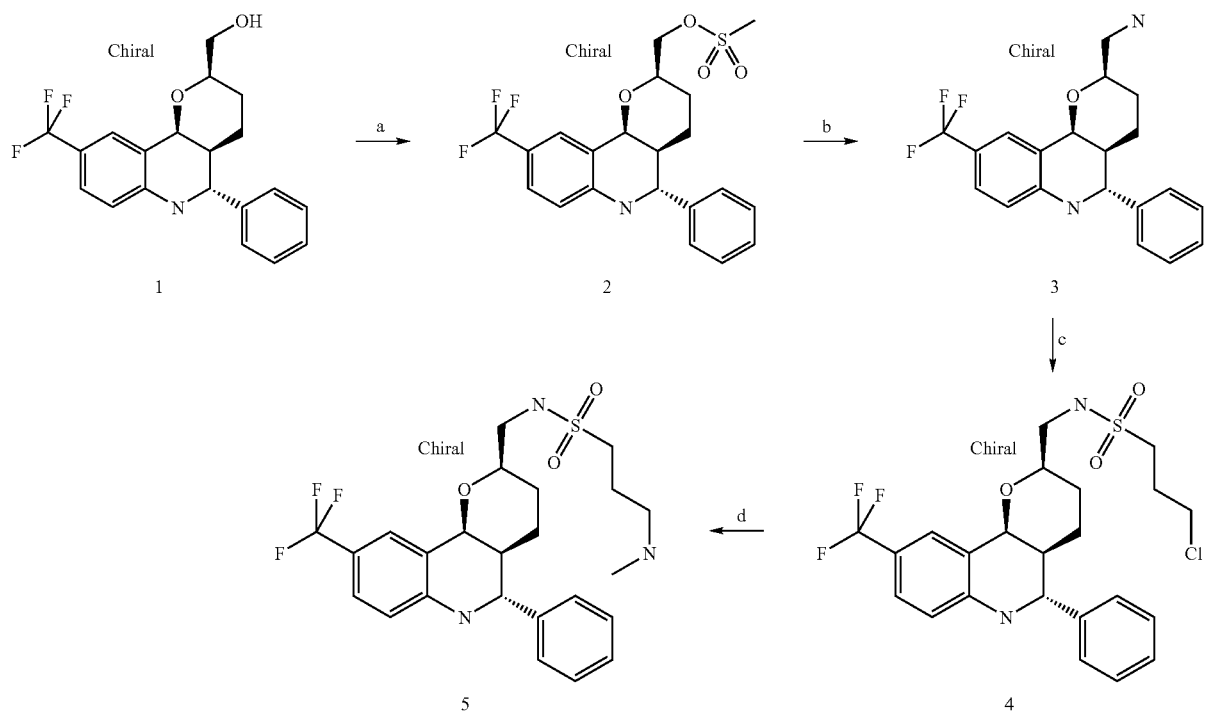

a.

The alcohol 1 (1.00 g, 2.75 mmol) were suspended in 10 ml of DCM, triethylamine (0.76 ml, 5.48 mmol) was added at RT, and methanesulfonyl chloride (0.22 ml, 2.84 mmol) was subsequently added dropwise, likewise at RT. The solution was stirred further overnight, the solvent was removed, the crude substance was taken up in ethyl acetate (50 ml) and extracted 2× with water. The organic phase was dried, filtered, and the solvent was removed, giving 1.15 g (2.61 mmol, 95%) of yellowish crystals of high purity which was characterised as comp. 2.

b.

Compound 2 (1.00 g, 2.27 mmol) was dissolved in a saturated solution of ammonia in MeOH (about 5.9 m, 20 ml) and stirred in a pressure flask at 100° C. for 18 h.

The excess ammonia was evaporated off, the solvent was removed, and the residue was processed further without further purification, giving 0.81 g (2.22 mmol, 98%) of yellowish crystals of compound 3.

c.

The amine 3 (0.75 g, 2.07 mmol) were dissolved in 15 ml of DCM, triethylamine (0.57 ml, 4.14 mmol) was added at RT, and 3-chloropropanesulfonyl chloride (0.37 ml, 2.07 mmol) was subsequently added dropwise, likewise at RT. The solution was stirred further overnight, the solvent was removed, the crude substance was taken up in ethyl acetate (50 ml) and extracted 2× with water. The organic phase was dried, filtered, and the solvent was removed, giving 0.85 g (1.67 mmol, 82%) of yellowish crystals, which was characterised as comp. 4.

d.

Compound 4 (0.5 g, 0.99 mmol) was dissolved in 10 ml of an 8 M solution of methylamine in methanol and stirred in a pressure flask at 100° C. for 18 h. The product was subsequently precipitated by addition of water, filtered off and purified by column chromatography (methanol/ethyl acetate/cyclohexane, gradient), giving 373 mg (0.75 mmol, 75%) of a colourless solid, which was converted into the hydrochloride in the usual manner.

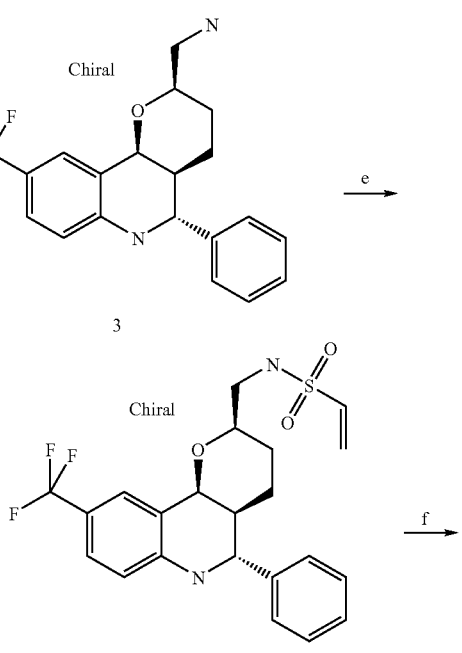

-continued

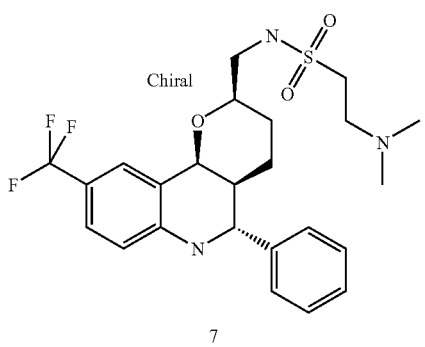

7 e.

The amine 3 (250 mg, 0.69 mmol) were dissolved in 4 ml of DCM, triethylamine (0.19 ml, 1.38 mmol) was added at RT, and 2-chloropropanesulfonyl chloride (0.37 ml, 2.07 mmol) was subsequently added dropwise, likewise at RT. The solution was stirred further overnight, the solvent was removed, the crude substance was taken up in ethyl acetate (50 ml) and extracted 2× with water. The organic phase was dried, filtered, and the solvent was removed, giving 312 mg (0.69 mmol, 100%) of yellowish crystals, which was characterised as comp. 6.

f.

The sulfonamide 6 (70 mg, 0.16 mmol) was dissolved in a 2 M solution of dimethylamine in THF (1.00 ml) and stirred overnight at RT. The solvent was removed, and the residue was purified by preparative reversed-phase HPLC (acetonitrile/water gradient with 0.1% of TFA), giving 49 mg (0.08 mmol, 52%) of a colourless solid.

EXAMPLE A

Assay I

The efficacy of the compounds according to the invention can be determined, for example, via the Eg5 ATPase activity, which is measured via an enzymatic regeneration of the product ADP to ATP by means of pyruvate kinase (PK) and subsequent coupling to an NADH-dependent lactate dehydrogenase (LDH) reaction. The reaction can be monitored via the change in absorbance at 340 nm by coupling to the NADH-dependent LDH. The regeneration of the ATP simultaneously ensures that the substrate concentration remains constant. The change in absorbance per time unit are analysed graphically and a linear regression carried out in the visually linear region of the reaction.

EXAMPLE B

Assay II

The combination of the antiprotozoic pentamidine and the inhibitors of kinesin ATPase Eg5/KSP results in increased inhibitory effects in cell proliferation tests with the colon carcinoma cell line HCT116.

Eg5 inhibitors adversely affect the ATPase activity and inhibit the course of the cell cycle owing to an error in the separation of the spindle poles.

The determination of the efficacy of the compounds of the formula I according to the invention in combination with compounds of the formula V and/or medicaments from Table I can be demonstrated as follows in combination assays:

$10^3$ to $10^4$ cells of a defined cell line (HCT116, Colo 205, MDA-MB 231, etc.) are sown into each well of a 96-well microtitre plate and cultivated overnight under standard conditions. For the substances of the combination to be tested, 10-50 mM stock solutions in DMSO were prepared. Dilution series (generally 3-fold dilution steps) of the individual substances were combined with one another in the form of a pipetting scheme (see scheme below), while maintaining a DMSO final concentration of 0.5% (v/v). Next morning, the substance mixtures were added to the cells, which were incubated under culture conditions for a further 48 hours. At the end of the cultivation, Crystal Violet staining of the cells was carried out. After extraction of the Crystal Violet from the fixed cells, the absorption at 550 nm was measured spectrophotometrically. It can be used as a quantitative measure of the adherent cells present.

Scheme

Compounds of the formula I →

| | 1 | 2 | 3 | 4 | 5 | 6 | 7 | 8 | 9 | 10 | 11 | 12 |
|---|---|---|---|---|---|---|---|---|---|---|---|---|
| A | | 81y | 27y | 9y | 3y | y | 0 | | | | | |
| B | 81x | | | | | | | | empty | empty | empty | |
| C | 27x | | | | | | | | 0.5% DMSO | 0.5% DMSO | 0.5% DMSO | |
| D | 9x | | | | | | | | | | | |
| E | 3x | | | | | | | | | | | |
| F | x | | | | | | | | | | | |
| G | 0 | | | | | | | | | | | |
| H | | | | | | | | | | | | |

Compounds of the formula V

The following examples relate to medicaments:

EXAMPLE C

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE D

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE E

Solution

A solution is prepared from 1 g of an active ingredient of the formula I, 9.38 g of $NaH_2PO_4·2H_2O$, 28.48 g of $Na_2HPO_4·12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE F

Ointment 500 mg of an active ingredient of the formula I are mixed with 99.5 g of Vaseline under aseptic conditions.

EXAMPLE G

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE H

Dragees

Tablets are pressed analogously to Example E and subsequently coated in a conventional manner with a coating of sucrose, potato starch, talc, tragacanth and dye.

EXAMPLE I

Capsules 2 kg of active ingredient of the formula I are introduced into hard gelatine capsules in a conventional manner in such a way that each capsule contains 20 mg of the active ingredient.

EXAMPLE J

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound or compounds of the formula I:

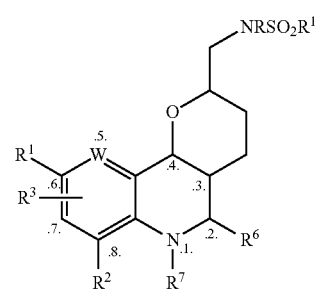

in which
W denotes CH or N,
$R^1$, $R^2$, $R^3$, independently of one another, denote H, A, aryl, heteroaryl, Hal, —$(CY_2)_n$—SA, —$(CY_2)_n$—$SCF_3$, —$(CY_2)_n$—SCN, —$(CY_2)_n$—$CF_3$, —$(CY_2)_n$—$OCF_3$, R, NR—$NR_2$, $X(CY_2)_n XR$, $X(CY_2)_n Y$, $(CY_2)_n$-cycloalkyl, $(CY_2)_n CH=CH_2$, cycloalkyl, —$SCH_3$, —SCN, —$CF_3$, —$OCF_3$, —OA, —$(CY_2)_n$—OH, —$(CY_2)_n$—$CO_2R$, —$(CY_2)_n$—CN, —$(CY_2)_n$-Hal, —$(CY_2)_n$—Y, —$(CY_2)_n$—$NR_2$, $(CY_2)_n$—OA, $(CY_2)_n$—OCOA, —$SCF_3$, $(CY_2)_n$—$CONR_2$, —$(CY_2)_n$—NHCOA, —$(CY_2)_n$—$NHSO_2A$, $SF_5$, $Si(CH_3)_3$, CO—$(CY_2)_n$—$CH_3$, —$(CY_2)_n$—N-pyrolidone, $(CH_2)_n NR$-COOR, NRCOOR, NCO, $(CH_2)_n COOR$, NCOOR, $(CH_2)_n OH$, $NR(CH_2)_n NR_2$, $C(OH)R_2$, $NR(CH_2)_n OR$, NCOR, $(CH_2)_n$-aryl, $(CH_2)_n$-heteroaryl, $(CH_2)_n R^1$, $(CH_2)_n X(CH_2)_n$-aryl, $(CH_2)_n X(CH_2)_n$-heteroaryl, $(CH_2)_n CONR_2$, $XCONR(CH_2)_n NR_2$, $N[(CH_2)_n X$-COOR]CO$(CH_2)_n$-aryl, $N[(CH_2)_n XR]CO(CH_2)_n$-aryl, $N[(CH_2)_n XR]CO(CH_2)_n$-X-aryl, $N[(CH_2)_n XR]SO_2(CH_2)_n$-aryl, $N[(CH_2)_n NRCOOR]CO(CH_2)_n$-aryl, $N[(CH_2)_n NR_2]CO(CH_2)_n$-aryl, $N[(CH_2)_n NR_2]CO(CH_2)_n NR$-aryl, $N[(CH_2)_n NR_2]SO_2(CH_2)_n$-aryl, $N[(CH_2)_n XR]CO(CH_2)_n$-heteroaryl, $N[(CH_2)_n XR]CO(CH_2)_n$-X-heteroaryl, CO-aryl, $SO_2$-aryl, $N[(CH_2)_n XR]SO_2(CH_2)_n$-heteroaryl, $N[(CH_2)_n NRCOOR]CO(CH_2)_n$-heteroaryl, $N[(CH_2)_n NR_2]CO(CH_2)_n$-heteroaryl, $N[(CH_2)_n NR_2]CO(CH_2)_n NR$-heteroaryl, $R^1$ and $R^3$ together also denote —N—$C(CF_3)$=N—, —N—CR=N—, —N—N=N— and where non-adjacent $CY_2$ groups may also be replaced by X
Y denotes H, A, Hal, OR, E-$R^1$,
E denotes —$NR^1SO_2$—, —$SO_2NR^1$—, —$CONR^1$—, —$NR^1CO$—, —COO—, OOC—, CO, —$SO_2$—, —X—, $NR^1CONR^1$—, —$OCONR^1$—, —$NR^1COO$—, —CSNR¹—, —NR¹CS—, —NR¹CSNR¹—, —SCONR¹—, —NR¹COS—, —OCSNR¹—, NR¹CSO—, SCSNR¹—, —NR¹CSS or a single bond A denotes alkyl or cycloalkyl, in which one or more H atoms may be replaced by Hal, Hal denotes F, Cl, Br or I R denotes H or A, in the case of geminal radicals R together also —(CH₂)₅—, —(CH₂)₄— or —(CH₂)ₙ—X—(CH₂)ₙ, X denotes O, S or NR¹, R⁶ denotes phenyl, 2-, 3- or 4-pyridyl, pyrimidyl, furyl or thienyl, each of which is unsubstituted or mono- or polysubstituted by Hal, CN, NO₂, OH, CF₃, OCH(CF₃)₂, OCOCH₃ or A, R⁷ denotes (C═O)—R, (C═O)—NR₂, (C═O)—OR, H or A and n denotes 0, 1, 2, 3, 4, 5, 6 or 7 and tautomers, salts and stereoisomers thereof, including mixtures thereof in all ratios.

2. A compound or compounds according to claim 1 in which R² denotes H.

3. A compound or compounds according to claim 1 in which R³ denotes H.

4. A compound or compounds according to claim 1 in which R⁷ denotes H.

5. A compound or compounds of the sub-formulae I1 to I59:

I1

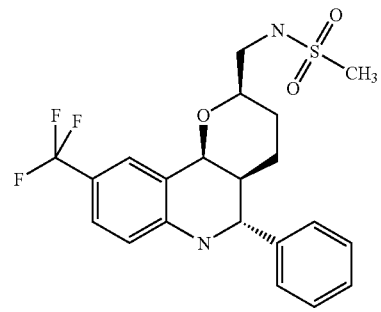

I2

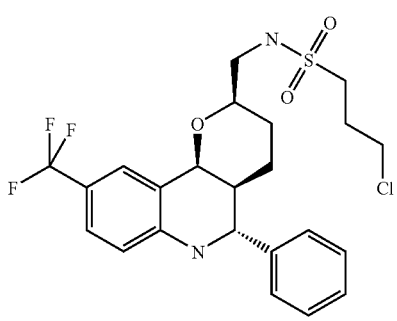

-continued

I3

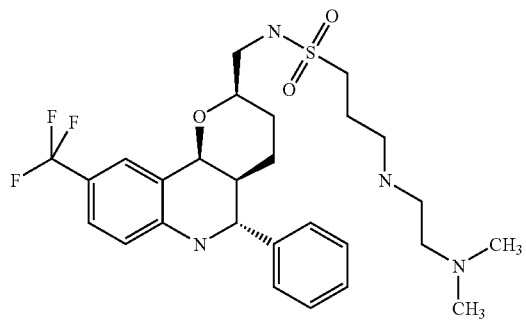

I4

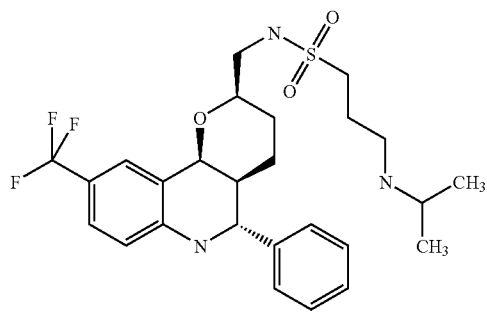

I5

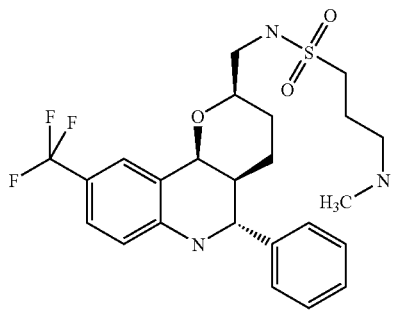

I6

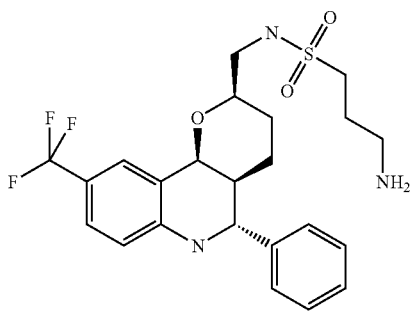

I7

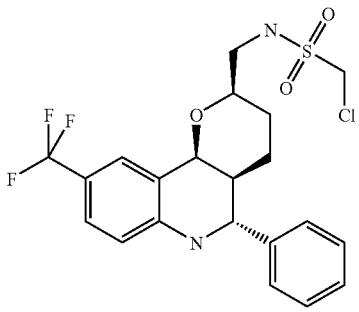

-continued
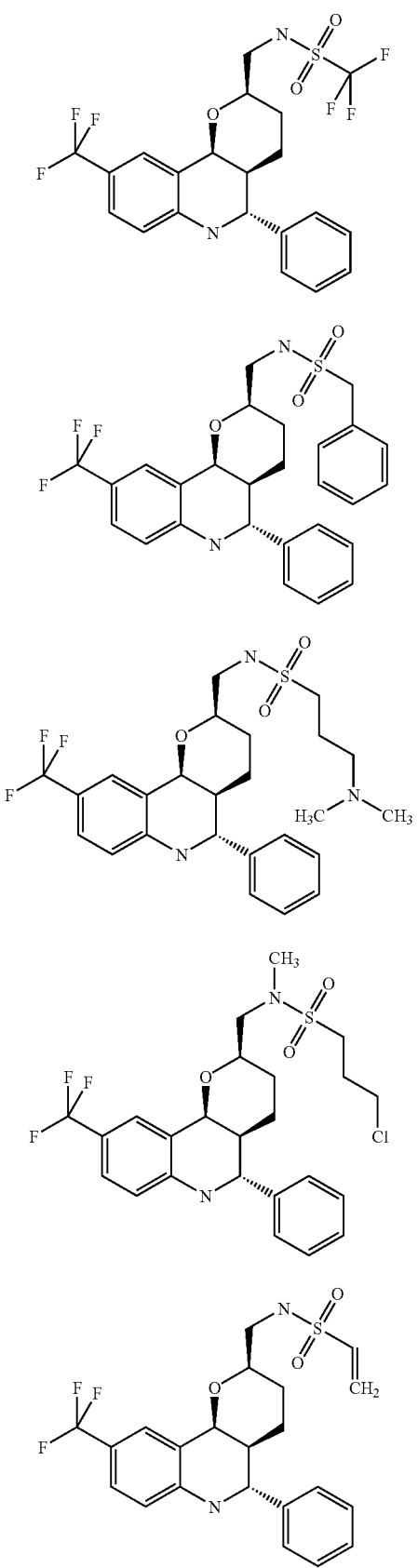
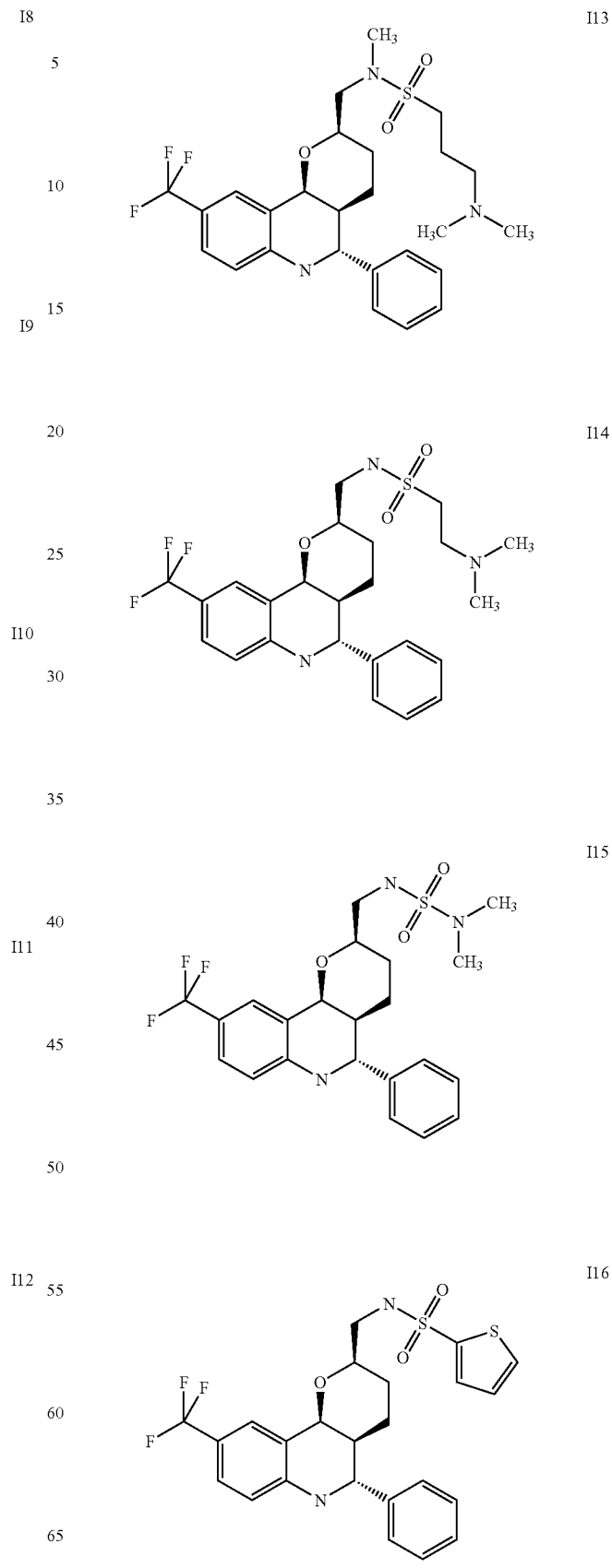

-continued
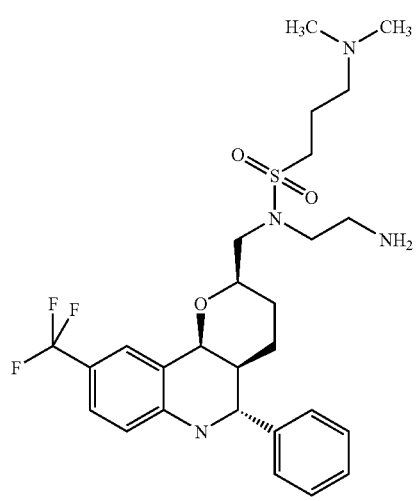
I17
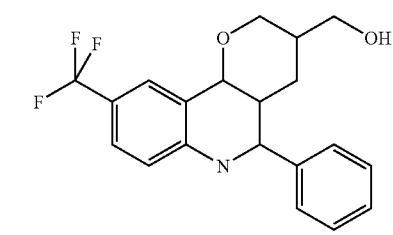
I18
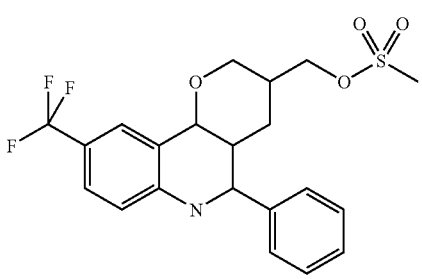
I19
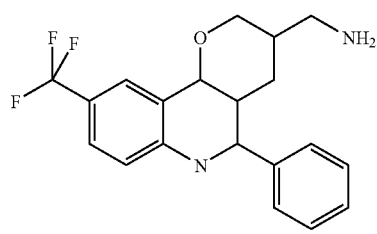
I20
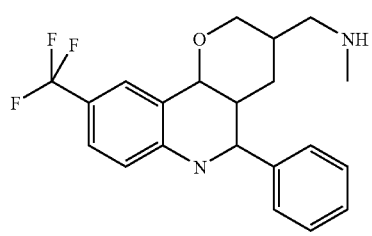
I21
-continued
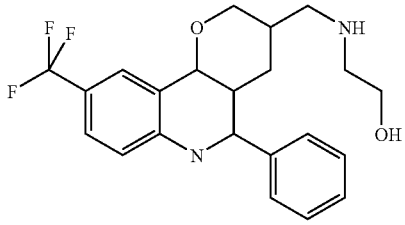
I22
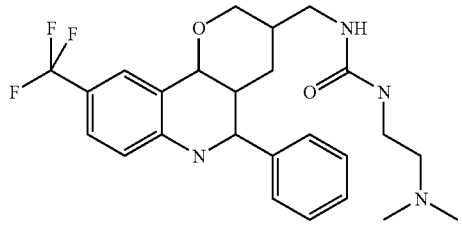
I23
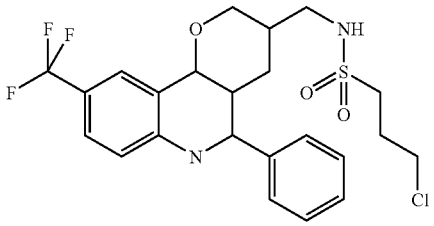
I24
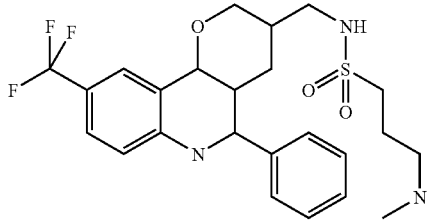
I25
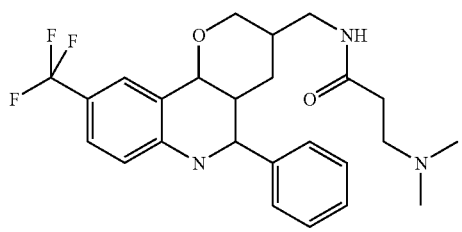
I26
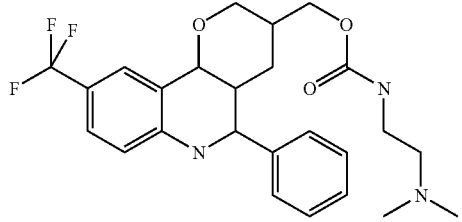
I27

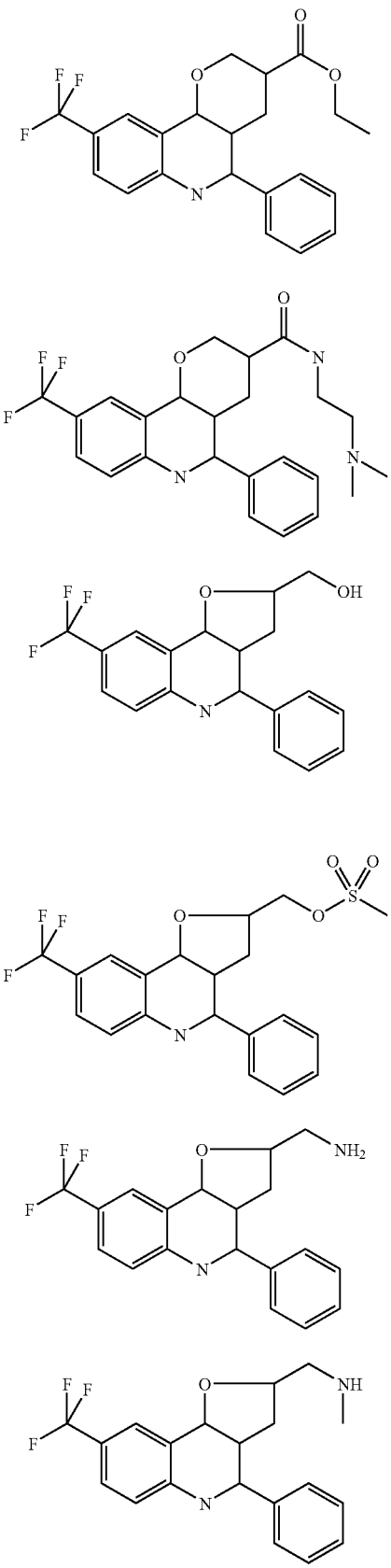
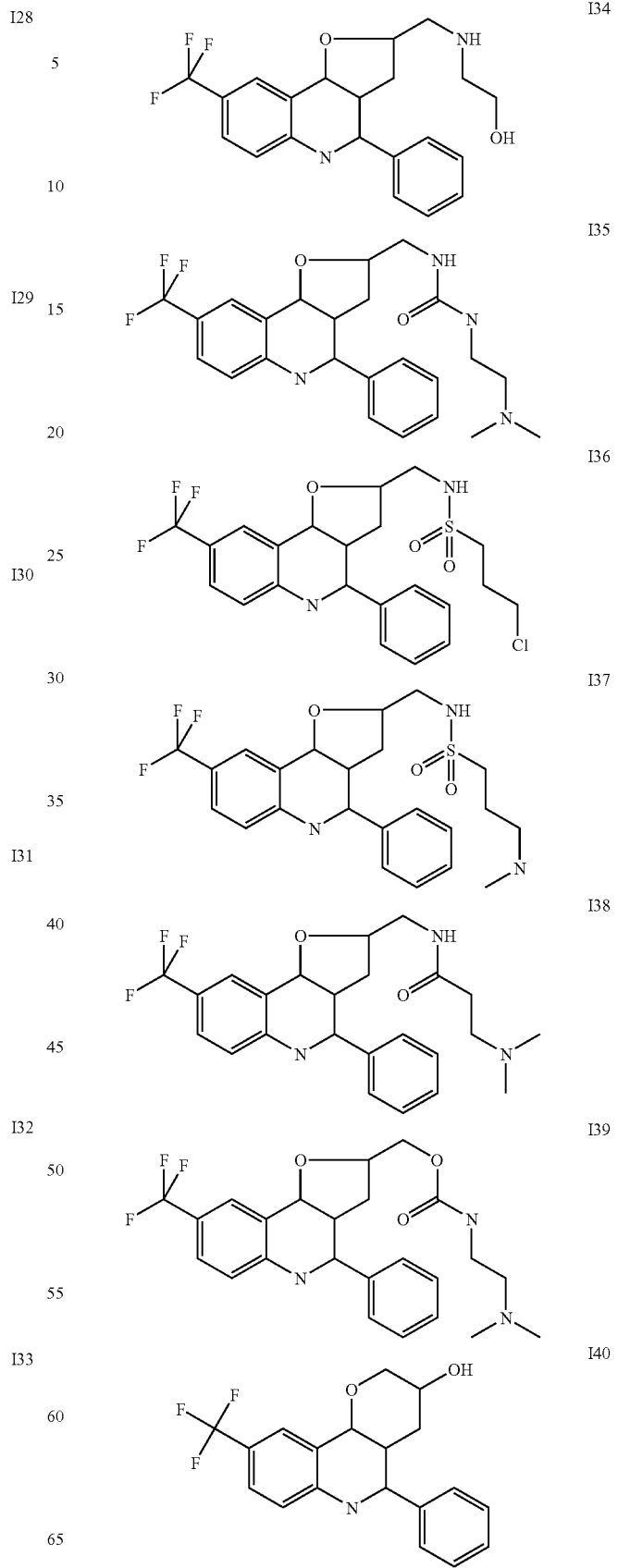

-continued
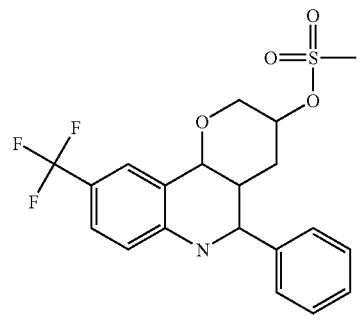
I41
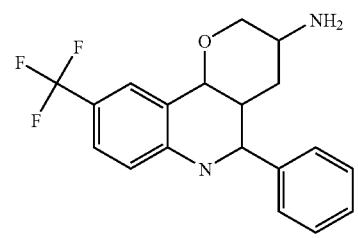
I42
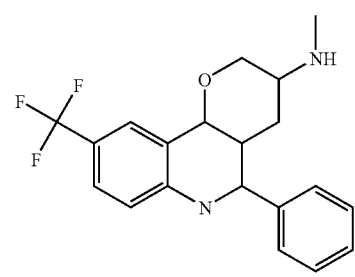
I43
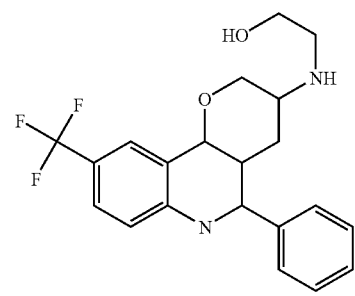
I44
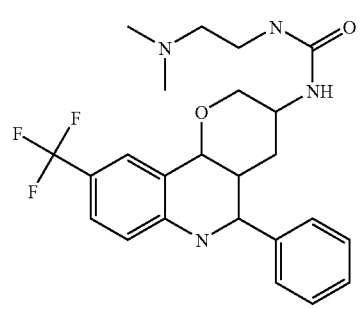
I45
-continued
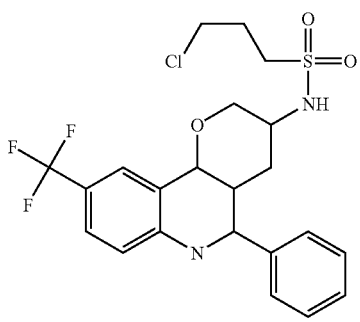
I46
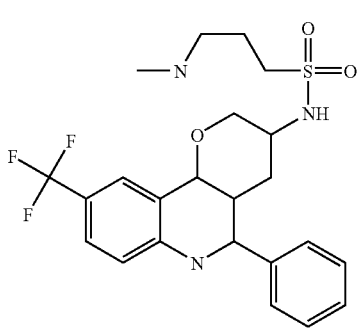
I47
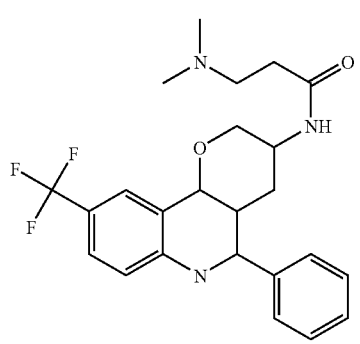
I48
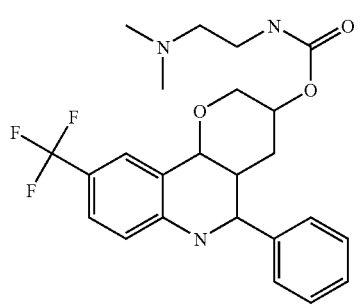
I49
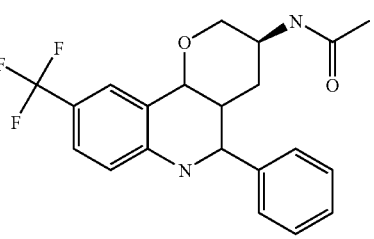
I50

-continued
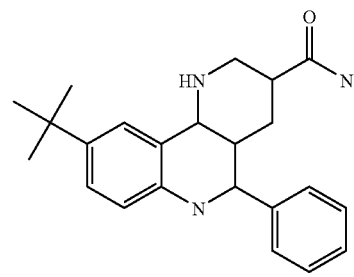 I51
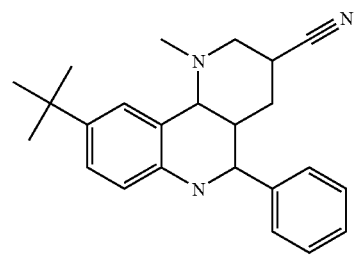 I52
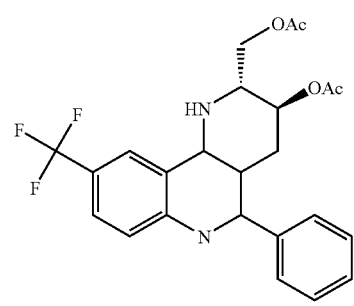 I53
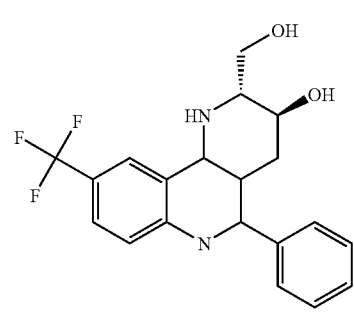 I54
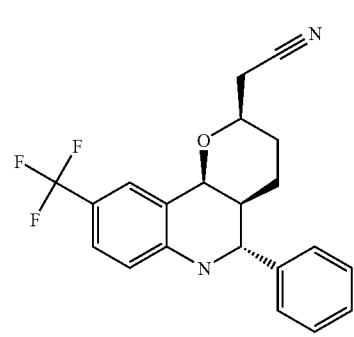 I55
-continued
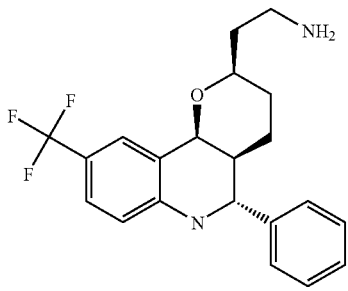 I56
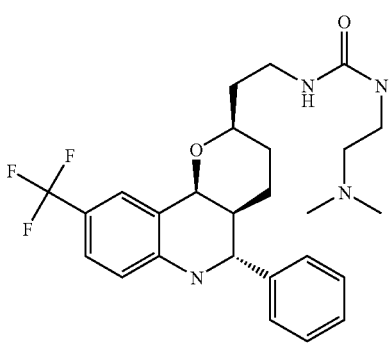 I57
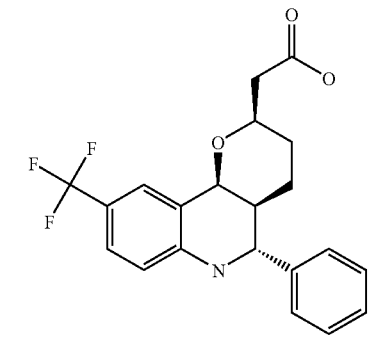 I58
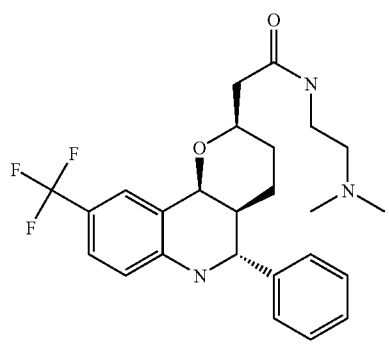 I59

6. A process for the preparation of a compound or compounds of the formula I according to claim 1 and salts, tautomers and stereoisomers thereof, characterized in that
a compound of the formula II

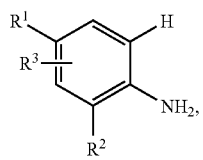

in which $R^1$, $R^2$ and $R^3$ have the meanings indicated in claim 1, is reacted with a compound of the formula III

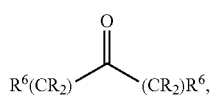

in which
$R^6$ has the meanings indicated in claim 1, and
with a compound of the formula IV, the double-bond isomer (E isomer) thereof or mixtures thereof

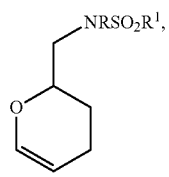

in which R and $R^1$ have the meanings indicated in claim 1,
and, if desired, a radical $R^7$ which denotes H is converted into a radical $R^7$ which has a meaning other than H,
and/or, if desired,
a base or acid of the formula I is converted into one of its salts.

7. A process according to claim 6, characterised in that the reaction is carried out in the presence of a protonic acid or Lewis acid.

8. A process according to claim 6, characterised in that the reaction is carried out in the presence of trifluoroacetic acid, hexafluoroisopropanol, bismuth(III) chloride, ytterbium(III) triflate, scandium(III) triflate or cerium(IV) ammonium nitrate.

9. A pharmaceutical composition, comprising at least one compound of the formula I according to claim 1 and/or salts, tautomers and stereoisomers thereof, including mixtures thereof in all ratios, and optionally excipients and/or adjuvants.

10. A mixture comprising one or more compounds of the formula I of claim 1 and amount of one or more compounds of the formula V

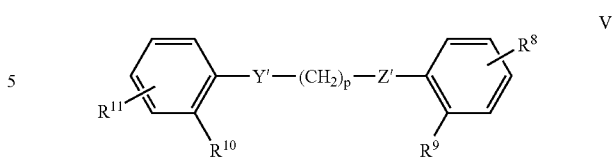

in which
Y' and Z' each, independently of one another, denote O or N, $R^9$ and $R^{10}$ each, independently of one another, denote H, OH, halogen, OC1-10-alkyl, OCF$_3$, NO$_2$ or NH$_2$, n denotes an integer between 2 and 6, each inclusive, and $R^8$ and $R^{11}$ are each, independently of one another, in the meta- or para-position and are selected from the group:

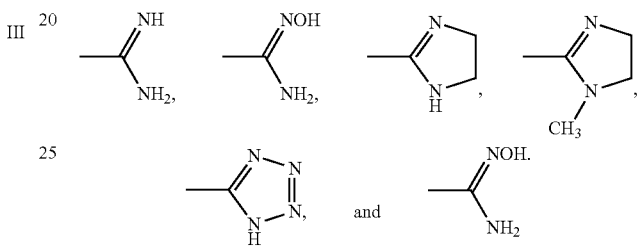

11. The mixture according to claim 10, where the compound of the formula V is pentamidine or salts thereof.

12. A compound or compounds of the following formula I119:

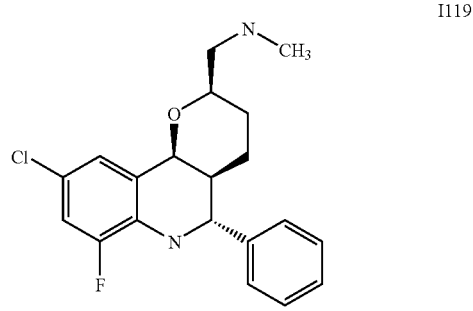

and tautomers, salts and stereoisomers thereof, including mixture therefore in all ratios.

13. A compound or compounds according to claim 1 in which $R^1$ denotes A, CF$_3$, OCF$_3$, SA, SCN, CH$_2$CN, —OCOA, Hal, SCF$_3$, t-butyl, —CH(CH$_3$)CH$_2$CH$_3$, isopropyl, ethyl or methyl.

14. A compound or compounds according to claim 1, in which
$R^6$ denotes one of the following groups:

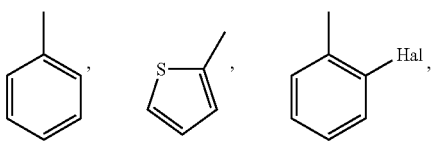

-continued
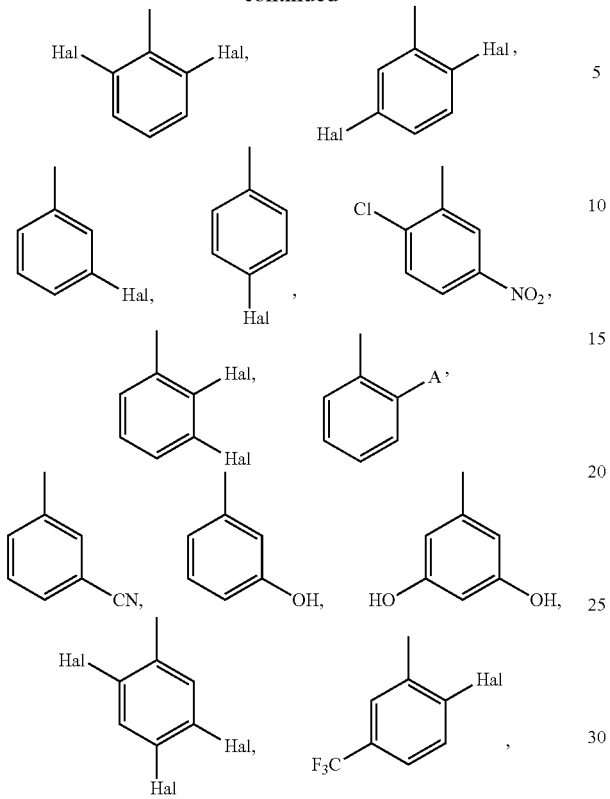
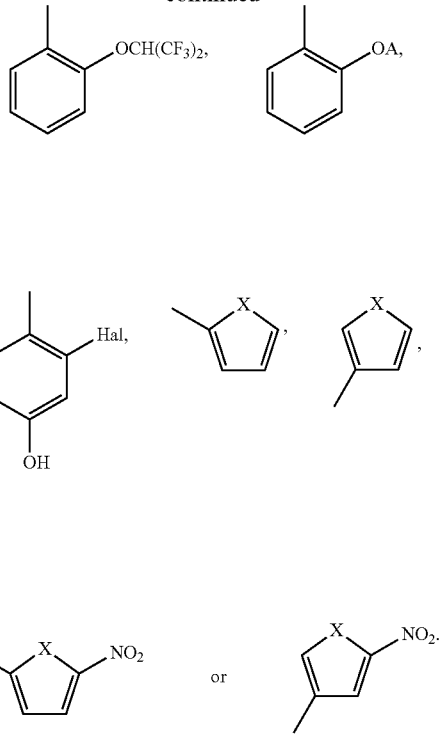
* * * * *